US011292825B2

(12) United States Patent
Clo et al.

(10) Patent No.: US 11,292,825 B2
(45) Date of Patent: Apr. 5, 2022

(54) PROTEIN CONJUGATES

(71) Applicant: Novo Nordisk AS, Bagsvaerd (DK)

(72) Inventors: Emiliano Clo, Copenhagen (DK);
Mikael Kofod-Hansen, Broenshoej (DK); Henrik Sune Ramirez-Andersen, Holte (DK); Nils Langeland Johansen, Koebenhavn OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 62 days.

(21) Appl. No.: 15/763,857

(22) PCT Filed: Sep. 30, 2016

(86) PCT No.: PCT/EP2016/073470
§ 371 (c)(1),
(2) Date: Mar. 28, 2018

(87) PCT Pub. No.: WO2017/055582
PCT Pub. Date: Apr. 6, 2017

(65) Prior Publication Data
US 2018/0282387 A1  Oct. 4, 2018

(30) Foreign Application Priority Data

Oct. 1, 2015 (EP) .................................. 15187937

(51) Int. Cl.
| C07K 14/61 | (2006.01) |
| A61K 47/68 | (2017.01) |
| A61K 47/64 | (2017.01) |
| A61K 47/65 | (2017.01) |
| A61K 38/27 | (2006.01) |

(52) U.S. Cl.
CPC .............. *C07K 14/61* (2013.01); *A61K 38/27* (2013.01); *A61K 47/646* (2017.08); *A61K 47/65* (2017.08); *A61K 47/6811* (2017.08); *A61K 47/6889* (2017.08)

(58) Field of Classification Search
None
See application file for complete search history.

(56) References Cited

U.S. PATENT DOCUMENTS

| 3,914,252 A | 10/1975 | Gordon |
| 7,404,956 B2 | 7/2008 | Peters et al. |
| 8,492,530 B2 | 7/2013 | Schellenberger et al. |
| 8,697,396 B2 | 4/2014 | Dall'Acqua et al. |
| 10,537,644 B2 | 1/2020 | Huang et al. |
| 11,208,452 B2 | 12/2021 | Kjeldsen et al. |
| 2003/0162949 A1 | 8/2003 | Cox |
| 2004/0180054 A1 | 9/2004 | Kim et al. |
| 2005/0233417 A1 | 10/2005 | Cooper et al. |
| 2005/0287153 A1 | 12/2005 | Dennis |
| 2006/0094083 A1 | 5/2006 | Choi et al. |
| 2006/0094655 A1 | 5/2006 | Guyon et al. |
| 2006/0183197 A1 | 8/2006 | Andersen et al. |
| 2006/0276633 A1 | 12/2006 | Jung et al. |
| 2008/0057004 A1 | 3/2008 | Bell et al. |
| 2009/0036353 A1 | 2/2009 | Behrens et al. |
| 2010/0069605 A1 | 3/2010 | Hoeg-Jensen et al. |
| 2010/0239554 A1 | 9/2010 | Schellenberger et al. |
| 2011/0054151 A1 | 3/2011 | Lazar et al. |
| 2012/0116056 A1 | 5/2012 | Sun et al. |
| 2013/0028918 A1 | 1/2013 | Song et al. |
| 2014/0227264 A1 | 8/2014 | Hamilton et al. |
| 2015/0037359 A1* | 2/2015 | Schellenberger ....... A61P 27/00 424/178.1 |
| 2015/0158905 A1 | 6/2015 | Martin |
| 2016/0000932 A1 | 1/2016 | Gegg et al. |
| 2018/0161448 A1 | 6/2018 | Heo et al. |
| 2018/0291076 A1 | 10/2018 | Kjeldsen et al. |
| 2020/0261595 A1 | 8/2020 | Moeller Tagmose et al. |
| 2021/0393745 A1 | 12/2021 | Tagmose et al. |

FOREIGN PATENT DOCUMENTS

| CN | 1604965 A | 4/2005 |
| CN | 102666586 A | 9/2012 |
| DE | 257197 A1 | 6/1988 |
| DE | 286509 | 1/1991 |
| EP | 1996220 A2 | 12/2008 |
| EP | 2164873 A1 | 3/2010 |
| EP | 3260139 | 12/2017 |
| JP | 2008528549 A | 7/2008 |
| JP | 2008530178 A | 8/2008 |
| KR | 20080095141 A | 10/2008 |
| WO | 91/01743 A1 | 2/1991 |
| WO | 92/09690 A2 | 6/1992 |
| WO | 97/11178 A1 | 3/1997 |
| WO | 98/22577 A1 | 5/1998 |

(Continued)

OTHER PUBLICATIONS

Chen et al. "Fusion Protein Linkers: Property, Design and Functionality" Adv. Drug Deliv. Rev. 65:1357-1369. (Year: 2013).*
Berthelmann et al. "Versatile c3-symmertric scaffolds and their use for covalent stabilization of the foldon trimer" Organic & Biomolecular Chemistry 12:2606-2614. (Year: 2014).*
Berg et al. Biochemistry, 5th Edition. New York: W H Freeman, p. 925 (Year: 2002).*
Abbasi et al. "Dendrimers: synthesis, applications, and properties." Nanoscale Research Letters. 2014 vol. 9 No. 1; 247 pp. 1-10. EP SR.
Berg et al. "Biochemistry" 2002. W.H.Freeman and Co, New York p. 925, figure 33.8. EP SR.
Berthelmann et al. "Versatile C3-symmetric scaffolds and their use for covalent stabilization of the foldon trimer" Organic and Biomolecular Chemistry. 2014 vol. 12 No. 16 pp. 2606-2614. EP SR.

(Continued)

*Primary Examiner* — Sudhakar Katakam
*Assistant Examiner* — Zachary J Miknis
(74) *Attorney, Agent, or Firm* — Jianjie Hu

(57) ABSTRACT

The invention relates to protein conjugates and in particular conjugates of more than two protein or polypeptides. The compounds include a trivalent linker moiety that enables efficient production of desired products.

16 Claims, 2 Drawing Sheets
Specification includes a Sequence Listing.

(56) References Cited

FOREIGN PATENT DOCUMENTS

| | | | |
|---|---|---|---|
| WO | 0103737 | A1 | 1/2001 |
| WO | 01/45746 | A2 | 6/2001 |
| WO | 02055532 | A2 | 7/2002 |
| WO | 02/077036 | A2 | 10/2002 |
| WO | 04029207 | A2 | 4/2004 |
| WO | 2004101739 | A2 | 11/2004 |
| WO | 2005001025 | A2 | 1/2005 |
| WO | 2005047334 | A1 | 5/2005 |
| WO | 2005047335 | A1 | 5/2005 |
| WO | 2005047336 | A1 | 5/2005 |
| WO | 2005047337 | A1 | 5/2005 |
| WO | 2006048777 | A2 | 5/2006 |
| WO | 2006/081249 | A2 | 8/2006 |
| WO | 2006087354 | | 8/2006 |
| WO | 2006107124 | A1 | 10/2006 |
| WO | 2007/073486 | A2 | 6/2007 |
| WO | 2007068906 | A2 | 6/2007 |
| WO | 2007/103515 | A2 | 9/2007 |
| WO | 2008019368 | A2 | 2/2008 |
| WO | 2008/049931 | A1 | 5/2008 |
| WO | 08052108 | A2 | 5/2008 |
| WO | 2008049711 | A1 | 5/2008 |
| WO | 08092117 | A2 | 7/2008 |
| WO | 2008147143 | A2 | 12/2008 |
| WO | 2008147456 | A2 | 12/2008 |
| WO | 2009015345 | A1 | 1/2009 |
| WO | 2009023270 | A2 | 2/2009 |
| WO | 2009053368 | A1 | 4/2009 |
| WO | 09155513 | A2 | 12/2009 |
| WO | 2010/001196 | A1 | 1/2010 |
| WO | 2010011096 | A2 | 1/2010 |
| WO | 2011018227 | A2 | 2/2011 |
| WO | 2011059684 | A1 | 5/2011 |
| WO | 2011122921 | A2 | 10/2011 |
| WO | 2011/144756 | A1 | 11/2011 |
| WO | 2012008779 | A2 | 1/2012 |
| WO | 2012138920 | A1 | 10/2012 |
| WO | 2013004842 | A2 | 1/2013 |
| WO | 2013170272 | A2 | 11/2013 |
| WO | 2014/195452 | A1 | 12/2014 |
| WO | 2015/038938 | A1 | 3/2015 |
| WO | 15081073 | A2 | 6/2015 |
| WO | 15132364 | A1 | 9/2015 |
| WO | 2016/042093 | A1 | 3/2016 |
| WO | 2016133372 | A2 | 8/2016 |
| WO | 2016178905 | A1 | 11/2016 |
| WO | 2016193380 | A1 | 12/2016 |
| WO | 2017031034 | A2 | 2/2017 |
| WO | 2017055582 | A1 | 4/2017 |
| WO | 2018185131 | A2 | 10/2018 |

OTHER PUBLICATIONS

Life Technologies. "Sulfhydryl-reactive Crosslinker Chemistry." 2015. Accessed Mar. 6, 2015. https://www.lifetechnologies.com/in/en/home/life-science/protein-biology/protein-biology-learning-center/protein-biology-resource-library/pierce-protein-methods/sulfhydryl-reactive-crosslinker-chemistry.html. ISR.

Kontermann R. E. et al., Strategies for extended serum half-life of protein therapeutics, Current Opinion in Biotechnology, 2011, vol. 22, No. 6, pp. 868-876.

Huang C., Receptor-Fc fusion therapeutics, traps, and MIMETIBODY technology, Current Opinion in Biotechnology, 2009, vol. 20, No. 6, pp. 692-699.

Chantalat L. et al., The Crystal Structure of Wild-Type Growth Hormone at 2.5 A resolution, Protein and Peptide Letters, 1995, vol. 2, No. 2, pp. 333-340.

De Vos A. M. et al., Human growth hormone and extracellular domain of its receptor: crystal structure of the complex, Science, 1992, vol. 255, pp. 306-312.

Cunningham B. C. et al., Rational design of receptor-specific variants of human growth hormone, Proceedings of the National Academy of Sciences, National Academy of Sciences, US, 1991, vol. 88, No. 8, XP00020231, pp. 3407-3411.

Cunningham B. C. et al., High-Resolution Epitope Mapping of hGH-Receptor Interactions by Alanine-Scanning Mutagenesis, Science, 1989, vol. 244, No. 4908, pp. 1081-1085.

Kasimova M. R. et al., NMR Studies of the Backbone Flexibility and Structure of Human Growth Hormone: A Comparison of High and Low pH Conformations, Journal of Molecular Biology, 2002, vol. 318, pp. 679-695.

Lee C. H. et al., Expression and characterization of human growth hormone-Fc fusion proteins for transcytosis induction, Biotechnology and Applied Biochemistry, 2007, vol. 46, pp. 211-217.

Wells, "Binding in the Growth Hormone Receptor Complex," Proc. Natl. Acad. Sci. USA, 1996, vol. 93, pp. 1-6.

Yang et al., "Activation of Growth Hormone Receptors by Growth Hormone and Growth Hormone Antagonist Dimers: Insights into Receptor Triggering," Mol. Endocrinol., 2008, vol. 22, No. 4, pp. 978-988.

Pearce et al., "Growth Hormone Binding Affinity for Its Receptor Surpasses the Requirements for Cellular Activity," Biochemistry, 1999, vol. 38, pp. 81-89.

Nomura et al., "Trivalent ligands for CXCR4 bearing polyproline linkers show specific recognition for cells with increased CXCR4 expression," Org. Biomol. Chem. 2015, vol. 13, pp. 8734-8739.

Arakawa, Takeshi et al. "A Plant-Based Cholera Toxin B Subunit-Insulin Fusion Protein Protects Against the Development of Autoimmune Diabetes." Nature Biotechnology 1998 vol. 16(10) pp. 934-938.

Podust et al., Extension of in vivo half-life of biologically active peptides via chemical conjugation to XTEN protein polymer, Protein Engineering, Design & Selection,Oct. 16, 2013, vol. 26, No. 11, pp. 743-753.

Jochen G. Salfeld, "Isotype Selection in Antibody Engineering," Nature Biotechnology, Dec. 2007, vol. 25, pp. 1369-1372.

Singh et al., Novel Approaches and Strategies for Biologies, Vaccines and Cancer Therapies, 1st Edition, Jan. 5, 2015, p. 134.

\* cited by examiner

SEQUENCE LISTING

```
<160> NUMBER OF SEQ ID NOS: 5

<210> SEQ ID NO 1
<211> LENGTH: 217
<212> TYPE: PRT
<213> ORGANISM: homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160
```

-continued

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 2
<211> LENGTH: 14
<212> TYPE: PRT
<213> ORGANISM: homo sapiens

<400> SEQUENCE: 2

Pro Lys Ser Cys Asp Lys Thr His Thr Cys Pro Pro Cys Pro
1               5                   10

<210> SEQ ID NO 3
<211> LENGTH: 217
<212> TYPE: PRT
<213> ORGANISM: homo sapiens

<400> SEQUENCE: 3

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Arg Leu Thr Val Asp Lys Ser Arg Trp Gln Glu Gly Asn Val
        180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 4
<211> LENGTH: 11
<212> TYPE: PRT
<213> ORGANISM: homo sapiens
<220> FEATURE:

```
<221> NAME/KEY: misc_feature
<222> LOCATION: (9)..(9)
<223> OTHER INFORMATION: Corresponds to S228. Possible variant P)

<400> SEQUENCE: 4

Ser Lys Tyr Gly Pro Pro Cys Pro Ser Cys Pro
1               5                   10

<210> SEQ ID NO 5
<211> LENGTH: 191
<212> TYPE: PRT
<213> ORGANISM: Homo sapiens

<400> SEQUENCE: 5

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

PROTEIN CONJUGATES

CROSS-REFERENCE TO RELATED APPLICATIONS

This application is a 35 U.S.C. § 371 National Stage application of International Application PCT/EP2016/073470 (WO2017/055582), filed Sep. 30, 2016, which claims priority to European Patent Application 15187937.6, filed Oct. 1, 2015; the contents of which are incorporated herein by reference.

In accordance with 37 C.F.R. § 1.52(e)(5), Applicants enclose herewith the Sequence Listing for the above-captioned application entitled "150010US01_SeqList.txt", created on Mar. 20, 2018. The Sequence Listing is made up of 7 kilobytes, and the information contained in the attached "SEQUENCE LISTING" is identical to the information in the specification as originally filed. No new matter is added.

TECHNICAL FIELD

The field of the invention is protein conjugates and methods of preparing such.

BACKGROUND

Protein conjugates are useful in multiple situations and the identification and development of biological therapeutic compounds of increasing complexity have increase the focus on attractive methods for preparing such compounds. Difficulties with linkage of two or more proteins arise as proteins are not as stable as traditional chemical moieties and traditional reaction chemistry can usually not be applied without damaging the proteins.

Conjugation of a protein with a property modifying agent has been obtained by various methods linking to various amino acid residues such as the N-terminal, the C-terminal, and internal amino acid residues such as Cys, Lys, Gln and Ser that can be reacted with various reactive groups e.g. placed at the end of the property modifying agent.

Traditionally proteins have been linked recombinant by expression of fusion proteins possibly linked by a peptide linker. This strategy may result in expression of very large protein molecules which may encounter production problems and thus limits the scope of compounds that can be efficiently produced.

In an alternative to fusion proteins, WO2005001025 also describes native ligations e.g. linkage of a thioester to an N-terminal cysteine resulting in amide bond formation. Again, such linkage is limited to the N-terminal of the protein.

Chemical linkage of proteins have been explored using di-halomethylene-benzene, 'Click' chemistry between an azide and an acetylene unit and PEG linkers with propionaldehyde at the ends such as described in WO201001196.

Further exploration of linkage technologies is desired to broaden the scope of compound formats that can be easily and effectively produced.

SUMMARY

The present invention relates to protein conjugates and methods of preparing such conjugates. The methods may be useful to covalently link two or more protein(s) in an ordered and regio-selective fashion. The protein conjugates may comprise one or more therapeutic proteins as well as one or more effector protein(s). The present invention provides an efficient process for protein-protein conjugation by means of thiol reactive linkers. By using e.g. halo-acetamide with different leaving groups the linkage of reactants can be controlled and linkage via one or more thiol-ether(s) obtained.

Examples of such conjugates are:

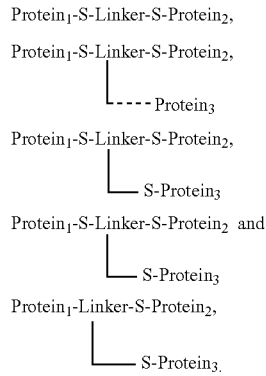

As demonstrated herein the method has been successfully employed for the formation of Fc-conjugates. Fc domains holds two Fc polypeptides and by using a trivalent linker the Fc domains can be covalently bond to a protein of interest via two cysteine residues, e.g. one in each Fc polypeptide representing two individual proteins in the general structure.

An aspect of the invention relates to a protein-Linker-Fc conjugate comprising covalent linkage between a Linker and each of the polypeptides of the Fc-domain.

The invention thus relates to a compound of structure

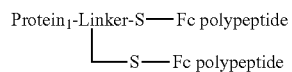

The linkages to the Fc polypeptides are via sulfur atom's (—S—) derived from cysteine residues in the Fc polypeptides.

The Linker is a chemical moiety and Protein$_1$ is thus covalently linked to Protein$_2$ and Protein$_3$ via the linker and the sulfur atoms.

An aspect of the invention relates to trivalent linkers as used herein for preparing various protein conjugates. The linker in an embodiment includes a central unit referred to as -U=which hold at least three bonding opportunities. Other features of the linker are spacer elements 1-3 (S1-S3) that links the central unit with the reactive ends (R1-R3), which are used to enable conjugation of the linker with the protein.

In one embodiment the trivalent linker has the structure:

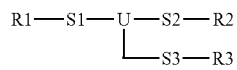

wherein U represent a central unit,
S1, S2 and S3 represent individual spacers and
R1, R2 and R3 individually represent a reactive end.

Examples provided herein demonstrate that a Nitrogen atom is a suitable central unit and that thiol reactive ends are suitable for linkage to free cysteines in one or more of the proteins to be conjugated.

An aspect of the invention relates to a method for preparing protein conjugates where at least two proteins are to be conjugated. The use of linkers having two different reactive ends enables an ordered reaction process increasing specificity, purity and/or yield. In one embodiment the reactive ends of the linker holds two halo-acetamides with different halogens providing reactive ends with different reactivity. After a first conjugation step the conjugate intermediate can be reacted with the 2 (or 3) protein. The efficacy of the method is increased if one of the halogen of the halo-acetamides is exchanged from Cl to I. The method may be employed for conjugation of two or more proteins and also if two of the proteins are identical and to be conjugated to the linker at the same time.

An embodiment of the invention relates to a method for preparation of a protein conjugate, wherein Protein$_1$-SH, Protein$_2$-SH and a thiol reactive linker are coupled together obtaining a protein conjugate of Formula II

(Formula II)

wherein the thiol reactive linker has the structure:

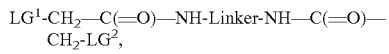

wherein $LG^1$ has a higher reactivity than $LG^2$,
the method comprising the steps of:
a) reacting Protein$_1$-SH with —NH—C(=O)—CH$_2$-LG$^1$ of the linker
b) obtaining a conjugate intermediate: Protein$_1$-S—CH$_2$—C(=O)—NH-Linker-NH—C(=O)—CH$_2$-LG$^2$
c) performing a leaving group exchange reaction increasing the reactivity of $LG^2$.
d) reacting the intermediate of c) with Protein$_2$-SH
e) obtaining the protein conjugate.

As can be foreseen from the disclosure herein, the method, linkers and compounds disclosed may have multiple uses, such as in the development of therapeutic products.

Figure 1:
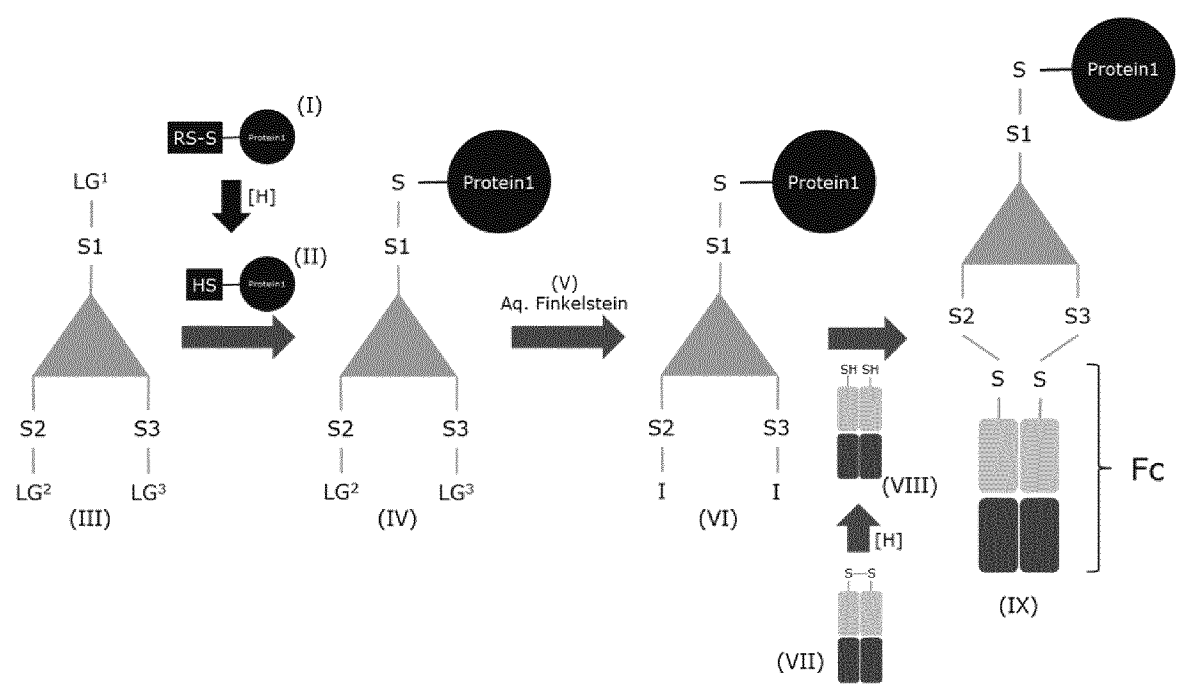
FIG. 1 shows a schematic illustration of a protein to Fc conjugation according to the invention. The trivalent linker includes, the central unit (here illustrated by triangle), independent spacer element S1, S2 and S3 and leaving groups $LG^1$, $LG^2$ and $LG^3$. The method is described as follows:
1) Optionally reducing a mixed disulfide (I) of the protein to be conjugated obtaining a protein with a free Cys (—SH) (II)
2) Alkylating the free Cys (—SH) (II) with the trivalent linker (III) affording a Cys conjugated protein linker intermediate conjugate (IV)
3) Activating leaving groups $LG^2$ and $LG^3$ of the conjugate intermediate (IV) via an aqueous Finkelstein iodine exchange reaction (V) affording a iodine activated conjugate intermediate (VI)
4) Selective reduction of a Fc-domain disulfide bridge (VII) affording an Fc-domain with two reduced cysteines (—SH) (VIII)
5) Coupling of said Fc-domain (VIII) with the iodine activated conjugate intermediate (VI) affording a protein-Fc conjugate (IX).
Figure 2:
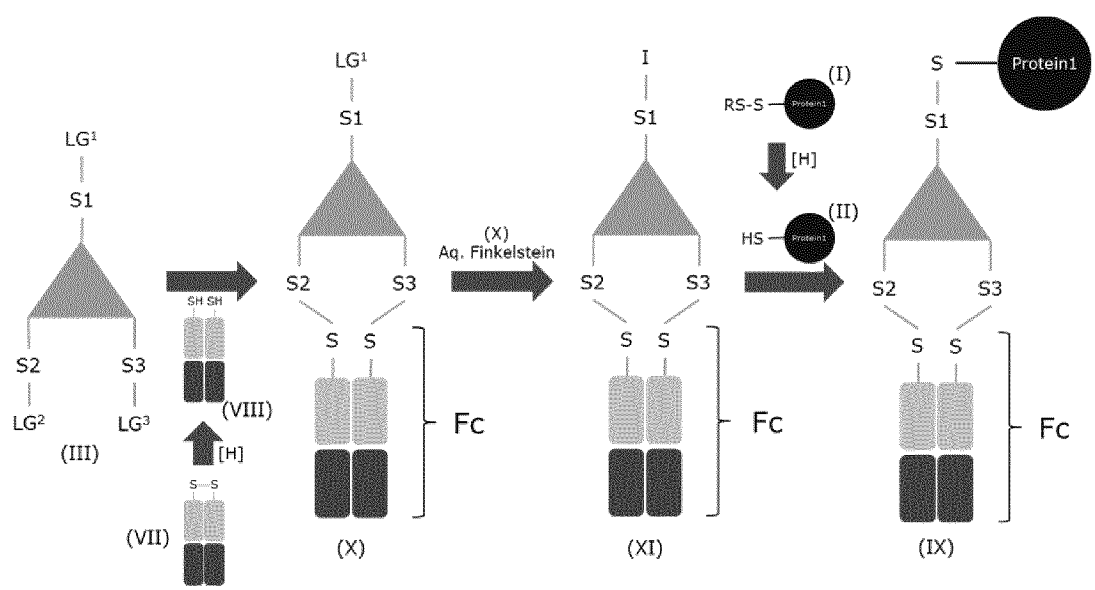
FIG. 2 shows a schematic illustration of an Fc protein conjugation according to the invention. The trivalent linker includes, the central unit (here illustrated by triangle), independent spacer element S1, S2 and S3 and leaving groups $LG^1$, $LG^2$ and $LG^3$. The method is described as follows.

1) Selective reduction of a Fc-domain disulfide bridge (VII) affording an Fc-domain with two reduced cysteines (—SH) (VIII)
2) Alkylating the Fc-domain (VIII) with an trivalent linker (III) affording an $LG^1$-A-B-Fc conjugate intermediate (X)
3) Optionally reducing a mixed disulfide (I) of the protein to be conjugated obtaining a protein with a free Cys (—SH) (II)
4) Activating leaving groups $LG^1$ of the conjugate intermediate (X) via an aqueous Finkelstein iodine exchange reaction (V) affording a iodine activated conjugate intermediate (XI)
5) Coupling said protein with a free Cys (—SH) (II) with the iodine activated conjugate intermediate (XI) affording a protein-Fc conjugate (IX).

SEQUENCE INFORMATION

Standard Fc polypeptide sequences for IgG1 and IgG4 are provided in the sequence listing and replicated here for ease of information.

```
SEQ ID NO 1: IgG1 C2-C3
Corresponding to AA231-447 of full length
heavy chain according to EU numbering
    APELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPGK
Amino acid residues underlined correspond
to L234, L235, G237 and A330 and P331

SEQ ID NO 2: IgG1 hinge
Corresponding to AA217-230 of full length
heavy chain according to EU numbering
PKSCDKTHTCPPCP SEQ ID NO 3: IgG4 C2-C3
Corresponding to AA231-447 of full length
heavy chain according to EU numbering
APEFLGGPSV FLFPPKPKDT LMISRTPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGK

SEQ ID NO 4: IgG4 hinge
Corresponding to AA217-230 of full length
heavy chain according to EU numbering
SKYGPPCPSCP
S in bold and underlined corresponds to
S228 of full length IgG4 heavy chain
according to EU numbering.
```

DESCRIPTION

The present invention relates to protein conjugates and method of preparing such conjugates. The methods may be useful to covalently link two or more polypeptides.

Protein Conjugates

The present invention relates to protein conjugates e.g. compound including two or more proteins or polypeptides that are covalently linked by post translational chemical reactions. Such compounds and molecules may find use in multiple areas and in particular in relation to the development of therapeutic compounds.

Protein/Polypeptide

The proteins or polypeptides may be any proteins or polypeptides that a skilled person wishes to covalently link together. The present invention thus goes beyond the exemplified compounds as a skilled person can easily adapt the method to other proteins and polypeptides. In the following focus will be on conjugations involving a therapeutic protein and an effector protein aimed at modifying the properties of the therapeutic protein. Again alternative uses of compounds of the invention are foreseen.

As can be seen herein the technologies developed are functional for proteins/polypeptides of various sizes. It is well-know that handling of proteins/polypeptides is substantially more challenging than handling of small peptides that can be treated more or less as small molecules. In one embodiment one or more or the proteins/polypeptides are at least 40 amino acids long, such as at least 60, 80 or 100 amino acids long.

In one embodiment the proteins/polypeptides are all at least 40 amino acids long, such as at least 60, 80 or 100 amino acids long.

Therapeutic Protein

A therapeutic protein is a protein or polypeptide e.g. an amino acid sequence that is useful in a method of treatment of a disease or disorder.

Growth Hormone

The term "growth hormone compound" as used herein collectively refers to a growth hormone molecule retaining substantially the functional characteristics of mature human growth hormone identified by SEQ ID NO 5. The compound may thus be a growth hormone, a growth hormone fusion protein, a growth hormone variant or analogue or a growth hormone conjugate or derivative including also acylated or alkylated growth hormone.

The ability of a growth hormone compound to stimulate signalling through the growth hormone receptor (GHR) may be measured in an in vitro cell based assay such as a BAF assay (Assay 2 herein).

As a GH variant or GH compound comprising a variant amino acid sequence or other modification may have other advantageous, the GH activity as measured in a BAF assay can be lower than for human growth hormone (hGH) while the variant or compound is still an attractive molecules as long as the molecules are able to stimulate the receptor and proliferation of the cells to a reasonable degree.

In one such embodiment the in vitro activity is measured in a BAF assay. In one embodiment the GH variant has an equal in vitro activity in a BAF assay compared to hGH identified by SEQ ID NO 5. As described in Assay 2, the result of the BAF assay (BAF ratio) may be expressed as the ratio between $EC_{50}$ of the test compound (variant/GH compound) and $EC_{50}$ for the reference (hGH/GH compound w. hGH sequence). In one embodiment the in vitro activity of the GH variant or the GH compound is comparable to the in vitro activity of hGH or the equivalent GH compound comprising the hGH sequence. Comparable here means that the ratio of BAF activity is within the interval of 1/100-100/1 or such as 1/10-10/1.

Rat models are frequently used to test biological effect of GH variants and compounds. Testing may be performed in normal rats and/or in hypophysectomised rats.

The Sprague Dawley rat is frequently used and methods for testing are described in Assay 3 and 4. Such testing may provide information on several pharmacokinetic parameters such as the AUC, $T_{1/2}$ (half-life) and MRT (mean residence time) which are relevant in order to determine the total exposure and the duration of the presence of a given compound in the blood of a recipient. Furthermore an induction of the IGF-1 response, one of more characteristics for the biological effects of hGH, can be measured (Assay 5).

As an alternative or supplement minipigs may be used as described in Assay 6.

In one embodiment the GH conjugate has an increased half-life compared to hGH (SEQ ID NO 5).

In one embodiment the GH conjugate according to the invention has an increased in vivo $T_{1/2}$ compared to hGH (SEQ ID NO 5).

It is noted that hGH has a $T_{1/2}$ of approximately 12-14 minutes in the described assay 3 herein. Although not equivalent with half-life in humans, it is contemplated that an increased in vivo $T_{1/2}$ in rats or minipigs will also translate into an extended in vivo presence in a therapeutic setting.

In one embodiment the GH conjugate has a $T_{1/2}$ above 30 minutes, or above 60 minutes, or above 90 minutes or above 120 minutes. In further embodiments $T_{1/2}$ is above 60 minutes or 1 hour, such as above 2 hours or preferably above 4 hours. In on embodiment the GH conjugate has a $T_{1/2}$ of 2-10 hours, such as 4-8 hours.

In one embodiment the extended $T_{1/2}$ is measure after intravenous (iv.) or subcutaneous (sc.) administration to rats or minipigs. The skilled person will know how such assay can be modified, depending on the tools available for detection of the GH variant or GH compound.

In one embodiment the GH compound has an increased half-life compared to hGH. In one embodiment the GH compound has a $T_{1/2}$ of more than 8 hours, such as more than 12 hours, such as more than 24 hours. In one embodiment the GH compound has a $T_{1/2}$ of more than 8 hours, such as more than 12 hours, such as more than 24 hours, when measured after a single i.v. dose of 15 nmol to normal rats.

In one embodiment the GH compound has a $T_{1/2}$ of more than 8 hours, such as more than 12 hours, such as more than 24 hours, when measured after a single i.v. dose of 15 nmol to hypophysectomised rats (see Assay 4 herein).

In one embodiment the GH compound has a $T_{1/2}$ of more than 48 hours, such as more than 60 hours, such as more than 72 hours, when measured after a single iv. dose of 15 nmol to hypophysectomised rats.

The IGF-1 response may be measured after dosing of a GH compound such as described in Assay 5, herein, although the skilled person will know to apply alternative methods as well. The plasma concentration of IGF-1 in rats after a single dose a GH should preferably increase over a period of time corresponding to the increased plasma concentration of the GH compound.

In one embodiment the GH compound according to the invention is capable of inducing an IGF-1 response.

An IGF-1 response may thus be stronger than the response observed for hGH by reaching a higher plasma concentration of IGF-1. The concentration of plasma IGF-1 may be detected within 72 hours, such as within 48 hours, such as within 36 hours, such as within 24 hours. To compare effects of different compounds values may be measured at different time points and compared at each individual time point, such as by either of 6, 12, 24, 36, 48, 72, 96, 144, 192, 240, 288, 336 hours after a dosage.

In one embodiment the GH compound induces an increased IGF-1 response. In one embodiment the GH compound induces an IGF-1 response, wherein the IGF-1 response is detected as an increased plasma IGF-1 concentration at up to 96 hours, or such as 6, 12, 24, 36, 48, 72 hours after a single dose of said GH variant or compound. In one embodiment the GH compound induces an extended IGF-1 response. If the plasma concentration of IGF-1 remains high over an extended period of time compared to hGH, the GH compound induces an extended an IGF-1 response. In one embodiment the GH compound induces an extended IGF-1 response compared to the IGF response of wt hGH. In one embodiment the IGF-1 response lasts more than 24 hours, such as more than 48 hours.

The structure of growth hormone proteins is composed of four helixes (helix 1-4) connected by three loops (L1-3), and a C-terminal segment. In human growth hormone (SEQ ID NO 5) helix 1 is defined by AA residue 6-35, helix 2 is defined by AA residues 71-98, helix 3 is defined by AA residue 107-127 and helix for is defined as AA residues 155-184.

Growth hormone molecules including human growth hormone variants and conjugates have been described in multiple documents including WO2011089250, WO2011089255 and WO2012010516.

In one embodiment a growth hormone compound or conjugate according to the invention comprises a GH protein with less than 8 modifications (substitutions, deletions, additions) relative to hGH.

In one embodiment a GH protein comprises less than 7 modifications (substitutions, deletions, additions) relative to hGH. In one embodiment a growth hormone protein comprises less than 6 modifications (substitutions, deletions, additions) relative to human growth hormone.

In one embodiment a growth hormone protein comprises less than 5 modifications (substitutions, deletions, additions) relative to human growth hormone. In one embodiment a growth hormone protein comprises less than 4 modifications (substitutions, deletions, additions) relative to human growth hormone. In one embodiment a growth hormone protein comprises less than 3 modifications (substitutions, deletions, additions) relative to human growth hormone. In one embodiment a growth hormone protein comprises less than 2 modifications (substitutions, deletions, additions) relative to human growth hormone.

In a series of embodiment the growth hormone protein of the growth hormone is at least 95, 96, 97, 98 or 99% identical to human growth hormone identified by SEQ ID NO: 5.

In one embodiment the growth hormone protein is a variant that is stabilized towards proteolytic degradation (by specific amino acid substitutions generated by mutation of the coding DNA sequence)

Non-limiting examples of growth hormone proteins that are stabilized towards proteolytic degradation may be found in WO2011089250.

Protease-stabilized growth hormone protein variants include variants where an additional disulfide bridge is introduced. The additional disulfide bridge preferably connects L3 with helix 2. This may be obtained by introducing two extra cysteine amino acid residues, which in preferred embodiments are substituted for the wild type amino acid residue in positions corresponding to AA84 or AA85 in H2 and AA143 or AA144 in L3 of SEQ ID NO: 5. The growth hormone variant may thus according to the invention preferably comprise a pair of amino acid substitutions corresponding to L73C/S132C, L73C/F139C, R77C/I138C, R77C/F139C, L81C/Q141C, L81C/Y143C, Q84C/Y143C, Q84C/S144C, S85C/Y143C, 585C/5144C, P89C/F146C, F92C/F146C or F92C/T148C in SEQ ID NO:5. In a further embodiment the growth hormone variant comprises a pair of amino acid substitutions corresponding to L81C/Y143C, Q84C/Y143C, S85C/Y143C, 585C/5144C or F92C/T148C in SEQ ID NO: 5.

In one embodiment the growth hormone protein is a growth hormone variant, suited for mono-substitution/site specific modification such as alkylation by one chemical moiety to a free cysteine introduced by amino acid substitutions (by mutation of DNA sequence) possibly in addition to any protease stabilizing amino acid changes described above. A non-limiting list of growth hormone variants suitable for alkylation may be found in WO2011089255.

The terms "free Cys" or "free cysteine" are used herein to indicate a cysteine amino acid residue which in the reduced form is available for conjugation, hence having a free thiol group (—SH). In general the free Cys is not engaged in a disulfide bond. Usually the free Cys is a variant amino acid introduced to the protein although a natural Cys may serve as the free Cys. The ability to introduce a free Cys by insertion or amino acid substitution in a protein greatly enhances the options for creating new molecules.

In a further embodiment the protein is a growth hormone variant including a free cysteine. In a further embodiment the protein is a growth hormone variant including a free cysteine introduced in human growth hormone identified by SEQ ID NO.: 5. In a further embodiment the protein is a growth hormone variant including an additional cysteine introduced by an amino acid substitution selected from the group of: T3C, P5C, S7C, D11C, H18C, Q29C, E30C, E33C, A34C, Y35C, K38C, E39C, Y42C, S43C, D47C, P48C, 555C, 557C, P59C, S62, E65C, Q69C, E88C, Q91C, 595C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C. Such introduced Cys residues are termed free Cys substitutions. In a further embodiment the protein is a growth hormone variant including an additional cysteine selected from the group of: T3C, P5C, S7C, D11C, H18C, Q29C, E30C, E33C, A34C, Y35C, E88C, Q91C, 595C, A98C, N99C, S100C, L101C, V102C, Y103C, D107C, S108C, D112C, Q122C and G126C.

In further embodiments the free Cys substitution is located within AA 93-106 in hGH or corresponding residues in hGH variants. In further specified embodiments the free Cys substitution is located within L2, such as within AA 99-106 or AA 99-103 or corresponding residues.

In further embodiment the free Cys substitution is selected from the group of: E30C, Y42C, 555C, 557C, S62C, Q69C, 595C, A98C, N99C, L101C, V102C, and S108C.

In an embodiment the growth hormone variant include one free Cys substitution.

In a further embodiment the free Cys substitution is E30C. In further embodiment the free Cys substitution is Y42C. In a further embodiment the free Cys substitution is 555C. In a further embodiment the free Cys substitution is 557C. In a further embodiment the Cys substitution is 562C. In a further embodiment the free Cys substitution is Q69C. In further embodiment the free Cys substitution is 595C. In a further embodiment the free Cys substitution is A98C. In further embodiment the free Cys substitution is N99C. In a further embodiment the free Cys substitution is S100C. In a further embodiment the free Cys substitution is L101C. In a further embodiment the free Cys substitution is V102C. In a further embodiment the free Cys substitution is S108C.

In a further embodiment the protein is a growth hormone variant including a cysteine substitution selected from Y42C and L101C.

Effector Protein

An effector protein is a polypeptide capable of modifying the properties of the (therapeutic) protein. Examples—but not limited to—of effector proteins are PEG, albumin, XTEN, and Fc-domain, the latter being the key example of the present application.

Fc-Domain

The fragment crystallizable region (Fc region or Fc-domain) of an antibody is the tail of an antibody. For IgG, IgA and IgD antibodies the Fc region contains two identical polypeptides both comprising the second and third constant domains (CH2 and CH3) of the heavy chain. The Fc regions of IgM and IgE antibodies contain three heavy chain constant domains (CH domains 2-4) in each polypeptide chain. The protein sequences of the Fc-domain are herein referred to as Fc polypeptides and usually comprise at least the CH2 and CH3 domains. The Fc-domain may also be referred to as a dimer as the two Fc polypeptides interacts non-covalent and possibly also covalently as hinge cysteines may form disulfide bond(s).

The Fc-domain mediates interaction with cell surface receptors called Fc receptors, as well as some proteins of the complement system. The interaction with the Fc neonatal receptor (FcRn) is of particular interests.

The Fc region enables antibodies to interact with the immune system. The Fc region of an antibody is at least partly responsible for the long in-vivo half-life of antibody molecules, which for an IgG is approximately 720 hours in humans. The Fc-domain is thus an attractive protractor for extending the in-vivo half-life of potential therapeutic compounds.

According to the present invention it has been found that the use of an Fc-domain as a protractor of growth hormone results in a growth hormone conjugate with attractive functionalities.

In one embodiment the isotype of the Fc-domain is IgG, such as subtype IgG1, such as IgG2, such as IgG4.

In one embodiment the Fc domain comprises the CH2 and CH3 domains of human IgG1 defined by SEQ ID NO: 1 or IgG4 defined by SEQ ID NO 3. In one embodiment the growth hormone conjugate comprises two identical Fc polypeptides each defined by SEQ ID NO 1 or SEQ ID NO 3.

The hinge region is the protein segment between CH1 and CH2 of the constant region of the antibody. In one embodiment the Fc-polypeptide comprises a hinge region including one or more cysteine's. In one embodiment the polypeptides of the Fc domain each comprises the sequence as defined by SEQ ID NO: 2 or 4.

In one embodiment the Fc polypeptide comprises a hinge and the CH1 and CH2 domains.

In one embodiment, the hinge region is modified such that the number of cysteine residues in the hinge region is altered, e.g., increased or decreased.

In one embodiment the hinge regions of the Fc polypeptides comprise only one cysteine. In one embodiment this cysteine is capable of forming a disulfide bond with the same cysteine of the second Fc polypeptide. Thus in one embodiment the two polypeptides of the Fc-domain holds two cysteines in the hinge region e.g. one in each polypeptide. As seen in the section describing the preparation of proteins conjugates, such a disulfide bond may be reduced and the thiols use for coupling to the linker and there trough to other proteins.

The cysteines of the Fc polypeptide are capable of forming a disulfide bond, but may act as a free Cys when reduced. In one embodiment the Fc polypeptide comprise a Cys residue. In particular as shown herein the disulfide bonds in the hinge region which links the two Fc polypeptide may be reduced producing two cysteines that can act like free cysteines. In one embodiment the Fc polypeptide comprise a Cys residue in the hinge sequence.

In one embodiment the hinge region of the Fc polypeptide include only native amino acid residues. In one embodiment the hinge region comprise an amino acid insertion or substitution in the hinge region. For heterologous expression a methionine may be encoded by the DNA in the expression vector although not always present in the Fc domain of the conjugate. In on embodiment the Fc polypeptide does not include a methionine at the N-terminal.

In one embodiment the hinge sequence is a truncated version of an IgG hinge sequences, such as the IgG1 or IgG4 hinge sequences specifically mentioned herein.

In one embodiment the hinge sequence of the Fc hinges is derived from the IgG1 hinge sequence PKSCDKTH-TCPPCP (SEQ ID NO: 2).

In one embodiment the hinge sequence is selected from the group consisting of: PKSCDKTHTCPPCP, PPCP, PCP and CP.

In one embodiment the hinge sequence of the Fc hinges is derived from the IgG4 hinge sequence SKYGPPCPSCP (SEQ ID NO: 4). In one embodiment the hinge sequence is selected from the group consisting of: SKYGPPCPS*CP, PSCP, SCPL and CP.

In one embodiment the Fc polypeptide comprise a Cys residue in the hinge sequence. In one embodiment the Fc polypeptide comprise only one Cys residue in the hinge.

In one embodiment the constant region may be modified to stabilize the molecule, for example, in an IgG4 hinge region, residue S228 (marked * above, residue numbering according to the EU index) may be substituted by a proline (S228P). In one embodiment the Fc polypeptides includes a proline residue in position 228, or in a position corresponding to 228 in an IgG4 derived hinge sequence.

The Fc polypeptides of the Fc-domain may thus be covalently linked by disulfide bridges or alternatively non-covalently bound.

In one embodiment the Fc region may be engineered to include modifications within the Fc region, typically to alter one or more of its functional properties, such as serum half-life, complement fixation, Fc-receptor binding, protein stability and/or antigen-dependent cellular cytotoxicity, or lack thereof, among others.

In one embodiment the Fc domain comprises and FcRn binding site, thus any amino acid deletions, insertions or substitutions relative to the wt Fc polypeptide should not disrupt or decrease substantially the ability of the Fc domain to interact with the Fc neonatal receptor similar to what is described in WO05001025. Binding assays for such receptor interactions are well known in the art.

Furthermore, an Fc-domain of the invention may be chemically modified (e.g., one or more chemical moieties can be attached to the Fc part) to alter its degree of glycosylation, again to alter one or more functional properties of the antibody.

A variety of such mutations to the Fc domain have previously been described and the Fc domain according to the present invention may include such mutation as long as the functionality is maintained e.g. the ability to increase the in-vivo half-life of the protein linked thereto.

An IgG1 Fc-domain may comprises one or more, and perhaps all of the following amino acid substitutions that will result in decreased affinity to certain Fc receptors selected from L234A, L235E, and G237A, and/or in reduced C1q-mediated complement fixation selected from A330S and P331S, respectively.

In order to improve binding affinity to FcRn mutations in the Fc may be included to obtain amino acid substitutions such as M428L and/or N434S in an Fc-domain of the IgG1 isotype.

Linker

The linker is a chemical moiety used to covalently link the proteins. The linker is a separate moiety e.g. proteins solely linked by disulfide bonds are not consider to comprise a linker according to the present invention. As seen below the linker may include amino acid, amino acid like and non amino acid elements, while the linker is not itself produced by heterologous expression as part of one or more of the proteins of the conjugate.

As the linker is reacted with a protein a linker radical is formed. The term "-Linker-" is thus intended to mean the chemical unit of the protein-conjugate which is covalently linked to an amino acid residue of each of the proteins of the protein conjugate.

Depending on the attachment point the reactivity of the linker ends will vary. The linker may have various forms depending on the desired product to be obtained. The concept as described herein in an embodiment relates to an ordered conjugation to ensure that different proteins are attached at each end of the linker.

A reactive end is a chemical sub-structure that is useful for conjugation of the linker to an amino acid residue of a protein. The reactive end may be suited for linkage to the N-terminal, the C-terminal or internal amino acid residues. Various formats are known in the art including chemical structures that are amino acid residue specific as well as structures that are amino acid residue unspecific. Depending on the target protein it may be desired to target specific amino acid residues to obtain a high yield of the desired product.

The reactive end (or group) will differ depending on which amino acid residue it should target.

As demonstrated in the Examples conjugation with thiols can be obtained using various cysteine or thiol-reactive ends, while other reactive groups are suitable for conjugation to alternative amino acid residues. The resulting conjugate includes the radical of the reactive end as part of the linker. The resulting radical of the reactive end will be covalently bond to the amino acid residue of attachment. The radical of the reactive end may be referred to as -RR-. The -Linker- moiety of the conjugates may thus be further described by specifying the reactive end radical(s) (-Linker-RR).

The N-terminal amino acid may be targeted by an aldehyde or ketone. In one embodiment an N-terminal reactive end comprises —CHO. Lys residues may be target by i.e. a 2,5-dioxopyrrolidin-1-yl.

In one embodiment the reactive end comprises a Lys reactive end, such as a dioxopyrrolidin. A Gln residue may be targeted by a two-step process described in WO2005070468 using transglutaminase to create and aldehyde that is reactive with an amine or hydroxyl amine. In one embodiment the reactive end comprises an aldehyde or ketone. A Ser residue may be oxidised using sodium periodate (NaIO$_4$) to an aldehyde (glyoxyl) which can be target by an amine under reductive amination conditions. A Lys residue may likewise be suitable for a reveres transglutaminase reaction as described in WO2009027369.

In order to describe the linker in further details R1, R2 etc. may be used to describe the individual reactive ends.

In one embodiment the individual reactive ends are selected from C-term, N-term, Gln, Lys, Ser or Cys reactive ends. In one embodiment R1, R2 etc. is an N-terminal reactive end. In one embodiment R1, R2 etc. is a Gln reactive end. In one embodiment R1, R2 etc. is a Lys reactive end. In one embodiment R1, R2 etc. is a Ser reactive end. In one embodiment R1, R2 etc. is a Cys reactive end.

In order to obtain regio-selectivity it may be preferred that the reactive ends differ, such as providing linkers having one Lys reactive end and one Cys reactive ends. If two Cys reactive ends are used the reactivity may be controlled as described below for bivalent and trivalent linkers.

The linkers according to the invention may comprise one or more thiol or cysteine reactive ends separated by a spacer. The reactive ends of the linker may in an embodiment be referred to as Cys or thiol reactive ends. It is preferred that the reactive end is capable of reacting with the thiol independent on the position of the thiol. In one embodiment the thiol reactive end enables linkage to an N-terminal cysteine. In one embodiment the thiol reactive end enables linkage to a C-terminal cysteine. In one preferred embodiment the thiol reactive end enables linkage to an internal amino acid residues e.g. a free cysteine as described herein.

The skilled person is aware of several routes enabling coupling to cysteines. Two key reactive ends are alpha-substituted acetamides (e.g., alpha-halogen acetamides) with a suitable leaving group (LG-acetamide) and alpha-beta-unsaturated carbonyl compounds (such as e.g., maleimides). The reactive end may thus be such as a maleimide or a LG-acetamide, wherein the leaving group is e.g. a sulfonic ester (such as tosylate or mesylate) or a halide (forming an alpha halo-acetamide). The halogen may be Cl, Br or I. In an alternative embodiment the leaving (LG) group may be an alternative molecule providing same functionality.

A Cys reactive end (or thiol-reactive end) is thus a chemical entity that allows conjugation to cysteine residues in a protein of interest. Examples of Cys reactive end groups are such as a terminal aldehyde, a pyrrolidin-2,5-dione (2,5-Pyrroledione)(also referred to as maleimide) and a leaving group-acetamide (such as a halo-acetamide).

In one embodiment the Cys reactive end comprises -pyrrolidin-2,5-dione.

In one embodiment the Cys reactive end comprises —NHC(=O)—CH$_2$-pyrrolidin-2,5-dione.

In one embodiment the Cys reactive end comprises a leaving group, such as a halogen, exemplified by Bromide, Chloride or Iodide.

In one embodiment the Cys reactive end comprises a halo-acetamide. For halo-acetamides, the reactive end —NH—C(=O)—CH$_2$—I is more reactive than —NH—C(=O)—CH$_2$—Br which again is more reactive than —NH—C(=O)—CH$_2$—Cl.

The halo-acetamide is reactive towards Cys residues and may therefore be used for coupling of two proteins each including a free Cys either a wt residue or more likely a variant amino acid residue introduced for the purpose of conjugation.

As described further herein below, the reactive ends of the linker may comprise leaving group(s) which are different and the linker may thus have the overall structure: LG$^1$-Linker-LG$^2$. The leaving groups are in one embodiment halogens and in particular halogens with different reactivity.

When the leaving group(s) are included as part of a halo-acetamide the reactivity is I>Br>>Cl.

In one embodiment the invention relates to a linker of the structure:

$LG^1$-Linker-$LG^2$, wherein both ends are Cys reactive and the reactivity of $LG^1$ and $LG^2$ are different. The moiety between the reactive ends is here called Spacer. The Spacer may consist of one or more spacer elements as described herein below. The Spacer elements may be linked by peptide bonds. When the Cys reactive end is a halo-acetamide a peptide bond (—C(=O)—NH—/—NH—C(=O)—) is comprised by the reactive end.

In one embodiment the linker has the structure:

Halo$^1$-CH$_2$—C(=O)—NH-Spacer-NH—C(=O)—CH$_2$-Halo$^2$,

Cl—CH$_2$—C(=O)—NH-Spacer-NH—C(=O)—CH$_2$—Br or

Br—CH$_2$—C(=O)—NH-Spacer-NH—C(=O)—CH$_2$—Cl

Trivalent Linker

As described above, the present invention covers linkage of a protein with an Fc-domain. Notably an Fc domain consists of two polypeptides that are usually held together by covalent and non-covalent bonds including also inter-polypeptide disulfide bond(s). Covalent linkage using a traditional bivalent linker the linkage would go from the protein to only one of the Fc polypeptides. Using a trivalent linker according to the present invention a protein conjugate where both of the two Fc polypeptide chains are linked to the protein can be obtained. Clearly, use of such trivalent linkers is not limited to the conjugation of Fc domains.

The trivalent linker may have a structure including a central unit referred to as "U", that is at least a tri-radical The central unit may be any chemical structure that allows for at least three bonds extending from the unit (-U=). The central unit may in one embodiment be and Nitrogen atom (—N=). The central unit may in one embodiment be a tetravalent carbon atom (=C=), in which case the forth "arm" may be —H, —CH$_3$ or any other structure that does not interfere with the linker functionality. The central unit may in one embodiment be a benzene ring.

The trivalent linker structure may comprise three linker arms that may be identical or different. The linker arms each comprise a spacer part (S) and a reactive end (R). The overall structure being:

$$R1-S1-U-S2-R2$$
$$\phantom{R1-S1-U}|$$
$$\phantom{R1-S1-U-}S3-R3$$

wherein

U represents a tri-radical (central unit)

S1, S2 and S3 represent individual spacers and

R1, R2 and R3 represent individual reactive ends (suitable) for conjugation to a protein molecule.

In one embodiment R1, R2 and R3 are not identical. In one embodiment R2 and R3 are identical. In one embodiment R2 and R3 are identical but R1 is different. In one embodiment one or more of the reactive ends R1, R2 and R3 are thiol reactive ends. In one embodiment R2 and R3 are thiol reactive ends. In one embodiment at least R2 and R3 are thiol reactive ends. In one embodiment R2 and R3 are thiol reactive ends while R1 is not a thiol reactive end. In one embodiment R1, R2 and R3 are thiol reactive ends. In one embodiment R1, R2 and R3 have different reactivity towards cysteines.

In one embodiment R2 and R3 are thiol reactive ends and R1 is not a thiol reactive end. In such embodiments R1 may be a reactive end selected from C-term, N-term, Gln, Lys and Ser reactive ends.

In one embodiment the thiol reactive end comprises a maleimide. In one embodiment the thiol reactive end comprise a leaving group (LG), such leaving group may be an inorganic leaving group, such as a halogen exemplified by bromide, chloride or iodide or an organic leaving group exemplified by such as mesylate or tosylate.

In one embodiment the leaving group is a halogen such as bromide, chloride or iodide. In one embodiment one or more of the reactive ends is/are halo-acetamide(s).

In one embodiment R2 and R3 are thiol reactive ends, such as —NH—C(=O)—CH$_2$-LG, providing a linker with the structure:

$$R1-S1-U-S2-NH-C(=O)-CH_2-LG^2$$
$$\phantom{R1-S1-U}|$$
$$\phantom{R1-S1-U-}S3-NH-C(=O)-CH_2-LG^3$$

wherein $LG^2$ and $LG^3$ are leaving groups and R1 is a reactive end and S1, S2 and S3 represent individual spacers as above.

In one embodiment the leaving groups 2 ($LG^2$) and 3 ($LG^3$) are identical, whereas in a further embodiment the leaving groups 2 and 3 are different. Different leaving groups may have different reactivity and enable sequential conjugation.

In one embodiment R1 comprises a thiol reactive end. In on embodiment R1 is a thiol reactive end. In one embodiment the thiol reactive end is a haloacetamide.

In one embodiment R1 comprises a leaving group ($LG^1$), such leaving group may be an inorganic leaving group, such as a halogen exemplified by bromide, chloride or iodide or an organic leaving group such as mesylate or tosylate.

In on embodiment the first linker arm has the structure: $LG^1$-CH$_2$—C(=O)—NH—S1. In one embodiment R1 comprises a leaving group (LG), such as a halogen, such as bromide, chloride or iodide.

In one embodiment R1 is different from R2 and R3. In one embodiment R1 comprises a different leaving group than R2 and R3.

In one embodiment $LG^1$ is different from $LG^2$ and $LG^3$

In order to direct sequential conjugation of the linker arms to the different proteins to be conjugated different reactive ends can be used.

In one embodiment where all arms include a thiol reactive end comprising a LG, the LG's may be different to achieve different reactivity towards the proteins. In one embodiment the reactivity's of the thiol reactive ends are different.

In one embodiment the reactivity of $LG^1$ is higher than the reactivity of $LG^2$ and $LG^3$. In one embodiment the reactivity of $LG^2$ and $LG^3$ is higher than the reactivity of $LG^1$.

The order of reactivity for the haloacetamides is I>Br>>Cl. Thus a reactive end of —NH—C(=O)—CH$_2$—Br will be more reactive than —NH—C(=O)—CH$_2$—Cl and —NH—C(=O)—CH$_2$—I will have even higher reactivity towards (reduced) cysteine residues.

The linkers according to the invention may thus comprise one or more thiol or Cys reactive group. Key examples of Cys reactive groups and reactive end radicals are:

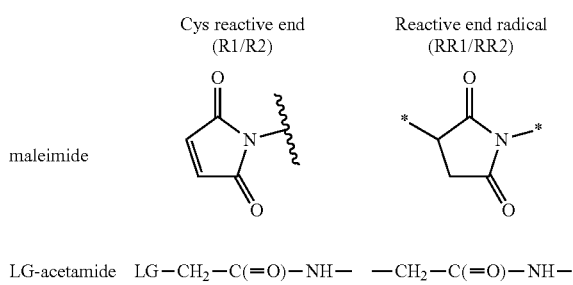

LG-acetamide   LG—CH$_2$—C(=O)—NH—    —CH$_2$—C(=O)—NH—

The zigzag line and N—* indicate the attachment to the rest of the linker while the *- to the left indicates attachment to the —S— of the Cys amino acid residue.

The linker of the invention may further comprise individual spacer segments that link the reactive end with the central unit. The spacer segments are designated S1, S2 and S3. As mentioned above the linkers allows for symmetrical conjugation of an Fc-domain, which is obtained when e.g. R2-S2 and R3-S3 are identical, while the linkage to a protein of interest via the first arm may be different. In other embodiments the conjugates are none-symmetrical and all of R1-S1, R2-S2 and R3-S3 may be different.

The spacers S1, S2 and S3 may comprise different spacer elements. In a situation where protein 2 and 3 are to be in close proximity a short spacer may be used for S2 and S3. A short space could be from 1-10 atoms, such as 2-5 atoms in length counting the number of atom bound in the shortest distance. In one embodiment the short spacer is —(CH$_2$)$_n$—, wherein n is an integer in the range of 1-5. In one embodiment the short spacer is —(CH$_2$)$_n$—, wherein n is an integer in the range of 1-3, such as n=2 and such as n=3 and S2 and S3 are thus—(CH$_2$)$_2$— or —(CH$_2$)$_3$—.

In one embodiment the distance from the central unit is increased by extending one or more of the spacers.

In one embodiment the linker comprises at least one extended spacer. If the distance to the central unit is only to be increase for one of the proteins of the conjugate only one of the spacer should be extended. In one embodiment the extended spacer is S1. An extended spacer is longer that the short spacers exemplified above for S2 and S3. An extended spacer could be from 10-50 atoms, such as 20-30 atoms in length counting the number of atom bound in the shortest distance.

In one embodiment where the central unit comprise a nitrogen (N) one arm of the linker may be linked to the N via an amide bond. In a further embodiment S1 (which connects R1 with the central unit (here N) has a carbonyl (C=O) at the end which may form an amide bond with the nitrogen atom.

In further embodiment the spacers may include one or more amino acid like spacer elements. The spacer elements may be linked by amide bond(s). Such spacer element thus holds an N-terminal and a C-terminal as does an amino acid in a polypeptide. Such spacer elements may be amino acid residues or modified amino acid residues or alternative chemical entities capable of being linked by amide bonds. Examples are glycine, alanine, glutamic acid and gamma-Glu (γ-Glu) as shown in a) through d) below.

The carbonyl end may form an amide bond with the central nitrogen in one of the linker arms.

Alternative amino acid like elements including an additional amino group (instead of the carbonyl-group) as exemplified by e) and f) below may also be used next to the central Nitrogen in one of the linker arms. When coupled hereto and urea/carbamide group is present in the linker structure.

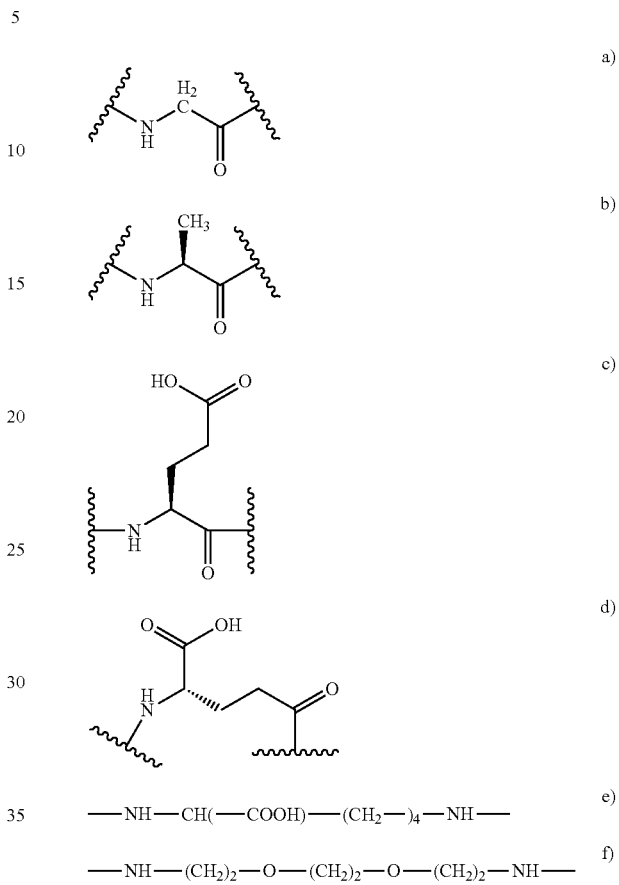

e) —NH—CH(—COOH)—(CH$_2$—)$_4$—NH— f) —NH—(CH$_2$)$_2$—O—(CH$_2$)$_2$—O—(CH$_2$)$_2$—NH—

The glycine spacer element may be extended by including polyethyleneglycol unites.

In a further embodiment, the spacer comprises a polyethylene glycol (PEG) moiety. The PEG moiety being a bi-radical comprising the structure

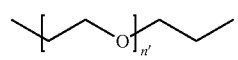

wherein n' is an integer larger than 1. In one such embodiment n' is an integer selected from 2-20. In one such embodiment n' is an integer selected from 2-10 or 2-5. In one embodiment n' is 2.

In one embodiment a PEG moiety may have the structure

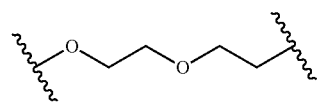 [SMILES: *CCOCCO*]

In one embodiment the PEG moiety is included in an amino acid or amino acid like spacer element as described above.

In one embodiment the spacer element has the formula.

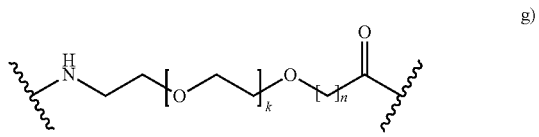

wherein k is an integer in the range of 1-5, and n is an integer in the range of 1-5. In one specific embodiment k=1 and n=1 providing a spacer element.

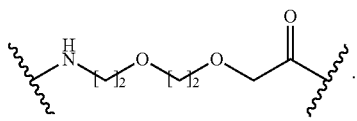

In one embodiment the space element g) is defined by a k=1 and n=1 providing *—NH—(CH$_2$)$_2$—O—(CH$_2$)$_2$—O—CH$_2$—C(=O)—*(e1) which may be referred to as OEG or a di-radical of 8-amino-3,6-dioxaoctanoic acid.

In the structures above the zig-zag lines mark the bond to the spacer, the central unit or the reactive end. In the cases where the spacer links to the reactive end "—NH—" may be considered part of the reactive end. This may be the case in the embodiments described above where the reactive end holds a halo-acetamide.

In one embodiment R1-S1- comprise 3-8 spacer elements linked by amid bonds. In one embodiment R1-S1- comprises 4-6 spacer elements linked by amid bonds.

In one embodiment the structure of the trivalent linker is

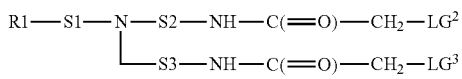

wherein leaving groups LG$^2$ and LG$^3$ are identical.

In one such embodiment R1 is not a thiol reactive end.

In one embodiment the structure of the trivalent liner is

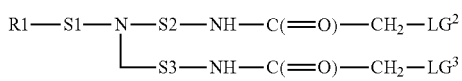

wherein leaving group LG$^2$ and LG$^3$ are identical and R1 is a Ser, Lys, Gln, C-term or N-term reactive end.

In one alternative embodiment all reactive ends are Cys reactive. In one embodiment R2 and R3 are identical and R1 is a different Cys reactive end. Such different reactive ends will allow selected linkage of the proteins. In one embodiment R2 and R3 comprise a halo-acetamide.

In one embodiment LG$^2$ and LG$^3$ are Cl with the linker having the overall structure:

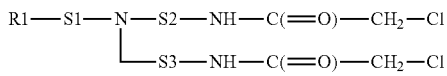

In one embodiment LG$^2$ and LG$^3$ are Br with the linker having the overall structure:

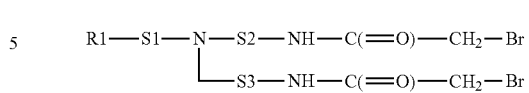

In one embodiment all the reactive ends are halo-acetamides. In one embodiment R1 comprises a halo-acetamide including LG$^1$.

In one embodiment the structure of the trivalent linker is:

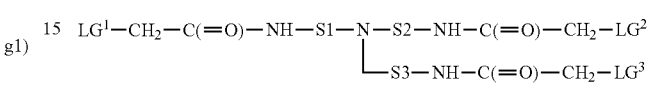

In one embodiment the structure of the trivalent linker is:

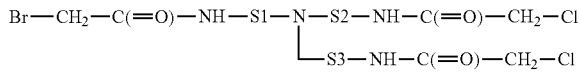

In one embodiment the structure of the trivalent linker is:

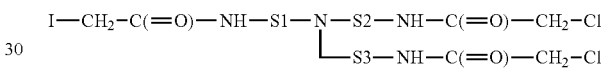

In one embodiment the structure of the trivalent linker is:

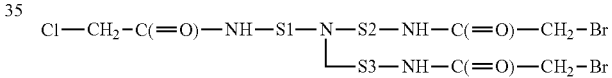

In one embodiment the structure of the trivalent linker is:

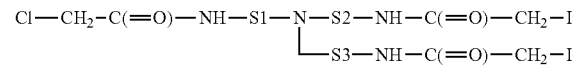

In one embodiment the structure of the trivalent linker is:

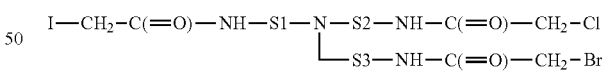

In an embodiment where the 2$^{nd}$ and 3$^{rd}$ arms are identical the linker moiety can be described by the generic structure A-B where A- is the 1$^{st}$ arm and -B comprises the central unit and the 2$^{nd}$ and 3$^{rd}$ arms. If similar structures are used as above A is R1-S1- and B is —N—(S2-R2)$_2$.

The overall size of the linker may thus vary, but will usually be relatively small as seen by the examples herein. When measuring the size of the linker only the linkerpart remaining in the conjugate is included meaning that the leaving groups are not include.

In one embodiment the size of the linker is below 10 kDa, such as below 5 kDa, such as below 2 kDa, such as below 1 kDa, such as below 500 kDa. In one embodiment the linker is from 250 Da to 20 kDa, such as from 500 Da to 10 kDa.

In one embodiment the linker is from 500-2000 Da, such as from 600-1500 da, such as 700-100 da.

The length of the full linker of a conjugate may be estimated by counting the number of atoms in the shortest distance between two proteins. In cases where two arms are identical the length is the longest distance e.g. from Protein$_1$ to Protein) in the examples where $2^{nd}$ and $3^{rd}$ arms are identical and $1^{st}$ arm longest. When the central atom is N, this counts one atom while a benzene ring as central unit counts 3 atoms if arms are positioned symmetrically. As leaving groups are not part of the final conjugate such are not counted only the reactive end radical.

In one embodiment the linker is 5-200 atoms in length such as 8-150 atoms or 10 to 100 atoms or in length. In a further embodiment the linker is 10-80 atoms in length. In a further embodiment the linker is 10-60 atoms in length. In a further embodiment the linker is 10-40 atoms in length, such as 15-40 or such as 20-35 atoms.

Examples of trivalent linkers according to the invention are provided in table 1 here below.

TABLE 1

Examples of Trivalent linkers.
Structure and Name

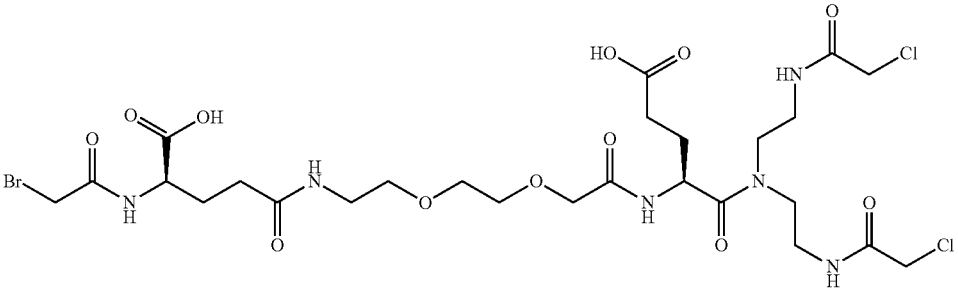 [SMILES: O=C(O)CC[C@H](NC(=O)COCCOCCNC(=O)CC[C@@H](NC(=O)CBr)C(=O)O)C(=O)N(CCNC(=O)CCl)CCNC(=O)CCl]

(S)-4-(2-{2-[((S)-1-{Bis-[2-(2-chloro-acetylamino)-ethyl]-carbamoyl}-3-carboxy-propylcarbamoyl)-methoxy]-ethoxy}-ethylcarbamoyl)-2-(2-bromo-acetylamino)-butyric acid

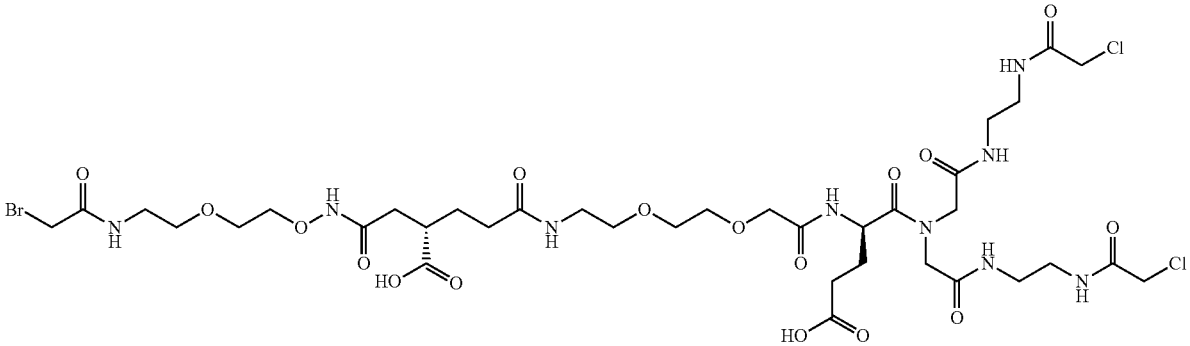

(2R)-5-[2-[2-[2-[[(1S)-1-[bis[2-[2-[(2-chloroacetyl)amino]ethylamino]-2-oxo-ethyl]carbamoyl]-3-carboxy-propyl]amino]-2-oxo-ethoxy]ethoxy]ethylamino]-2-[[2-[2-[2-[(2-bromoacetyl)amino]ethoxy]ethoxy]acetyl]amino]-5-oxo-pentanoic acid

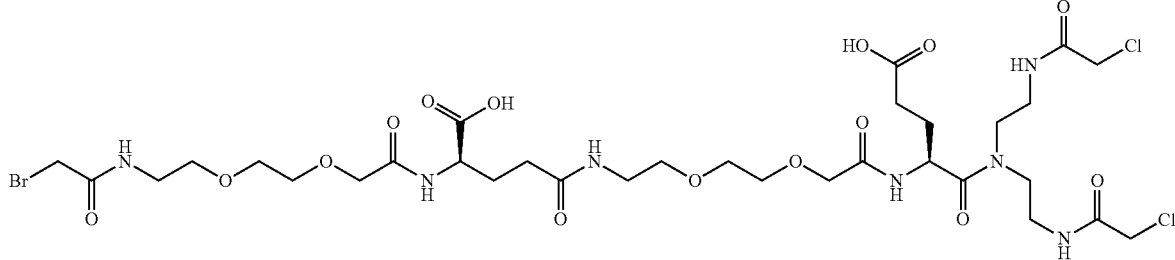 [SMILES: O=C(O)CC[C@H](NC(=O)COCCOCCNC(=O)CC[C@@H](NC(=O)COCCOCCNC(=O)CBr)C(=O)O)C(=O)N(CCNC(=O)CCl)CCNC(=O)CCl]

(4S,18S)-4-(bis(2-(2-Chloroacetamido)ethyl)carbamoyl)-18-(2-(2-(2-(2-bromoacetamido)ethoxy)ethoxy)acetamido)-6,15-dioxo-8,11-dioxa-5,14-diazanonadecanedioic acid TABLE 1-continued Examples of Trivalent linkers.
Structure and Name

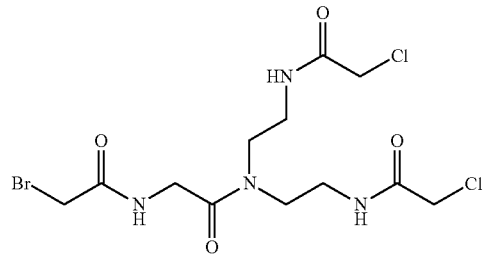 [SMILES: O=C(CCl)NCCN(CCNC(=O)CCl)C(=O)CNC(=O)CBr]

2-(2-bromoacetamido)-N,N-bis(2-(2-chloroacetamido)ethyl)acetamide

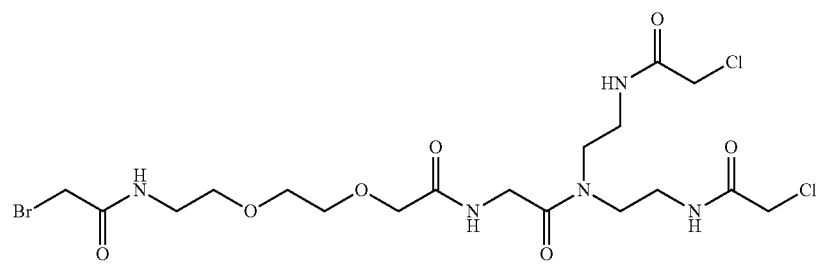

2-(2-(2-(2-(2-bromoacetamido)ethoxy)ethoxy)acetamido)-N,N-bis(2-(2-chloroacetamido)ethyl)acetamide

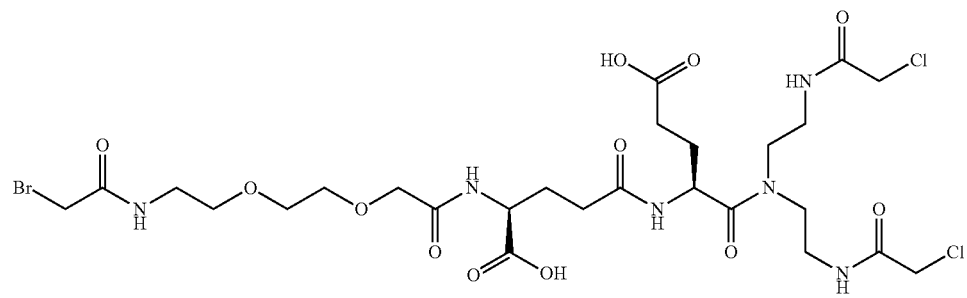

(13R,18S)-18-(bis(2-(2-Chloroacetamido)ethyl)carbamoyl)-1-bromo-13-carboxy-2,11,16-trioxo-6,9-dioxa-3,12,17-triazahenicosan-21-oic acid

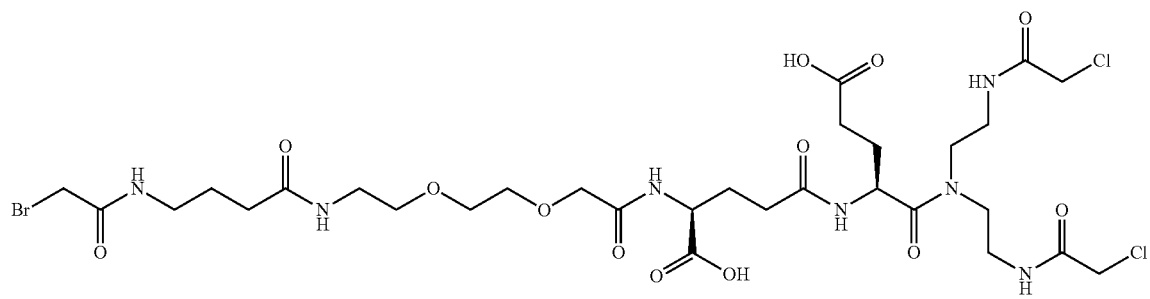

(18R,23S)-23-(Bis(2-(2-chloroacetamido)ethyl)carbamoyl)-1-bromo-18-carboxy-2,7,16,21-tetraoxo-11,14-dioxa-3,8,17,22-tetraazahexacosan-26-oic acid TABLE 1-continued Examples of Trivalent linkers.
Structure and Name

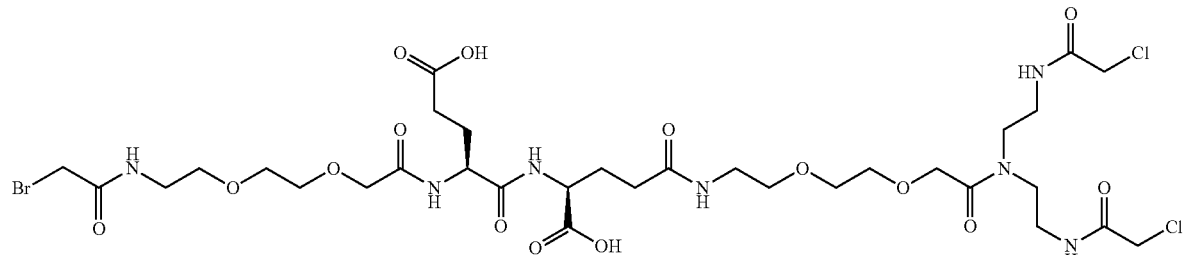

(R)-4-{2-[2-({Bis-[2-(2-chloro-acetylamino)-ethyl]-carbamoyl}-methoxy)-ethoxy]-
thylcarbamoyl}-2-[(S)-2-(2-{2-[2-(2-bromo-acetylamino)-ethoxy]-ethoxy}-
acetylamino)-4-carboxy-butyrylamino]-butyric acid

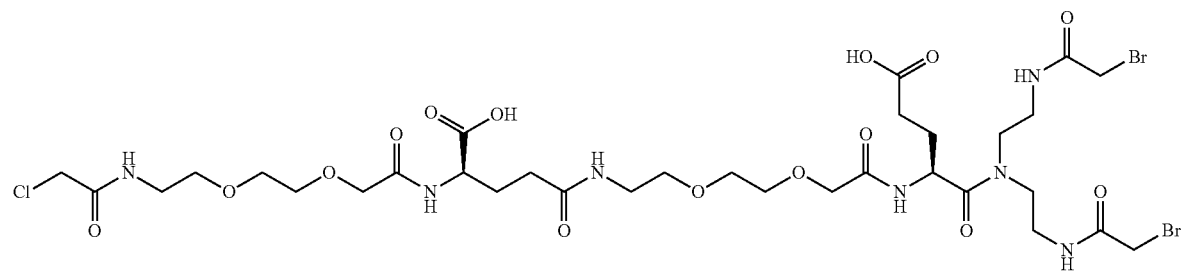

(4S,18S)-4-(bis(2-(2-Bromoacetamido)ethyl)carbamoyl)-18-(2-(2-(2-(2-
chloroacetamido)ethoxy)ethoxy)acetamido)-6,15-dioxo-8,11-dioxa-5,14
diazanonadecanedioic acid

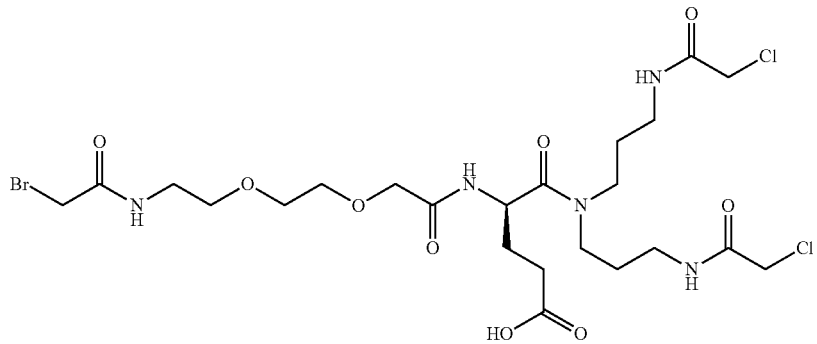

(4S)-5-[bis[3-[(2-chloroacetyl)amino]propyl]amino]-4-[[2-[2-[2-[(2-
bromoacetyl)amino]ethoxy]ethoxy]acetyl]amino]-5-oxo-pentanoic acid

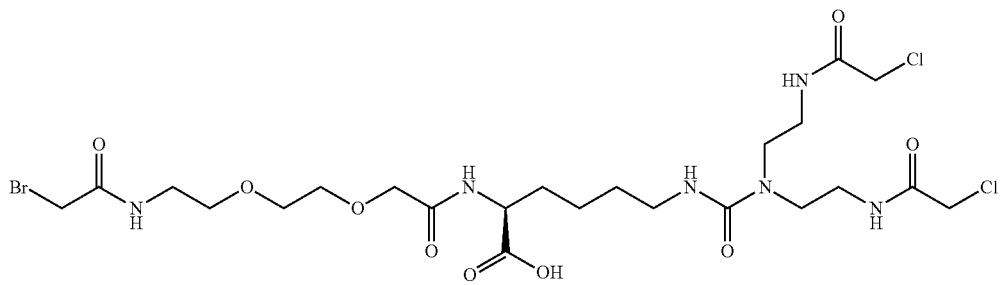

(2R)-6-[bis[2-[(2-chloroacetyl)amino]ethyl]carbamoylamino]-2-[[2-[2-[2-[(2-
bromoacetyl)amino]ethoxy]ethoxy]acetyl]amino]hexanoic acid TABLE 1-continued Examples of Trivalent linkers.
Structure and Name

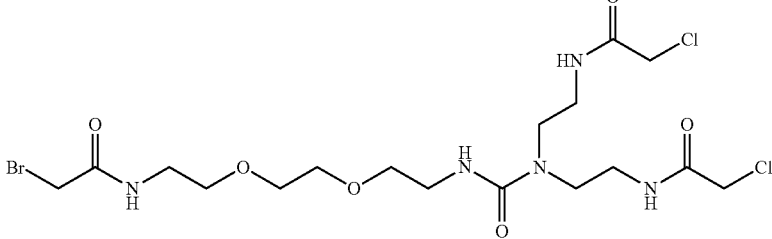

N-[2-[2-[2-[2-[(2-bromoacetyl)amino]ethoxy]ethoxy]ethylcarbamoyl-[2-[(2-
chloroacetyl)amino]ethyl]amino]ethyl]-2-chloro-acetamide

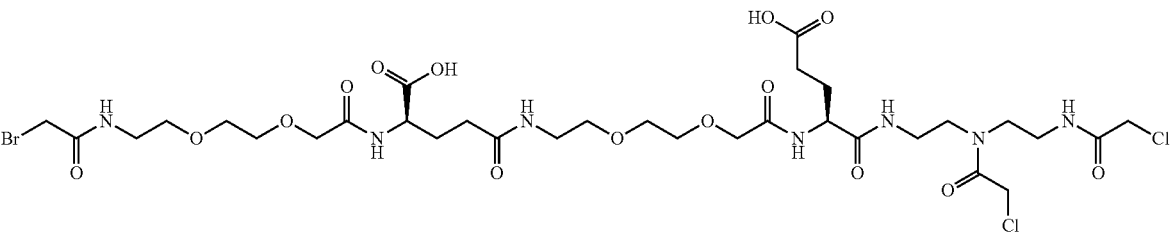

(2R)-2-[[2-[2-[2-[(2-bromoacetyl)amino]ethoxy]ethoxy]acetyl]amino]-5-[2-[2-[2-
[[(1S)-3-carboxy-1-[2-[(2-chloroacetyl)-[2-[(2-
chloroacetyl)amino]ethyl]amino]ethylcarbamoyl]propyl]amino]-2-oxo-
ethoxy]ethoxy]ethylamino]-5-oxo-pentanoic acid Protein Conjugates The protein conjugates of the invention will thus comprise 2 or more individual polypeptides (Protein$_1$, Protein$_2$ and/or Protein$_3$) covalently bound to each other via the linker moiety. In one embodiment Protein$_1$, Protein$_2$ and Protein$_3$ are individual polypeptides. In one embodiment the individual polypeptides may be identical or two of Protein$_1$, Protein$_2$ and Protein$_3$ may be identical. The individual polypeptides thus have each an N-terminal and C-terminal amino acid residue. That said the individual polypeptides may additionally be attached to each other or even a further polypeptide/protein via e.g. disulfide bonds.

As the proteins are bound to each other via the linker, the linker moiety will be part of all such compound including intermediates also covered by the present invention.

In one embodiment the conjugate of the invention have the structure

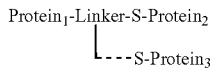

wherein
Linker is a chemical moiety
S is a sulfur atom and
Protein$_1$ is covalently linked to Protein$_2$ and Protein$_3$ via said linker and sulfur atoms.

In one embodiment the sulfur atom is part of a thioether e.g. the bonds from the sulfur atoms goes to two individual carbon atoms C—S—C where the carbon atoms may be part of any organic structure. The most common thioether is —CH$_2$—S—CH$_2$— where in the present case one CH2 group stems from the protein linked to the linker and most frequently from the cysteine residue providing the sulfur atom for the conjugation.

In one embodiment the sulfur atom of the conjugate is not part of a disulfide bond.

In one embodiment where -S2-R2 is identical with -S3-R3, and two copies of Protein$_2$ is to be conjugated with Protein$_1$, the structure of the linker may be described by -A-B= and the resulting conjugate is of the structure Protein$_1$-A-B-(Protein$_2$)$_2$. When B is consider a linker arm, the structure may be Protein$_1$-A-(B-Protein$_2$)$_2$ Further examples of compounds of the invention are described here in below when addressing the method for preparation of the conjugates.

Fc Conjugates

In one embodiment Protein$_2$ and Protein$_3$ is/are the same Fc polypeptide, which together forms an Fc-domain. As described herein the linkage to an Fc polypeptide can be obtained by reducing a disulfide bridge of the hinge region and linking each of the cysteines to the linker, such as via linker arms 2 and 3. The 3$^{rd}$ linker arm (here linker arm 1) is either prior or later conjugated to a Protein$_1$ of interest. As described in the section on preparation of protein conjugates the conjugates may have the form of:

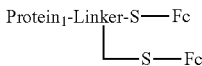

In an embodiment where the reactive ends 2 and 3 are haloacetamides the conjugate has the form:

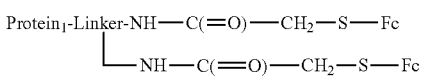

In one embodiment the conjugate has the structure:

Protein$_1$-RR1-S1-U-[S2-NH—C(=O)—CH$_2$—S-Fc]$_2$ wherein
RR1 represents a reactive end radical,
U represents a central unit,
S1 and S2 represent individual spacers and
Fc is an Fc polypeptide.

If the alternative description above is used it follows that the Fc conjugates can be described by: Protein$_1$-A-(B-Fc)$_2$.

If the Sulfur atom for linkage to Fc is include the structure is:

Protein$_1$-A-(B-S-Fc)$_2$ and including the thioether the structure is Protein$_1$-A-(B-CH$_2$—S-Fc)$_2$ or Protein$_1$-A-(B-CH$_2$-S—CH$_2$-Fc)$_2$ if the —CH$_2$— of the cysteine of the Fc is shown as well. When the linkage is obtained by a thiol and haloacetamide coupling, B thus includes at least the —NH—C(=O)—CH$_2$— element remaining from the thiol and haloacetamide reaction providing:

Protein$_1$-A-(B'-NH—C(=O)—CH$_2$—S-Fc)$_2$

It appears that S2 and B' are then similar in the sense that they symbolize the remaining part of the linker arms. In a preferred embodiment as S2 or B' is —CH$_2$—CH$_2$— providing a conjugate structure of:

Protein$_1$-A-(CH$_2$—CH$_2$—NH—C(=O)—CH$_2$—S-Fc)$_2$ wherein A is the linker unit connecting to Protein$_1$ which, as has been described elsewhere in the application, comprise a central unit (with options for at least three bonds) and a suitable spacer and a reactive end radical providing the linkage to Protein$_1$.

Growth Hormone Fc Conjugates

In an aspect the present invention relates to growth hormone Fc conjugates, such GH conjugates preferably has increased in vivo half-life ($T_{1/2}$) compared to wild type human growth hormone. In addition the growth hormone Fc conjugates preferably maintain the therapeutic capabilities of human growth hormone which can be assayed in vitro by testing receptor binding and the activity in a BAF assay as described in Assay 1 and 2. Animal models may be used to further evaluate the therapeutic potential of growth hormone Fc conjugates (Assay 3-5).

Examples of growth hormone conjugates according to the invention are included in table 3 here below.

TABLE 3

GH-Fc compounds of example 2

| # Compound | Structure |
|---|---|
| 1 | hGH-Fc conjugate |
| 2 | hGH-Fc conjugate |

TABLE 3-continued
GH-Fc compounds of example 2
| # Compound | Structure |
|---|---|
| 3 | 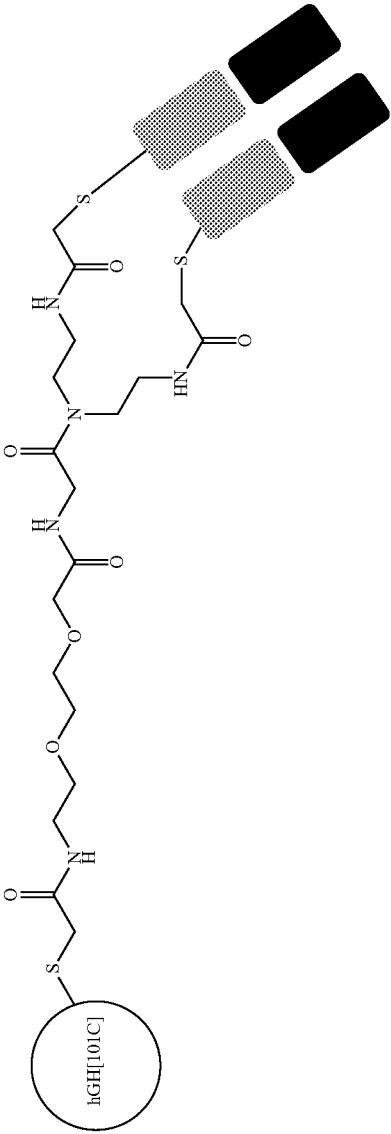 |
| 4 | 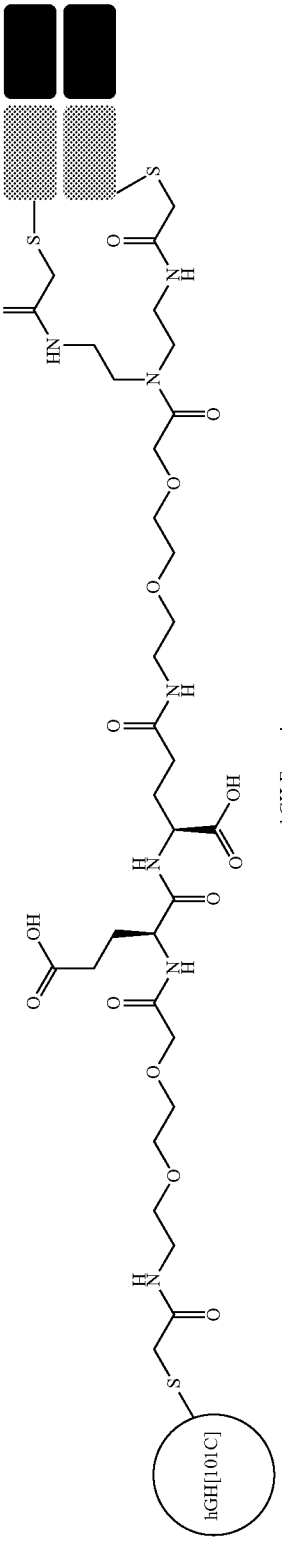 |

TABLE 3-continued
GH-Fc compounds of example 2
| # Compound | Structure |
|---|---|
| 5 |  hGH-Fc conjugate |

Pharmaceutical Compositions

A protein conjugate according to the invention may be formulated as a pharmaceutical composition.

The formulation may further comprise a suitable buffer, a preservative, a tonicity agent, a chelating agent, a stabilizer, and/or a surfactant, as well as various combinations thereof.

The use of preservatives, isotonic agents, chelating agents, stabilizers and surfactants in pharmaceutical compositions is well-known to the skilled person. The formulations may be prepared using standard procedures know in the art. Reference may be made to Remington: The Science and Practice of Pharmacy, 19$^{th}$ edition, 1995.

In one embodiment of the invention the pharmaceutical composition is a liquid formulation. In one embodiment of the invention the pharmaceutical composition is an aqueous composition, i.e. a composition where the components are dissolved or suspended in water. Such composition is typically a solution or a suspension. If the composition comprises components which cannot be dissolved in water the composition may be an emulsion of two liquids, frequently water and oil or a fatty acid based liquid. In another embodiment the pharmaceutical composition is a freeze-dried composition, whereto the physician or the patient adds solvents and/or diluents prior to use.

In one embodiment the composition of the invention has a pH of 5.0-8.5, such as 6.0-8.5, such as 6.0-8.2, such as 6.0-8.0, such as 7.0-8.5, such as 7.0-8.0, such as 7.5-8.0, such as 6.0-7.5, such as 6.2-7.5, such as 6.4-7.2 such as 6.5-7.0, such as 6.6-7.0. The pH may also be 6.6-6.9 or 6.7-6.9. In further embodiments the pH of the composition is 6.6, 6.7, 6.8, 6.9 or 7.0.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.

In one embodiment the pharmaceutical composition does not include glycine. In one embodiment composition comprises histidine as buffer.

In one embodiment the pharmaceutical composition comprises a surfactant, such as a polyoxypropylene-polyoxyethylene block polymer. In one embodiment the surfactant is selected from non-ionic surfactants, such as poloxamers including Pluronic® F68, poloxamer 188 and 407 and Triton X-100. In one embodiment the surfactant is selected from polyoxyethylene and polyethylene derivatives such as alkylated and alkoxylated derivatives (tweens, e.g. Tween-20, Tween-40, Tween-80 and Brij-35). In one embodiment the surfactant is polysorbate 80.

In a further embodiment the composition comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(p-chlorophenoxy)propane-1,2-diol) or mixtures thereof.

Methods of Treatment

Protein conjugates as described herein may be useful in the treatment of various diseases and disorders depending on the combined therapeutic effect of the proteins of the conjugate.

It is will know that growth hormone compounds are suitable for treatment of growth hormone deficiencies. Basically a pharmaceutical composition according to the invention comprising a growth hormone protein conjugated may be for use in treatment of any disease or disorder where the patient will benefit from an increase in circulating growth hormone activity. In current treatments a growth hormone protein is administered. As an alternative growth hormone variants or compounds may be administered to provide growth hormone activity. An aspect of the invention is the growth hormone conjugate for use in a method of treatment.

An aspect of the invention relates to the use of the growth hormone conjugate for the manufacture of a medicament for treatment, in particular treatment of growth hormone deficiency in children and/or adults or other diseases or states where the patient benefit from an increased level of growth hormone as described herein.

The invention further relates to the aspects of preparation of a pharmaceutical composition according to the invention for use in a method of treatment as well as the pharmaceutical composition for use in a method of treatment comprising a protein conjugate including growth hormone conjugates.

In such embodiments, the pharmaceutical composition according to the invention is for use in a method of treatment or prevention of growth hormone deficiency in children and/or adults. Other diseases or disorders where an increased concentration of circulating growth hormone may be helpful may also be treated or prevented using the pharmaceutical composition of the invention. In one embodiment the pharmaceutical compositions of the invention is for use in a method for treating diseases or states where a benefit from an increase in the amount of circulating growth hormone is observed. Such diseases or states include growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or 1st toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Chron's disease; IBD, UC, impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucocorticoid treatment in children. Growth hormones have also been used for acceleration of the healing of muscle tissue, nervous tissue or wounds; the acceleration or improvement of blood flow to damaged tissue; or the decrease of infection rate in damaged tissue.

In one embodiment, the growth hormone conjugates and compositions hereof is for treatment of GHD in children, GHD in adults (AGHD), Turner syndrome (TS), Noonan syndrome, Idiopathic short stature (ISS), Small for gestational age (SGA), Prader-Willi syndrome (PWS), Chronic renal insufficiency (CRI), Skeletal dysplasia, SHOX deficiency, AIDS wasting, HIV associated lipdystrophy (HARS), Short bowel syndrome optionally including, steroid dependent disease, cystic fibrosis and fibromyalgia.

In one embodiment the growth hormone conjugate or composition is for use in the manufacture of a pharmaceutical composition as described herein.

In one embodiment, the present invention relates to a method of treating diseases or states mentioned above, wherein the activity of the pharmaceutical composition according to the invention is useful for treating said diseases or states. The administering of the pharmaceutical composition e.g. the growth hormone conjugate resulting in a therapeutic benefit associated with an increase in the amount of circulating growth hormone activity in the patient. In an embodiment said method comprises, administering to a patient an effective amount of the pharmaceutical composition comprising a growth hormone conjugate thereby ameliorating the symptoms of said patient.

In one embodiment, the present invention relates to a method comprising administration to a patient in need thereof an effective amount of a therapeutically effective amount of a pharmaceutical composition according to the invention. The present invention thus provides a method for treating these diseases or states, the method comprising administering to a patient in need thereof a therapeutically effective amount of a growth hormone variant or compound in a pharmaceutical composition according to the present invention.

A "therapeutically effective amount" of a compound of the invention as used herein means an amount sufficient to cure, alleviate or partially arrest the clinical manifestations of a given disease and its complications. An amount adequate to accomplish this is defined as "therapeutically effective amount".

Effective amounts for each purpose will depend on e.g. the severity of the disease or injury as well as the weight, sex, age and general state of the subject.

As described herein the growth hormone variant or compound of the pharmaceutical composition may have an extended half-life aimed at increasing the exposure in the patient to the compound after each dosage and the administration regime of the pharmaceutical composition should be adjusted to reach an effective exposure.

Method for Preparation of Protein Conjugates

An aspect of the invention relates to a method for preparing protein conjugates as described herein. The proteins to be conjugated (protein$_1$, protein$_2$ and optional protein$_3$) and the linker are produced separately and coupled together in a suitable reaction.

Preparation of Proteins

Depending on protein of interest various sources are available to the skilled person. The protein may be produced by recombinant only by heterologous expression in a suitable host, such as E. coli, yeast or mammalian cell (Molecular Cloning: A Laboratory Manual by Joseph Sambrook, E. F. Fritsch and J. Sambrook (Author).

An example of GH preparation is provide in the Examples section herein and variation hereof can be performed as desired by the skilled person.

The application holds examples with Fc-domains. Fc-domains may be obtained from full length antibodies isolated from humans and other animals or may be produced recombinant and obtained from transformed mammalian cells or microorganisms. Multiple technologies to obtain Fc-domains are known in the art.

An Fc-domain can be produced from a full length antibody by digestion with a proteolytic enzyme such as papain or pepsine. Protein A affinity chromatography and DEAE anion-exchange chromatography can be used to separate the resulting Fab and F(ab')$_2$ from the Fc-domain. Based on SEC-HPLC analysis, purity of Fc-fragment can be determined.

When recombinant methods are used the desired polypeptide can be expressed and the Fc domain subsequently purified. In one embodiment the Fc-domain is a human-derived Fc-domain, such as a human IgG Fc-domain obtained from transformed microorganisms or mammalian cells.

In addition, the Fc-fragment of the present invention may be in the form of having native sugar chains, increased sugar chains compared to a native form or decreased sugar chains compared to the native form, or may be in an aglycosylated form. The increase, decrease or removal of sugar chains of the Fc-fragment may be achieved by methods common in the art, such as a chemical method, an enzymatic method and a genetic engineering method using a microorganism such as E. coli.

An Fc-fragment from E. coli which will be aglycosylated will have diminished or weak binding to Fc gamma receptors I, IIa, IIb, IIIa, respectively, which has the advantage of low ADCC and CDC. Preferably is an aglycosylated hIgG4 Fc-fragment which naturally does not have binding to Fc gamma receptor III.

Sulfur Atoms and Free Cysteine.

As described herein above the linker is covalently bond to one or more proteins via a sulfur atom. The sulfur atom(s) is in an embodiment derived from protein thiol(s).

The most common source of protein thiol is the amino acid cysteine. Cysteines may be engage in disulfide bonds and it may be preferred that the cysteine supplying the thiol is not usually engaged in disulfide bonds. Alternatively, a disulfide bond may be reduced providing two sulfur atoms available for conjugation.

In one embodiment the sulfur atom is derived from a thiol of a cysteine amino acid present in the protein of the conjugate. As the protein conjugate may comprise one or more sulfur atoms, the sulfur atoms may be derived from one or more protein cysteines. A protein cysteine is thus a cysteine residue of a polypeptide of the protein.

In one embodiment the cysteine may be a wild type residue, while in other embodiment the cysteine may be a variant cysteine, such as an amino acid substitution of a wild-type residue. As multiple Cys may be engage in the conjugate some —S— may be from a wt Cys while others may be a variant Cys.

In one embodiment the invention relates to a conjugate according to any of the previous embodiments, wherein one or more of the protein cysteines are variant amino acid residues.

The method described herein is suitable for preparing protein conjugates wherein at least one of the proteins to be conjugated includes a free cysteine. A free cysteine (Cys) is a cysteine residue available for conjugation via a thiol reactive linker. A free Cys is usually a cysteine residue that does not engage in intra protein disulfide bonds. As described herein above for human growth hormone a free Cys maybe generated by recombination introducing an amino acid in a suitable place in a protein of interest. Usually the amino acid insertion will be a substitution of a dispensable amino acid although a Cys could also be introduce as an additional amino acid.

Frequently the free cysteine need to be liberated prior to the conjugation reaction as proteins with a free Cys may form mixed disulfide with other sulfur molecules usually small organic molecules present in the cell extract when the protein is produced and purified.

Free cysteines may also be generated by reducing an existing disulfide bond which will make available two free cysteines. In one embodiment two equivalent cysteines may be generated by reducing an Fc-domain including at least one disulfide bond between the two polypeptides of the Fc-domain. In one embodiment an Fc-domain with a single disulfide bond between the two Fc polypeptides is prepared. In one embodiment the Fc-domain comprise a single disulfide bond in the hinge region of the Fc-domain. As illustrated by example 2, such a molecule can be linked with two arms of a trivalent linker using the method described herein. The resulting protein conjugation (or conjugate intermediate) will have a symmetric linkage with the Fc-domain and a third arm available for conjugation with a second protein. As described below the order of conjugation may be varied.

Preparation of Linker

The linkers of the invention may be produced by standard chemical technologies and multiple examples are included herein.

Reaction Schemes for Protein Conjugates

Depending on proteins used in the conjugation and the individual linker to be use various methods may be applied and it is foreseen that the skilled person is capable of adjusting the methods as set out herein for any specific needs without deviating from the concept of the invention.

The proteins to be conjugated and the linker is prepared and purified separately.

An aspect of the invention relates to a method for coupling of at least two proteins. A sequential reaction with two proteins is obtained by use of a linker with different reactive ends. In an embodiment where both proteins include a free cysteine such proteins are coupled together using a linker with two thiol reactive ends.

The method is further exemplified using a linker with halo-acetamides as reactive ends as describe in relation to the linkers.

The invention in an embodiment relates to a method for preparation of a protein conjugate, wherein Protein$_1$-SH and Protein$_2$-SH are coupled together obtaining a protein conjugate of Formula II Protein$_1$-S—CH$_2$—C(=O)—NH-Linker-NH—C(=O)—CH$_2$—S-Protein$_2$  Formula II using a thiol reactive linker:

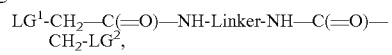

wherein LG$^1$ has a higher reactivity than LG$^2$,
the method comprising the steps of:
 a) reacting Protein$_1$-SH with —NH—C(=O)—CH$_2$-LG$^1$ of the linker
 b) obtaining a conjugate intermediate: Protein$_1$-S—CH$_2$—C(=O)—NH-Linker-NH—C(=O)—CH$_2$-LG$^2$
 c) performing a leaving group exchange reaction increasing the reactivity of LG$^2$.
 d) reacting the intermediate of c) with Protein$_2$-SH
 e) obtaining the protein conjugate.

In case only one Protein$_2$ includes a free cysteine Protein$_1$ may be coupled by an alternative route to provide an intermediate having the structure: Protein$_1$-Linker-NH—C(=O)—CH$_2$-LG.

The method steps c), d) and e) may still be used in a slightly modified method where the conjugation of step a) is performed using an intermediate having the structure: Protein$_1$-Linker-NH—C(=O)—CH$_2$-LG In one embodiment the invention relates to method for preparing a protein conjugate wherein Protein$_1$-Linker-NH—C(=O)—CH$_2$-LG$^2$ and Protein$_2$-SH are coupled together obtaining a protein conjugate of Protein$_1$-Linker-NH—C(=O)—CH$_2$—S-Protein$_2$  Formula I:

wherein LG$^2$ is a leaving group of low reactivity,
the method comprising the steps of
 b) obtaining an conjugate intermediate: Protein$_1$-Linker-NH—C(=O)—CH$_2$-LG$^2$
 c) performing a leaving group exchange reaction increasing the reactivity of LG$^2$.
 d) reacting the intermediate obtained by c) with Protein$_2$-SH
 e) obtaining the protein conjugate.

The leaving group exchange reaction may be performed as an aqueous Finkelstein halogen exchange reaction whereby the reactivity of the leaving group is increased.

In one embodiment LG$^2$ is Cl. In such an embodiment —NH—C(=O)—CH$_2$—Cl is transformed to —NH—C(=O)—CH$_2$—I in step c) which is subsequently reacted with Protein$_2$-SH to obtain the protein conjugate. In this way the first intermediate can be prepared with LG$^2$ in a rather in-active form.

In one embodiment LG$^1$ is Br and LG$^2$ is Cl. As Br-acetamide is more reactive than Cl-acetamide the leaving group will determine the order of conjugation and the subsequent activation changing LG$^2$ from Cl to I will ensure that the linker end of the second intermediate is reactive with Protein$_2$.

The invention also relates to coupling of more than two proteins such as three proteins exemplified herein by the GH and Fc conjugations of Example 2.

In one embodiment the method is for preparation of a protein conjugate, wherein Protein$_1$-SH and two copies of Protein$_2$-SH are coupled together obtaining a protein conjugate of Formula IV.

In one embodiment the invention relates to method for preparing a protein conjugate wherein Protein$_1$-SH and 2×(Protein$_2$-SH) are coupled together obtaining a protein conjugate of

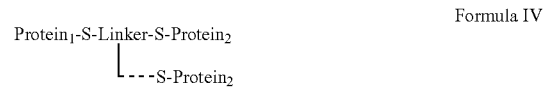

using a thiol reactive linker:

wherein $LG^1$ has a higher reactivity than $LG^2$,
the method comprising the steps of:
a) reacting $Protein_1$-SH with —NH—C(=O)—CH$_2$-$LG^1$ (R1) of the linker
b) obtaining a conjugate intermediate: $Protein_1$-S—CH$_2$—C(=O)—NH-Linker[-NH—C(=O)—CH$_2$-$LG^2$]2
c) performing a leaving group exchange reaction increasing the reactivity of $LG^2$.
d) reacting the intermediate of c) with $Protein_2$-SH
e) obtaining the protein conjugate.

As above the leaving group exchange reaction transforming serves to activate the 2$^{nd}$ and 3$^{rd}$ reactive end of the linker. In one embodiment $LG^2$ is changed from Cl to I increasing the reactivity. In one embodiment $LG^1$ is changed from Cl to I increasing the reactivity. In one embodiment the reactive ends of both R2 and R3 in the final intermediate comprises —NH—C(=O)—CH$_2$—I.

If the intermediate of b) is obtained by alternative means of if a protein linker conjugate including only thiol reactive ends in the second (and/or third arm) the method may be applied starting from step 2.
b) obtaining a conjugate intermediate: $Protein_1$-Linker[-NH—C(=O)—CH$_2$-$LG^2$]$_2$
c) performing a leaving group exchange reaction increasing the reactivity of $LG^2$
d) reacting the intermediate of c) with $Protein_2$-SH and $Protein_3$-SH
e) obtaining the protein conjugate.

In one such embodiment the method is for preparing a protein conjugate, wherein $Protein_1$-linker and $Protein_2$-SH are coupled together obtaining a protein conjugate of Formula III, where two copies of $Protein_2$ is linked via sulfur atoms.

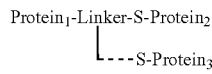

Formula III

The method comprising the steps of:
a) obtaining an conjugate intermediate or the structure:

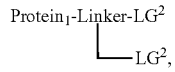

wherein $LG^2$ is a leaving group of low reactivity, b) performing a leaving group exchange reaction increasing the reactivity of $LG^2$
c) reacting the intermediate of b) with $Protein_2$-SH
d) obtaining the protein conjugate.

A protein linker intermediate may be used having the following structure:

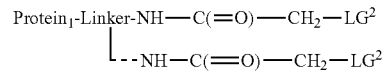

and as described above the LG may be a halogen that is exchanged for an alternative halogen with higher reactivity and as before Cl may be exchanged for an I that is highly reactive towards Cys residues.

Based on the above schemes the reactivity of the reactive ends is important and in one embodiment $LG^1$ has a higher reactivity than $LG^2$. In an embodiment $LG^1$ is Br or I. In one embodiment $LG^2$ is Cl.

In one embodiment the $LG^2$ is Cl and is exchange to I. The exchange reaction may be performed as an aqueous halogen exchange, such as an aqueous Finkelstein reaction. The reaction may be performed in an aqueous KI solution. The solution may further comprise ascorbic acid. In one embodiment the reaction is performed in the presence of 0.1-5 M KI and 10-50 mM ascorbic acid.

The duration of the various steps of the conjugation method may be adjusted for the individual proteins to be conjugated.

The reactions steps with $Protein_1$ may be performed for 1-24 hours, such as overnight.

The reactions steps with $Protein_2$ may be performed for 1-24 hours, such as overnight.

The methods above may be performed using linkers described herein above, such as two-armed or three-armed linkers as appropriate.

In all examples provide herein the reaction between the haloacetamide with the reduced free cysteine results in formation of a thioether (—CH$_2$—S—CH$_2$—) which connects the linker structure with the polypeptide. The —CH$_2$— groups of the thioether may be considered part of the linker and/or protein, but may be included in the structure to illustrate the identity of the linkage.

Intermediates

Based on the overall set out of the method described above a series of products and intermediates as described are part of the presents invention.

It is clear from the above that the protein conjugations can in many situations be performed in the reverse order. In the present overview it is contemplated that $Protein_1$ is the first protein to be conjugated. The two different orders of conjugation are also illustrated in example 3 of the application.

| Protein Conjugates |
|---|
| $Protein_1$-Linker-S-$Protein_2$ |
| $Protein_1$-Linker-CH$_2$—S—CH$_2$-$Protein_2$ |
| $Protein_1$-Linker-NH—C(=O)—CH$_2$—S-$Protein_2$ |
| $Protein_1$-S-Linker-NH—C(=O)—CH$_2$—S-$Protein_2$ |
| $Protein_1$-S—CH$_2$—C(=O)—NH-Linker-NH—C(=O)—CH$_2$—S-$Protein_2$ |

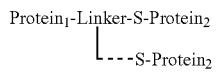

Protein Conjugates

Protein$_1$-Linker-CH$_2$—S—CH$_2$-Protein$_2$
└---CH$_2$—S—CH$_2$-Protein$_2$

Protein$_1$-Linker-NH—C(=O)—CH$_2$—S-Protein$_2$
└—NH—C(=O)—CH$_2$—S-Protein$_2$ Protein$_1$-S-Linker-S-Protein$_2$
└---S-Protein$_2$ Protein$_1$-CH$_2$—S—CH$_2$-Linker-CH$_2$—S—CH$_2$-Protein$_2$
└---CH$_2$—S—CH$_2$-Protein$_2$ Protein$_1$-S-Linker-NH—C(=O)—CH$_2$—S-Protein$_2$
└—NH—C(=O)—CH$_2$—S-Protein$_2$ Protein$_1$-CH$_2$—S—CH$_2$-Linker-NH—C(=O)—CH$_2$—S-Protein$_2$
└—NH—C(=O)—CH$_2$—S-Protein$_2$ Protein$_1$-S—CH$_2$—C(=O)—NH-Linker-S-Protein$_2$
└---S-Protein$_2$ Protein$_1$-S—CH$_2$—C(=O)—NH-Linker-CH$_2$—S—CH$_2$-Protein$_2$
└---CH$_2$—S—CH$_2$-Protein$_2$ Protein$_1$-S—CH$_2$—C(=O)—NH-Linker-NH—C(=O)—CH$_2$—S-Protein$_2$
└---NH—C(=O)—CH$_2$—S-Protein$_2$

Protein$_1$-linker intermediates

Protein$_1$-Linker-Cl/Br/I
Protein$_1$-Linker-NH—C(=O)—CH$_2$—Cl/Br/I
Protein$_1$-S-Linker-NH—C(=O)—CH$_2$—Cl/Br/I
Protein$_1$-CH$_2$—S—CH$_2$-Linker-NH—C(=O)—CH$_2$—Cl/Br/I
Protein$_1$-S—CH$_2$—C(=O)—NH-Linker-NH—C(=O)—CH$_2$—Cl/Br/I Protein$_1$-Linker-Cl/Br/I
└—Cl/Br/I Protein$_1$-Linker-NH—C(=O)—CH$_2$—Cl/Br/I
└---NH—C(=O)—CH$_2$—Cl/Br/I Protein$_1$-S-Linker-CL/Br/I
└—CL/Br/I Protein$_1$-CH$_2$—S—CH$_2$-Linker-CL/Br/I
└—CL/Br/I Protein$_1$-S-Linker-NH—C(=O)—CH$_2$—Cl/Br/I
└---NH—C(=O)—CH$_2$—Cl/Br/I Protein$_1$-CH$_2$—S—CH$_2$-Linker-NH—C(=O)—CH$_2$—Cl/Br/I
└---NH—C(=O)—CH$_2$—Cl/Br/I Protein$_1$-S—CH$_2$—C(=O)—NH-Linker-Cl/Br/I
└---Cl/Br/I Protein$_1$-S—CH$_2$—C(=O)—NH-Linker-NH—C(=O)—CH$_2$—Cl/Br/I
└---NH—C(=O)—CH$_2$—C/Br/I

Protein$_2$-linker intermediates

I/Br/Cl-Linker-Protein$_2$
I/Br/Cl—CH$_2$—C(=O)—NH-Linker-Protein$_2$
I/Br/Cl—CH$_2$—C(=O)—NH-Linker-S-Protein$_2$
I/Br/Cl—CH$_2$—C(=O)—NH-Linker-NH—C(=O)—CH$_2$-Protein$_2$ I/Br/Cl-Linker-Protein$_2$
└—Protein$_2$ I/Br/Cl—CH$_2$—C(=O)—NH-Linker-Protein$_2$
└—Protein$_2$ I/Br/Cl-Linker-S-Protein$_2$
└—S-Protein$_2$ I/Br/Cl-Linker-CH$_2$—S—CH$_2$-Protein$_2$
└—CH$_2$—S—CH$_2$-Protein$_2$ -continued

| Protein₂-linker intermediates |
|---|
| 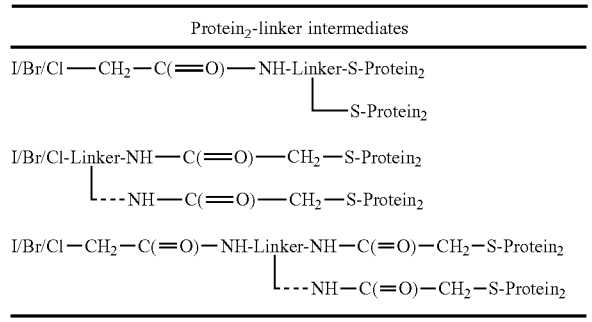 |

In one embodiment the intermediate is a structure with two Fc polypeptides individually linked to two arms of the linker, while the 1st arm is used for conjugation with a different protein/peptide. The intermediate according to the invention may thus by a trivalent linker structure including Fc polypeptides linked to arm 2 and 3, while arm 1 is still free. In the alternative the intermediate is a protein conjugate to arm 1 of the trivalent linker which is thus suited for conjugation to the Fc polypeptides via arm 2 and arm 3.

The overall structure of the protein conjugate including two Fc polypeptides, independent of the reactive end of the linkers, is

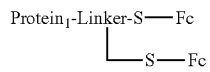

In an embodiment the conjugate includes thiol linkages of Fc medicated by a halo-acetamide leaving group providing the structure —NH—C(=O)—CH₂— inserted in the protein conjugate:

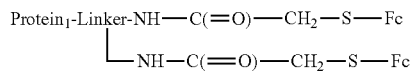

Details with regards to the trivalent linker have been provided elsewhere in the application and can be read into the structures above.

While certain features of the invention have been described herein and illustrated in the subsequence examples, many modifications, substitutions, changes, and equivalents will now occur to those of ordinary skill in the art. It is, therefore, to be understood that the appended embodiment and claims are intended to cover all such modifications and changes as fall within the true spirit of the invention.

EMBODIMENTS

1. A protein conjugate of the following structure

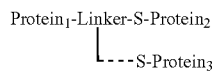

wherein
Linker is a chemical moiety
S is a sulfur atom and
Protein₁ is covalently linked to Protein₂ and Protein₃ via the linker and sulfur atoms.

2. The protein conjugate of embodiment 1, wherein the conjugate has the following structure

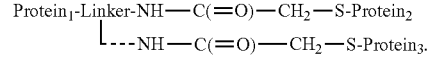

3. The protein conjugate of embodiment 1, wherein the conjugate has the following structure

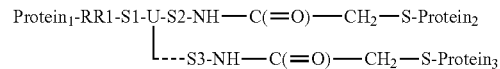

wherein U represents a central unit, RR1 a reactive end radical and S1, S2 and S3 represent individual spacers.

4. The conjugate according to any of the previous embodiment, wherein the sulfur atom's (—S—) are part of thioethers (—CH₂—S—CH₂—).

5. The conjugate according to any of the previous embodiments, wherein U comprises or consists of a nitrogen atom.

6. The conjugate according to any of the previous embodiments, wherein U comprises or consists of a benzene ring structure.

7. The conjugate according to any of the previous embodiments, wherein Protein₂ and Protein₃ are Fc polypeptides.

8. The conjugate according to any of the previous embodiments, wherein the conjugate has the structure:

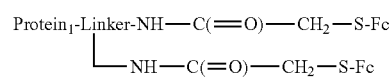

9. The conjugate according to any of the previous embodiments, wherein the conjugate has the structure:

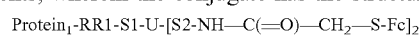

wherein
RR1 a reactive end radical,
S1 and S2 represent individual spacers,
U represents a central unit and
Fc is an Fc polypeptide.

10. The conjugate according to any of the previous embodiments, wherein Protein₁ is a growth hormone.

11. The conjugate according to any of the previous embodiments, wherein the conjugate has the structure:

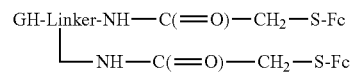

wherein GH represents a growth hormone molecule.

12. The conjugate according to any of the previous embodiments, wherein the conjugate has the structure:

wherein
GH represents a growth hormone molecule,
RR1 a reactive end radical
S1 and S2 represent individual spacers
U represents a central unit and
Fc is an Fc polypeptide.

13. The conjugate according to embodiments 7 to 12, wherein the Fc polypeptides is derived from IgG, such are IgG1, IgG2, IgG3 or IgG4.
14. The conjugate according to any of embodiments 7-13, wherein the Fc polypeptides comprise a hinge region.
15. The conjugate according to any of embodiments 7-14, wherein the hinge region of each Fc polypeptide includes a Cys residue.
16. The conjugate according to any of embodiments 7-15, wherein the hinge region of the Fc polypeptide is selected from the group of sequences consisting of: an IgG1 derived hinge sequence and an IgG4 derived sequence.
17. The conjugate according to embodiment 16, wherein the IgG1 derived hinge sequence is selected from: PKSCDKTHTCPPCP, PPCP, PCP and CP.
18. The conjugate according to embodiment 16, wherein the IgG4 derived hinge sequence is selected from: SKYGPPCPSCP, PSCP, SCPL and CP.
19. The conjugate according to any of the previous embodiments of the following structure

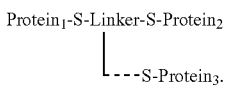

20. The conjugate according to any of the previous embodiments wherein the conjugate has the structure:

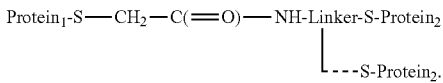

21. The conjugate according to any of the previous embodiments, wherein the conjugate has the structure:

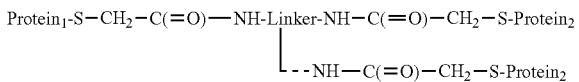

22. The conjugate according to any of the previous embodiments, wherein the sulfur atoms (—S—) are derived from protein thiols.
23. The conjugate according to any of the previous embodiments, wherein the sulfur atoms (—S—) are derived from protein cysteines.
24. The conjugate according to any of the previous embodiments, wherein the sulfur atoms (—S—) are derived from free Cys's.
25. The conjugate according to any of the previous embodiments, wherein one or more of the protein cysteine's is/are wild type residue(s).
26. The conjugate according to any of the previous embodiments, wherein one or more of the protein cysteines is/are variant amino acid residue(s).
27. The conjugate according to any of the previous embodiments, wherein the —S— linking Protein$_2$ and Protein$_3$ with the linker are from wild type cysteines.
28. The conjugate according to any of the previous embodiments 19-27, wherein the —S— linking Protein$_1$ with the linker is derived from a variant cysteine.
29. The conjugate according to any of the previous embodiments 19-28, wherein the —S— linking Protein$_1$ is derived from a free Cys.
30. The conjugate according to any of the previous embodiments 19-29, wherein the —S— linking Protein$_1$ is derived from a free cysteine in a growth hormone variant selected from the group consisting of T3C, P5C, S7C, D11C, H18C, Q29C, E30C, E33C, A34C, Y35C, K38C, E39C, Y42C, S43C, D47C, P48C, 555C, 557C, P59C, S62, E65C, Q69C, E88C, Q91C, 595C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C.
31. The conjugate according to any of the previous embodiments 19-30, wherein the —S— linking Protein$_1$ is derived from a free cysteine in a growth hormone variant selected from the group consisting of A98C, N99C, L101C, V102C and S108C.
32. The conjugate according to any of the previous embodiments 19-31, wherein the —S— linking Protein$_1$ is derived from a Cys substitution located within AA 93-106 in a growth hormone variant.
33. A trivalent linker of the structure:

wherein U represent a central unit,
S1, S2 and S3 represent individual spacers and
R1, R2 and R3 individually represent a reactive end.
34. The linker according to embodiment 33, wherein R1, R2 and R3 are not identical.
35. The linker according to any of the previous embodiments 33-34, wherein R2 and R3 are identical.
36. The linker according to any of the previous embodiments 33-35, wherein R2 and R3 are identical but R1 is different.
37. The linker according to any of the previous embodiments 33-36, wherein R2 and R3 are thiol reactive ends.
38. The linker according to any of the previous embodiment 33-37, wherein R2 and R3 each comprise a halogen leaving group, such as Bromide, Chloride or Iodide.
39. The linker according to any of the previous embodiments 33-38, wherein R2 and R3 comprise —NH—C(=O)—CH$_2$-LG, providing a linker of the structure:

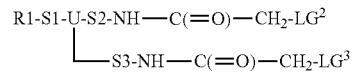

wherein LG$_2$ and LG$_3$ are halogen leaving groups
40. The linker according to any of the previous embodiments 33-39, wherein the reactive ends R2 and R3 are identical cys reactive ends.
41. The linker according to any of the previous embodiments 33-40, wherein R1 is different from R2 and R3.
42. The linker according to any of the previous embodiments 33-41, wherein R1 has a different reactivity than R2 and R3.
43. The linker according to any of the previous embodiments 33-42, wherein R1 is a thiol reactive end.
44. The linker according to any of the previous embodiments 33-43, wherein R1 is a thiol reactive comprising a leaving group, such as Bromide, Chloride or Iodide.
45. The linker according to any of the previous embodiments 33-44, wherein the first linker arm has the structure LG$^1$-CH$_2$—C(=O)—S1-
46. The linker according to any of the previous embodiments 33-45, wherein R1 comprises Cl as LG$^1$ and R2 and R3 comprises Br as LG$^2$.

47. The linker according to any of the previous embodiments 33-46, wherein R1 comprises Br as $LG^1$ and R2 and R3 comprises Cl as $LG^2$.
48. The linker according to any of the previous embodiments 33-47, wherein S2 and S3 are identical.
49. The linker according to any of the previous embodiments 33-48, wherein the length of the linker is 10 to 60 atoms, such as 12-45, or such as 15-40 atoms.
50. The linker according to any of the previous embodiments 33-49, wherein S2 and S3 is a short spacer, such as —(CH₂)₂—.
51. The linker according to any of the previous embodiments 33-50, wherein 51 is different from S2 and S3.
52. The linker according to any of the previous embodiments 33-51, wherein 51 is an extended spacer of 10-50 atoms in length.
53. The linker according to any of the previous embodiments 33-52, wherein 51 comprise one or more spacer elements linked by peptide bond(s).
54. The linker according to any of the previous embodiments 33-53, wherein the spacer elements of 51 are selected from the group of:

a)
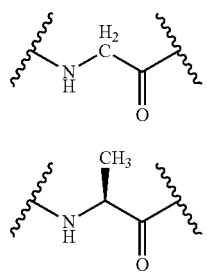

b)
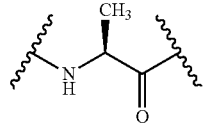

c)
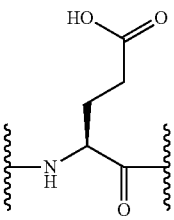

d)
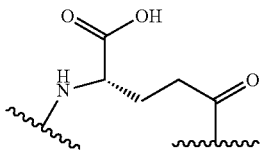

e)
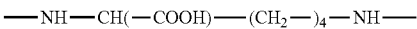
—NH—CH(—COOH)—(CH₂—)₄—NH— f)
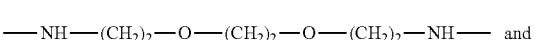
—NH—(CH₂)₂—O—(CH₂)₂—O—(CH₂)₂—NH— and

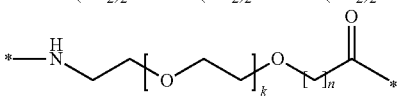

wherein k is an integer in the range of 1-5, and n is an integer in the range of 1-5.

55. The linker according to any of the previous embodiments 33-54, wherein a spacer element is *—NH—(CH₂)₂—O—(CH₂)₂—O—CH₂—CO—* (OEG or a di-radical of 8-amino-3,6-dioxaoctanoic acid).
56. The linker according to any of the previous embodiments 33-55, wherein the linker is selected from the group consisting of:

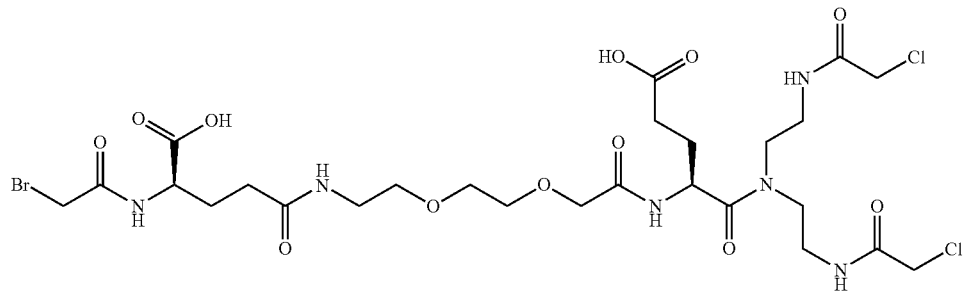

(S)-4-(2-{2-[((S)-1-{Bis-[2-(2-chloro-acetylamino)-ethyl]-carbamoyl}-3-carboxy-propylcarbamoyl)-methoxy]-ethoxy}-ethylcarbamoyl)-2-(2-bromo-acetylamino)-butyric acid

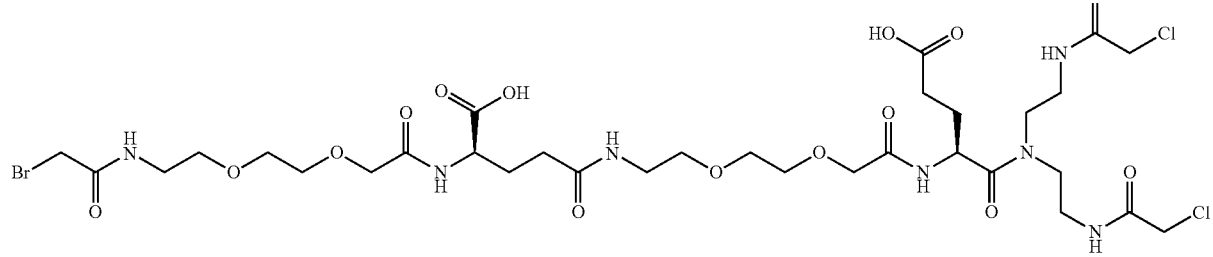

4S,18S)-4-(bis(2-(2-Chloroacetamido)ethyl)carbamoyl)-18-(2-(2-(2-(2-bromoacetamido)ethoxy)ethoxy)acetamido)-6,15-dioxo-8,11-dioxa-5,14-diazanonadecanedioic acid
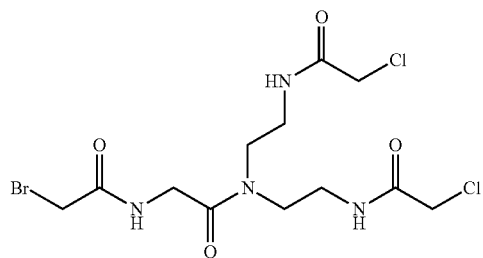
2-(2-bromoacetamido)-N,N-bis(2-(2-chloroacetamido)ethyl)acetamide
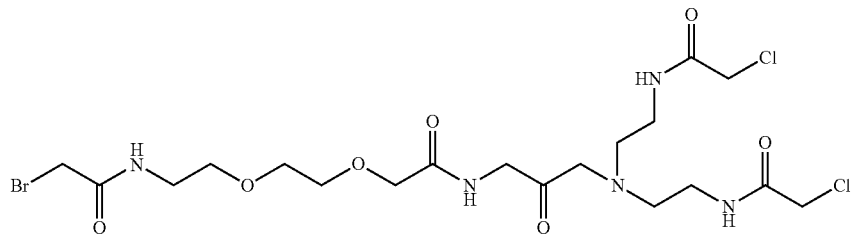 [SMILES: O=C(CNC(=O)COCCOCCNC(=O)CBr)CN(CCNC(=O)CCl)CCNC(=O)CCl]
2-(2-(2-(2-(2-bromoacetamido)ethoxy)ethoxy)acetamido)-N,N-bis(2-(2-chloroacetamido)ethyl)acetamide
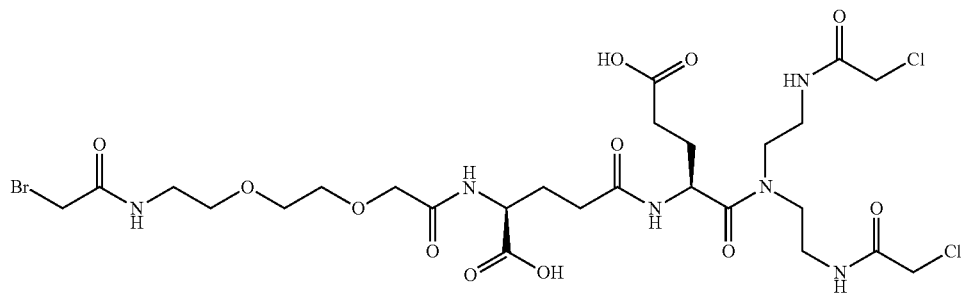 [SMILES: O=C(O)CC[C@H](NC(=O)CC[C@H](NC(=O)COCCOCCNC(=O)CBr)C(=O)O)C(=O)N(CCNC(=O)CCl)CCNC(=O)CCl]
(13R,18S)-18-(bis(2-(2-Chloroacetamido)ethyl)carbamoyl)-1-bromo-13-carboxy-2,11,16-trioxo-6,9-dioxa-3,12,17-triazahenicosan-21-oic acid
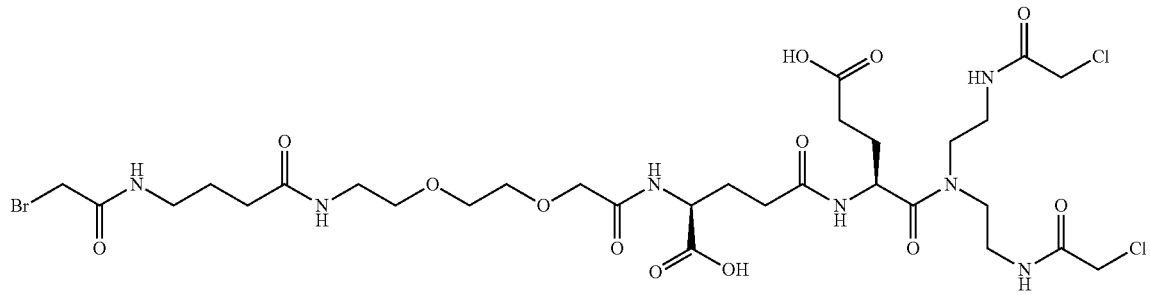 [SMILES: O=C(O)CC[C@H](NC(=O)CC[C@H](NC(=O)COCCOCCNC(=O)CCCNC(=O)CBr)C(=O)O)C(=O)N(CCNC(=O)CCl)CCNC(=O)CCl]

(18R,23S)-23-(Bis(2-(2-chloroacetamido)ethyl)carbamoyl)-1-bromo-18-carboxy-2,7,16,21-tetraoxo-11,14-dioxa-3,8,17,22-tetraazahexacosan-26-oic acid

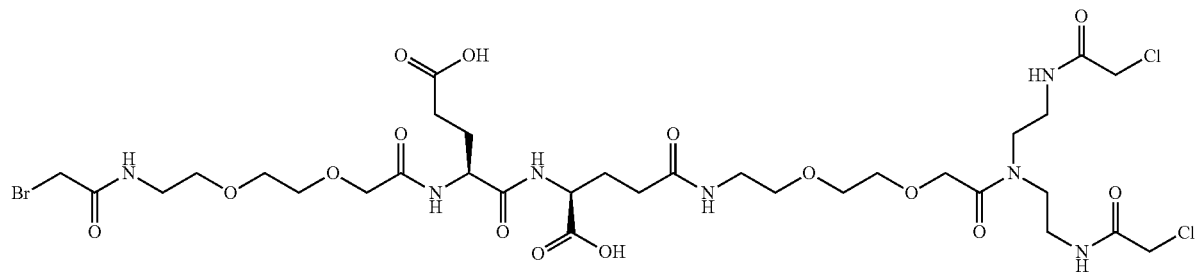 [SMILES: O=C(O)CC[C@H](NC(=O)COCCOCCNC(=O)CBr)C(=O)N[C@@H](CCC(=O)NCCOCCOCC(=O)N(CCNC(=O)CCl)CCNC(=O)CCl)C(=O)O]

(R)-4-{2-[2-({Bis-[2-(2-chloro-acetylamino)-ethyl]-carbamoyl}-methoxy)-ethoxy]-thylcarbamoyl}-2-[(S)-2-(2-{2-[2-(2-bromo-acetylamino)-ethoxy]-ethoxy}-acetylamino)-4-carboxy-butyrylamino]-butyric acid

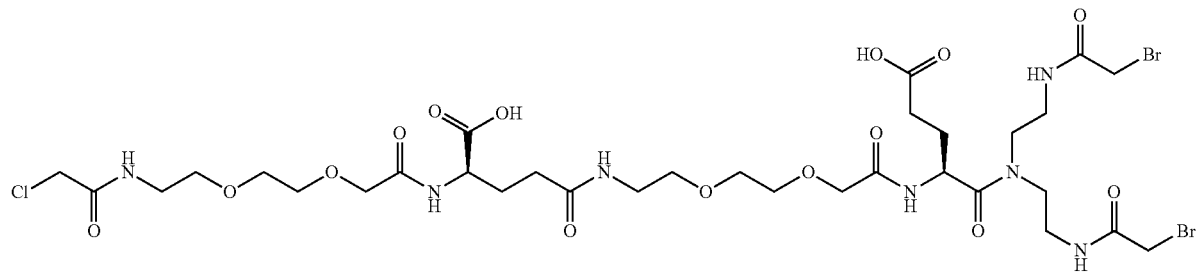 [SMILES: O=C(O)CC[C@H](NC(=O)COCCOCCNC(=O)CC[C@@H](NC(=O)COCCOCCNC(=O)CCl)C(=O)O)C(=O)N(CCNC(=O)CBr)CCNC(=O)CBr]

(4S,18S)-4-(bis(2-(2-Bromoacetamido)ethyl)carbamoyl)-18-(2-(2-(2-(2-chloroacetamido)ethoxy)ethoxy)acetamido)-6,15-dioxo-8,11-dioxa-5,14-diazanonadecanedioic acid

45

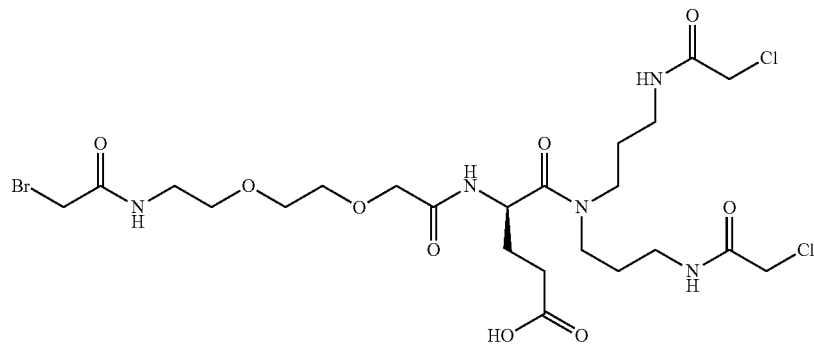 [SMILES: O=C(O)CC[C@@H](NC(=O)COCCOCCNC(=O)CBr)C(=O)N(CCCNC(=O)CCl)CCCNC(=O)CCl]

(4S)-5-[bis[3-[(2-chloroacetyl)amino]propyl]amino]-
4-[[2-[2-[2-[(2-bromoacetyl)amino]ethoxy]ethoxy]
acetyl]amino]-5-oxo-pentanoic acid

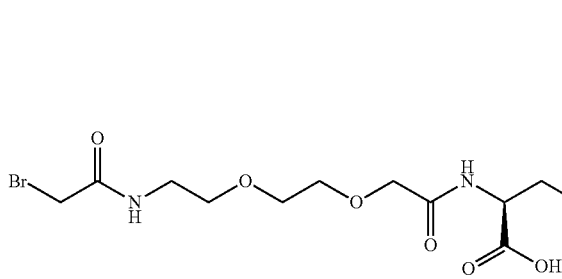

(2R)-6-[bis[2-[(2-chloroacetyl)amino]ethyl]carbam-
oylamino]-2-[[2-[2-[2-[(2-bromoacetyl)amino]
ethoxy]ethoxy]acetyl]amino]hexanoic acid

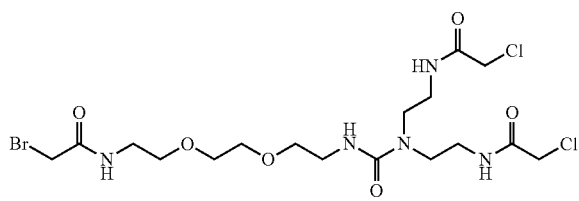 [SMILES: O=C(CCl)NCCN(CCNC(=O)CCl)C(=O)NCCOCCOCCNC(=O)CBr]

N-[2-[2-[2-[2-[(2-bromoacetyl)amino]ethoxy]
ethoxy]ethylcarbamoyl]-[2-[(2-chloroacetyl)amino]
ethyl]amino]ethyl]-2-chloro-acetamide

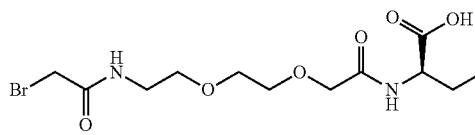

(2R)-2-[[2-[2-[2-[(2-bromoacetyl)amino]ethoxy]
ethoxy]acetyl]amino]-5-[2-[2-[2-[[(1S)-3-carboxy-1-
[2-[(2-chloroacetyl)-[2-[(2-chloroacetyl)amino]-
ethyl]amino]ethylcarbamoyl]propyl]amino]-2-oxo-
ethoxy]ethoxy]ethylamino]-5-oxo-pentanoic acid 57. A method for preparation of a protein conjugate, wherein Protein$_1$-SH, Protein$_2$-SH and a thiol reactive linker are coupled together obtaining a protein conjugate of Formula II Protein$_1$-S—CH$_2$—C(=O)—NH-Linker-NH—C
(=O)—CH$_2$—S-Protein$_2$  (Formula II)

wherein the thiol reactive linker has the structure:

LG$^1$-CH$_2$—C(=O)—NH-Linker-NH—C(=O)—
CH$_2$-LG$^2$, wherein LG1 has a higher reactivity than LG$^2$, the method comprising the steps of:

a) reacting Protein$_1$-SH with —NH—C(=O)—CH$_2$-LG$^1$ of the linker b) obtaining a conjugate intermediate: Protein$_1$-S—CH$_2$—C(=O)—NH-Linker-NH—C(=O)—CH$_2$-LG$^2$ c) performing a leaving group exchange reaction increasing the reactivity of LG$^2$.

d) reacting the intermediate of c) with Protein$_2$-SH e) obtaining the protein conjugate.

58. A method for preparing a protein conjugate, wherein Protein$_1$-Linker-NH—C(=O)—CH$_2$-LG and Protein$_2$-SH are coupled together obtaining a protein conjugate of Formula I Protein$_1$-Linker-NH—C(=O)—CH$_2$—S-Protein$_2$  (Formula I)

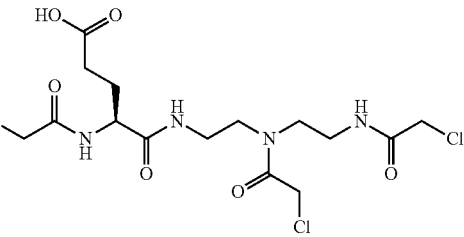

wherein LG is a leaving group of low reactivity, the method comprising the steps of b) obtaining an conjugate intermediate: Protein$_1$-Linker-NH—C(=O)—CH$_2$-LG c) performing a leaving group exchange reaction increasing the reactivity of LG.

d) reacting the conjugate intermediate of b) with Protein$_2$-SH e) obtaining the protein conjugate.

59. A method for preparation of a protein conjugate, wherein Protein$_1$-linker and Protein$_2$-SH are coupled together obtaining a protein conjugate of Formula III:

the method comprising the steps of:

b) obtaining an conjugate intermediate or the structure:

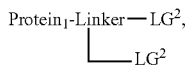

wherein LG² is a leaving group of low reactivity, c) performing a leaving group exchange reaction increasing the reactivity of LG².

d) reacting the intermediate of b) with Protein₂-SH e) obtaining the protein conjugate.

60. A method for preparation of a protein conjugate, wherein Protein₁-SH, Protein₂-SH and a thiol reactive linker are coupled together obtaining a protein conjugate of Formula VI

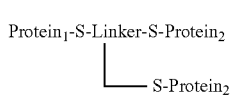
(Formula IV)

wherein the thiol reactive linker has the structure:

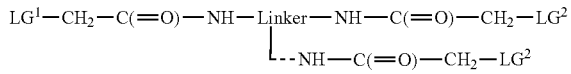

wherein LG¹ has a higher reactivity than LG², the method comprising the steps of:

a) reacting Protein₁-SH with —NH—C(=O)—CH₂-LG¹ of the linker b) obtaining a conjugate intermediate: Protein₁-S—CH₂—C(=O)—NH-Linker-[NH—C(=O)—CH₂-LG²]2 c) performing a leaving group exchange reaction increasing the reactivity of LG².

d) reacting the conjugate intermediate of c) with Protein₂-SH e) obtaining the protein conjugate.

61. The method according to any of the above embodiments 57-60, wherein LG¹ is Br.

62. The method according to any of the above embodiments 57-61, wherein LG² is Cl.

63. The method according to any of the above embodiments 57-62, wherein LG¹ is Cl.

64. The method according to any of the above embodiments 57-63, wherein LG² is Br.

65. The method according to any of the above embodiments 57-64, wherein the exchange reaction is a Cl to I exchange.

66. The method according to any of the above embodiments 57-65, wherein the exchange reaction is performed in the presence of 0.1-5 M KI and 10-50 mM ascorbic acid.

67. The method according to any of the above embodiments 57-66, wherein protein-SH is reacted with a thiol reactive linker or a conjugate intermediate overnight 68. The method according to any of the above embodiments 57-67, wherein the Protein₁-Linker-[NH—C(=O)—CH₂—I]₂ is reacted with Protein₂-SH overnight.

69. The method according to any of the above embodiments 57-8, wherein an Fc domain is conjugated to Protein₁ via covalent linkage of both Fc polypeptide chains.

70. The method according to any of the above embodiments 57-69, wherein a step of obtaining Protein-SH by reduction is included.

EXAMPLES

Abbreviations amu=Atomic mass units
Boc=tert-Butyloxycarbonyl
O-t-Bu=tert-Butyl ester
t-Bu=tert-Butyl
CDCl₃=Deuterio chloroform
CD₃OD=Tetradeuterio methanol
CV=Column volumes
DMSO-d₆=Hexadeuterio dimethylsulfoxide
DCM=DCM, CH₂Cl₂, methylenechloride
DIC=Diisopropylcarbdiimide
DIPEA=diisopropylethylamine
DMF=N,N-Dimethylformamide
DMSO=Dimethylsulfoxide
DTT=Dithiothreitol
EDAC=1-Ethyl-3-(3-dimethylaminopropyl)carbodiimide hydrochloride
Et₂O=Diethyl ether
EtOAc=Ethyl acetate
FA=Formic acid
Fmoc=9H-Fluoren-9-ylmethoxycarbonyl
Fmoc-Glu-O-t-Bu=N-Fmoc-glutamic acid-1-t-butyl ester
Fmoc-Lys(Mtt)-OH=(S)-6-[(Diphenyl-p-tolyl-methyl)-amino]-2-(9H-fluoren-9-ylmethoxycarbo-nylamino)-hexanoic acid
Fmoc-OEG-OH=(2[2-(Fmoc-amino)ethoxy]ethoxy)acetic acid
Fmoc-Thx-OH=N-Fmoc-trans-4-aminomethylcyclohexan-carboxylic acid
H₂O=Water
hr(s)=Hour(s)
Hz=Hertz
HOBt=1-Hydroxybenzotriazole
HPLC=High pressure liquid chromatography
HPLC-MS=High pressure liquid chromatography—mass spectrometry
i.v.=Intravenous
L=Liter(s)
M=Molar
mbar=Millibar
mg=Milligram(s)
min.=Minute(s)
mL=Milliliter(s)
mM=Millimolar
mol=Mole(s)
mmol=Millimole(s)
m/z=Mass to charge ratio
MS=Mass spectrometry
MeCN=Acetonitrile
MeOH=Methanol
μL=Microliters
N=Normal
nm=Nanometer(s)
nmol=Nanomole(s)
NaCl=Sodium chloride
NaOH=Sodium hydroxide
NMR=Nuclear magnetic resonance spectroscopy
OEG=(2[2-(Amino)ethoxy]ethoxy)acetyl
ppm=Parts per million
PyBrOP=Bromo-tris-pyrrolidino-phosphonium hexafluorophosphate
p.o.=Per oral
RP=Reverse phase
rt or RT=Room temperature tr or Rt=Retention time
sec=Second(s)
s.c.=Subcutaneous
TCTU=O-(6-Chloro-benzotriazol-1-yl)-N,N,N',N'-tetramethyluronium tetrafluoroborate
TEA=Triethylamine
TFA=Trifuloroacetic acid
THF=Tetrahydrofuran
TIS=Triisopropylsilane
TSTU=O—(N-Succinimidyl)-1,1,3,3-tetramethyl uranium tetrafluoroborate
HATU=1-[bis(dimethylamino)methylene]-1H-1,2,3-triazolo[4,5-b]pyridinium 3-oxid hexafluorophosphate
TCEP=Tris(2-carboxyethyl)phosphine
TPPDS=Bis(p-sulfonatophenyl)phenylphosphine
TPPTS=Tris((m-sulfonatophenyl)phenylphosphine
Methods
Method 1—Method for Preparation and Analysis of a Growth Hormone Protein The gene coding for the growth hormone or growth hormone variant was inserted recombinant into a plasmid vector. A suitable *E. coli* strain was subsequently transformed using the plasmid vector. hGH or GH variants may be expressed with an N-terminal methionine or as a MEAE fusion from which the MEAE sequence is subsequently cleaved off.

Cell stock was prepared in 25% glycerol and stored at −80° C. Glycerol stock strain was inoculated into LB plates and subsequently incubated at 37° C. overnight. The content of each plate was washed with LB medium and diluted into 500 mL LB medium for expression. The cultures were incubated at 37° C. with shaking at 220 rpm until $OD_{600}$ 0.6 was reached. Succeeding induction was performed using 0.2 mM IPTG at 25° C. for 16 hrs. Cells were finally harvested by centrifugation.

Cells were subsequently suspended in 10 mM Tris-HCl, pH 9.0 containing 0.05% Tween 20, 2.5 mM EDTA, 10 mM cystamine and 4M urea, and disrupted using a cell disrupter at 30 kPSI. The supernatant was collected by centrifugation and subsequently subjected to chromatographic purification.

The purification was performed using ion-exchange chromatography and hydrophobic interaction, followed by removal of the peptide tag using human dipeptidyl peptidase I (hDPPI) expressed from CHO cell. Final purification was achieved by isoprecipitation and ion-exchange chromatography. The purification could also be achieved by using but not limited to ion-exchange chromatography, hydrophobic interaction chromatography, affinity chromatography, size exclusion chromatography and membrane based separation techniques known to a person skilled in the art.

Characterization of Growth Hormone Preparation

The intact purified protein was analysed using MALDI-MS. The observed mass corresponded to the theoretical mass deduced from the amino acid sequence.

The expected linkage disulfide bonds may be demonstrated by peptide mapping using trypsin and AspN digestion followed by MALDI-MS analysis of the digest before and after reduction of the disulfide bonds with DTT.

Proteolytic Digestion:

100 µL of test compound solution at 1 mg/mL in ammonium bicarbonate buffer is degraded by enzyme for up till 24 hrs at 37° C. Sub-samples are taken to various time points and the proteolytic reaction is stopped by acidifying the sample by 10 times dilution into 1% TFA. These diluted samples are analysed by reversed phase HPLC to estimate the degree of proteolytic digestion.

HPLC Method:

10 µL of the above solution is injected on a reversed phase Vydac C4 2×150 mm column eluted with a linear gradient from 0.1% TFA in water to 100% MeCN containing 0.1% TFA over a period of 30 min at a flow rate of 0.2 mL/min. Detection of peaks is performed at 214 nm UV absorption. Percentage (%) intact compound at time point t=T is calculated from the peak area at time point t=T ($A_T$) and the peak area at t=0 ($A_0$) as ($A_T/A_0$)×100%. Percentage (%) intact compound is plotted against time using GraphPad Prims software ver. 5.01. Half-life ($T_{1/2}$) is calculated as one phase decay also by GraphPad Prism software. Examples of enzymes that may be used are elastase (Sigma from porcine pancrease) and chymotrypsin (Roche sequencing grade). Example of buffer is 50 mM ammonium bicarbonate, pH=8.5.

Capillary Electrophoresis:

Capillary electrophoresis was carried out using an Agilent Technologies 3DCE system (Agilent Technologies). Data acquisition and signal processing were performed using Agilent Technologies 3DCE ChemStation. The capillary was a 64.5 cm (56.0 cm efficient length) 50 µm i.d. "Extended Light Path Capillary" from Agilent. UV detection was performed at 200 nm (16 nm Bw, Reference 380 nm and 50 nm Bw). The running electrolyte was phosphate buffer 50 mM pH 7 (method A). The capillary was conditioned with 0.1M NaOH for 3 min, then with Milli-Q water for 2 min and with the electrolyte for 3 min. After each run, the capillary was flushed with milli-Q water for 2 min, then with phosphoric acid for 2 min, and with milli-Q water for 2 min. The hydrodynamic injection was done at 50 mbar for 4.0 sec. The voltage was +25 kV. The capillary temperature was 30° C. and the runtime was 10.5 min.

Maldi-Tof Mass Spectrometry:

Molecular weights were determined using the Autoflex Maldi-Tof instrument (Bruker). Samples were prepared using alfa-cyano-4-hydroxy-cinnamic acid as matrix.

RP-HPLC:

RP-HPLC analysis was performed on an Agilent 1100 system using a Vydac 218TP54 4.6 mm×250 mm 5 µm C-18 silica column (The Separations Group, Hesperia). Detection was by UV at 214 nm, 254 nm, 280 nm and 301 nm. The column was equilibrated with 0.1% $TFA/H_2O$ and the sample was eluted by a suitable gradient of 0 to 90% MeCN against 0.1% $TFA/H_2O$.

LC-MS:

LC-MS analysis was performed on a PE-Sciex API 100 or 150 mass spectrometer equipped with two Perkin Elmer Series 200 Micropumps, a Perkin Elmer Series 200 autosampler, an Applied Biosystems 785A UV detector and a Sedex 75 Evaporative Light scattering detector. A Waters Xterra 3.0 mm×50 mm 5p C-18 silica column was eluted at 1.5 mL/min at room temperature. It was equilibrated with 5% MeCN/0.1% $TFA/H_2O$ and eluted for 1.0 min with 5% MeCN/0.1% $TFA/H_2O$ and then with a linear gradient to 90% MeCN/0.1% $TFA/H_2O$ over 7 min. Detection was by UV detection at 214 nm and Evaporative light Scattering. A fraction of the column elute was introduced into the ionspray interface of a PE-Sciex API 100 mass spectrometer. The mass range 300-2000 amu was scanned every 2 seconds during the run.

Quantification of Protein:

Protein concentrations were estimated by measuring absorbance at 280 nm using a NanoDrop ND-1000 UV-spectrophotometer.

Enzymatic Peptide Mapping for Determination of Site(s) of Derivatization:

Peptide mapping was performed using Asp-N digestion of the reduced and alkylated protein. First the protein was treated with DTT and iodoacetamide according to standard procedures. The alkylated product was purified using HPLC. Subsequently the alkylated purified product was digested overnight with endoprotease Asp-N (Boehringer) at an enzyme:substrate ratio of 1:100. The digest was HPLC separated using a C-18 column and standard TFA/MeCN buffer system. The resulting peptide map was compared to that of un-derivatized hGH and fractions with different retention times were collected and further analysed using Maldi-tof mass spectrometry.

SDS Page:

SDS poly-acrylamide gel electrophoresis was performed using NuPAGE 4%-12% Bis-Tris gels (Invitrogen NPO321BOX). The gels were silver stained (Invitrogen LC6100) or Coomassie stained (Invitrogen LC6065) and where relevant also stained for PEG with barium iodide as described by M. M. Kurfurst in *Anal. Biochem.* 200(2), 244-248, (1992).

Protein Chromatography:

Protein chromatography was performed on an Äkta Explorer chromatographic system and columns from GE Health Care. Anion exchange was done using a Q-Sepharose HP 26/10 column. Starting buffer was 20 mM triethanolamine buffer pH 8.5 and eluting buffer was starting buffer+0.2 M NaCl. The compounds were typically eluted with a gradient of 0-75% eluting buffer over 15 column volumes. De-salting and buffer exchange was performed using a HiPrep 26/10 column.

Method 2—Method for Preparation of an Fc-Domain

Fc domains may be expressed by technologies known in the art such as by expression in *E. coli* (WO05047334, WO05047335, WO05047336, WO05047337, and WO05001025) or in mammalian cells such as HEC (Farge, F. et. al, Journal of Chromatography (1976) vol 123, page 247-250). The following overall method has been applied for the present application.

An Fc-domain was obtained using a fragment of human IgG4, which was truncated at the N-terminal of the hinge region. The coding region including a Met start codon was inserted in a pET11d derived vector to guide expression of a Fc polypeptide with MPSCPAPEFLGGPSVF . . . N-terminal. The Fc polypeptide was expressed in *E. coli*. The strain used was (BL21(DE3)_TKO::ybhE as described in WO2010052335 additionally including an ybhE knock-in. The Fc domain was subsequently purified. An initiator ATG (Met-codon) was included in-frame with the truncated hinge allowing expression in *E. coli*. Due to host enzymes this Methionine was removed and not present in the purified Fc which thus have a proline at the N-terminal. An expression level of above 5 g/L of soluble Fc fragment from the cytoplasm of *E. coli* was obtained using defined medium. After purification a yield of 1.4 g/L was obtained. An in vitro disulfide bridge formation step was included to ensure correct folding of the Fc domain.

*E. coli* cells were cultivated at 37° C. in defined medium to an optical density ($OD_{600}$) of about 80 in 20-L fermentor. Then the culture was induced with 0.2 mM IPTG and continue to cultivate at 25° C. for overnight. Finally the cells were harvested by centrifugation.

After the homogenization of the cell pellet in buffer containing Tris-HCl 50 mM, NaCl 300 mM, EDTA 5 mM and DTT 1 mM, pH 7.4, the target protein was recovered by treatment with 0.2% PEI (polyethyleneimine) for 30 min followed by centrifugation at 6,000×g. The Fc was purified from the supernatant of the cell lysate by affinity chromatography using MabSelect SuR (GE Healthcare Life Sciences), and then oxidized by adding urea 3.5 M, cystamine 0.01 mM, pH 8.5 at room temperature for overnight. Finally, the formed Fc dimer was further purified by ion-exchange chromatography using Q Sepharose HP (GE Healthcare Life Sciences) at pH 8.5. The final protein is in TEA (Tris-acetate-EDTA) 20 mM, NaCl 500 mM, pH 8.0.

Method 4—Method for Preparation of Protein Conjugates— GH First

Chemistry

The conjugation method can be performed with a variety of suitable proteins comprising suitable attachment points, here exemplified using a GH variant and an Fc domain all including one or more sulfur atom(s) that serves as connector to the linker.

The conjugate, GH-A-B-Protein (IX) is prepared as illustrated below:

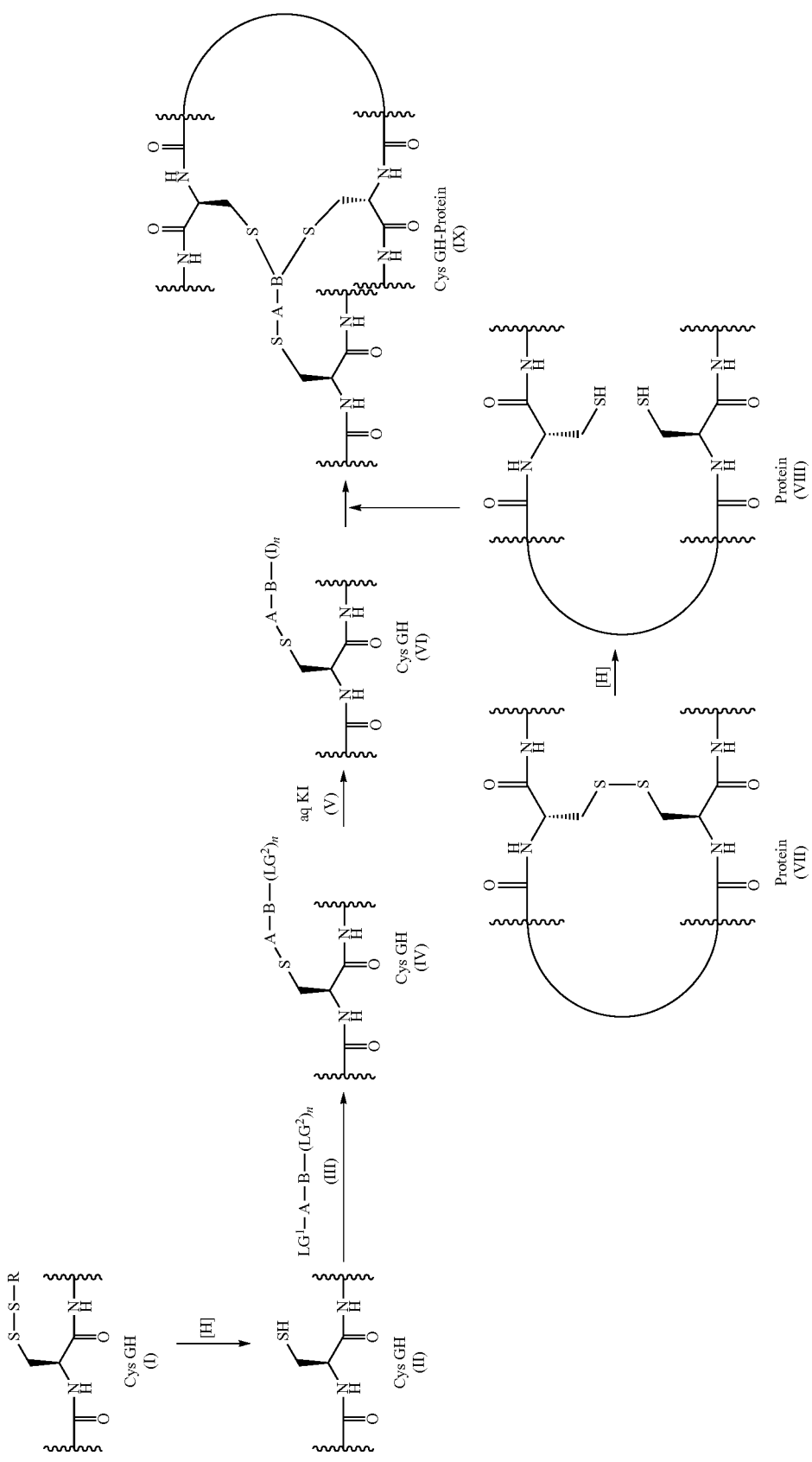

Reaction where linker is first attached to hGH and subsequently to Fc.

The cysteine residue in (I) is optionally protected as a mixed disulfide (GH-S-S-R) with R being a small organic moiety. Non limited examples of mixed disulfides may include disulfides between cysteamine (R=—CH$_2$CH$_2$NH$_2$); cysteine (R=—CH$_2$CH(C(=O)OH)NH$_2$); homocysteine (R=—CH$_2$CH$_2$CH(C(=O)OH)NH$_2$); and glutathione (R=—CH$_2$CH(C(=O)NH—CH$_2$C(=O)OH)NH—C(=O)CH$_2$CH$_2$CH(C(=O)OH)NH$_2$).

The conjugation process utilise a trivalent linker LG$^1$-A-B-(LG$^2$)$_2$ (III) wherein LG$^1$ and LG$^2$ independently represent inorganic leaving groups such as —Cl, —Br, —I and/or organic leaving groups such as mesylate or tosylate. Conjugation of reduced GH (II) with the linker LG$^1$-A-B-(LG$^2$)$_n$ (III) occurs via nucleophilic substitution (II+III→IV). Selectivity for LG$^1$ versus LG$^2$ is obtained via utilization of difference in leaving group ability between LG$^1$ and LG$^2$. In order for LG$^2$ to act as a proper leaving group in the next step, it is changed into iodo (VI) via an aqueous Finkelstein reaction with potassium iodine. This conjugate intermediate (VI) is next treated with a protein of interest (VIII) here a Fc-domain wherein a disulphide bond selectively has been reduced (VII→VIII) using as suitable reducing agent such as dithiothreitol (DTT), TCEP, TPPTS, and TPPDS affording the GH-A-B-Protein conjugate (IX).

The steps of the reaction may be described as follows starting from a GH compound (I) having an internal free Cys, a trivalent linker (III) and a Fc domain including a reducible disulfide bond.

1) Optionally liberating a free Cys GH (II) via reduction of mixed disulfide (I) with a suitable selective reducing agent
2) Alkylating a free Cys GH (II) with an trivalent linker (III) affording a Cys conjugated GH protein linker intermediate (IV)
3) Activating leaving groups LG$^2$ in the intermediate (IV) via an aqueous Finkelstein iodine exchange reaction (V) affording activated Cys GH conjugate intermediate (VI)
4) Liberating free cysteines in an Fc-domain (VII) via selective reduction of a disulfide bridge with a suitable selective reducing agent affording (VIII)
5) Coupling of Fc-domain (VIII) with activated Cys GH conjugate intermediate (VI) affording a Cys conjugated GH-Fc conjugate (IX)

Method 5—Method for Preparation of Protein Conjugates—Fc First

In an alternative the conjugate GH-A-B-Protein (IX) is prepared as illustrated below:

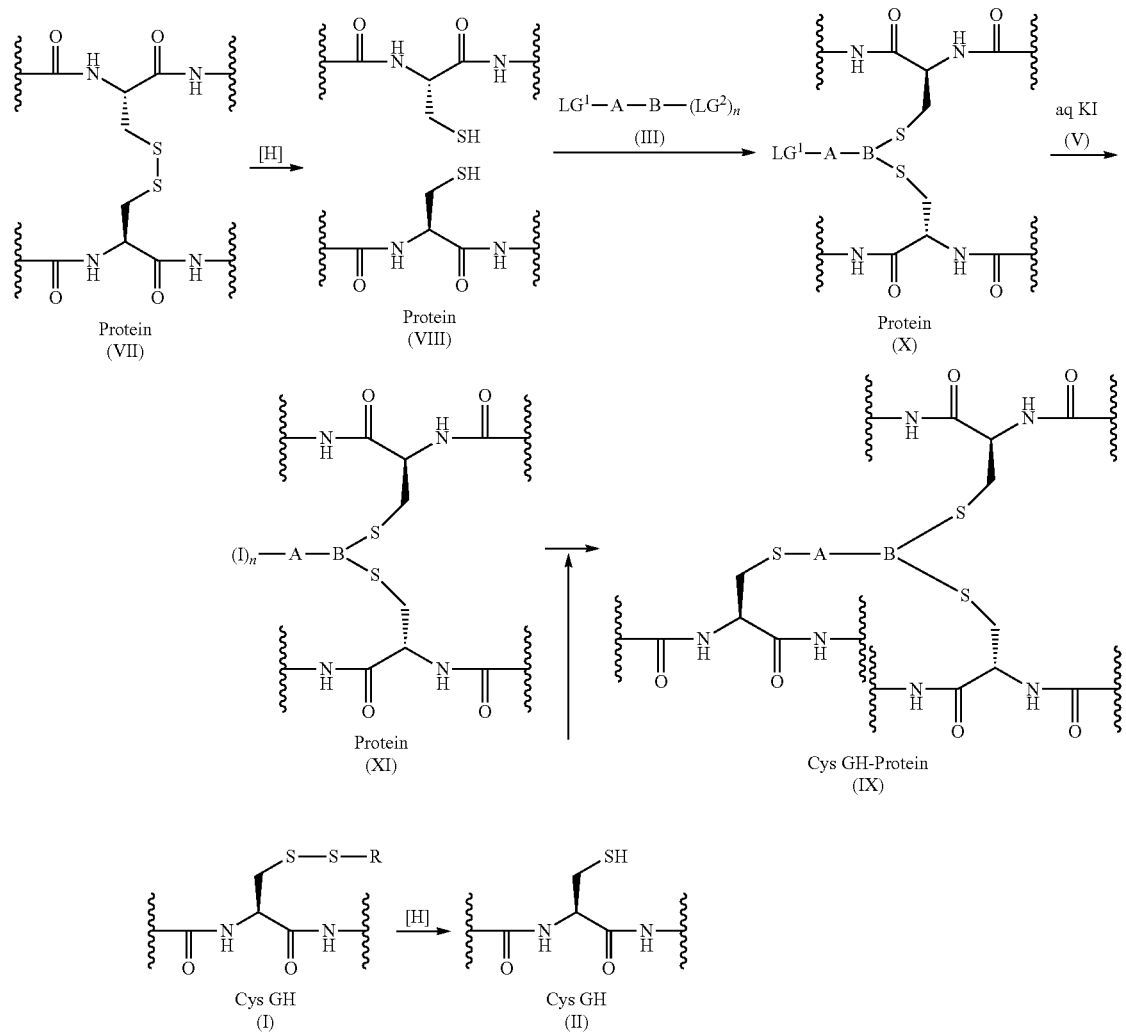

Reaction where linker is first attached to Fc subsequently to GH.

Wherein the cysteine residue in (I) optionally is protected as a mixed disulfide (GH-S-S-R) with R being a small organic moiety. Non limited examples of mixed disulphides may include disulfides between cysteamine (R=—CH$_2$CH$_2$NH$_2$); cysteine (R=—CH$_2$CH(C(=O)OH)NH$_2$); homocysteine (R=—CH$_2$CH$_2$CH(C(=O)OH)NH$_2$); and glutathione (R=—CH$_2$CH(C(=O)NH—CH$_2$C(=O)OH)NH—C(=O)CH$_2$CH$_2$CH(C(=O)OH)NH$_2$).

The conjugation process utilise a trivalent linker LG$^1$-A-B-(LG$^2$)$_2$ (III) wherein LG$^1$ and LG$^2$ independently represent inorganic leaving groups such as —Cl, —Br, —I and/or organic leaving groups such as mesylate or tosylate. Linker (III) is conjugated via nucleophilic substitution to reduced Protein (VIII) e.g. a Fc-domain obtained from (VII) via selective reduction of a disulphide bond (VII→VIII) using (DTT, TCEP, TPPTS, and TPPDS, or other reducing agents) affording LG$^1$-A-B-Protein conjugate (X). Selectivity for LG$^1$ versus LG$^2$ is obtained via utilization of difference in leaving group ability between LG$^1$ and LG$^2$. In order for LG$^1$ in compound (X) to act as a proper leaving group for the next coupling step, it is changed into iodo (XI) via an aqueous Finkelstein reaction with potassium iodine. Compound (XI) is then coupled with reduced GH (II) affording GH-A-B-Protein conjugate (IX).

The steps of the reaction may be described as follows starting from a GH compound (I) having an internal free Cys, a trivalent linker (III) and a Fc domain including a reducible disulfide bond.

1) Liberating free cysteines in an Fc-domain (VII) via selective reduction of a disulfide bridge with a suitable selective reducing agent affording (VIII)
2) Alkylation of the Fc-domain (VIII) with a trivalent linker (III) affording an LG$^1$-A-B-Fc conjugate intermediate (X)
3) Optionally liberating free Cys GH (II) via reduction of a mixed disulfide (I) with a suitable selective reducing agent
4) Activating leaving group LG$^1$ of intermediate (X) via an aqueous Finkelstein iodine exchange reaction (V) affording activated conjugate intermediate (XI)
5) Coupling of a free Cys GH (II) with an the activated conjugate intermediate (XI) affording a Cys conjugated GH-Fc-compound (IX)

Assays

Assay 1—GH Receptor Binding Assay

Receptor interaction of GH compounds is analysed using surface plasmon resonance (SPR) analysis. The method is general for the GH compounds.

The interaction of hGH and GH compounds with the hGH receptor via site 1 was studied by surface plasmon resonance using a Biacore T100 instrument (GE Healthcare, Sweden). Anti-hGH mAb (Fitzgerald Industries International, USA, #10G05B) was immobilized onto a CM-5 chip according to manufacturer's instruction at a level of typically 5000 RU. hGH or GH compounds are captured at 10-25 µg/mL in running buffer (10 mM HEPES, 0.15 M NaCl, 30 mM EDTA, 0.05% Surfactant P20, pH 7.4), which resulted in 250-400 RU captured ligand. hGHR at a concentration of 0-800 nmol was subsequently injected over the surface at 30 mL/min. A surface with immobilized anti-hGH mAb but without captured hGH was used as reference.

Kinetic data is analyzed with Biacore™ Evaluation Software 2.0 with the 1:1 Langmuir binding model.

Assay 2—BAF-3GHR Assay to Determine Growth Hormone Activity

The biological activity of hGH compounds is measured in a cell based receptor potency proliferation assay, namely a BAF assay. The BAF-3 cells (a murine pro-B lymphoid cell line derived from the bone marrow) was originally IL-3 dependent for growth and survival. IL-3 activates JAK-2 and STAT which are the same mediators GH is activating upon stimulation. After transfection of the human growth hormone receptor the cell line was turn into a growth hormone-dependent cell line. This clone can be used to evaluate the effect of different growth hormone samples on the survival of the BAF-3GHR.

The BAF-3GHR cells are grown in starvation medium (culture medium without growth hormone) for 24 hrs at 37° C., 5% C02.

The cells are washed and re-suspended in starvation medium and seeded in plates. 10 µL of human growth hormone and the growth hormone compound to be tested is used in different concentrations, and the plates are incubated for 68 hrs at 37° C., 5% C02.

AlamarBlue® is added to each well and the cells are then incubated for another 4 hrs. The AlamarBlue® is a redox indicator, and is reduced by reactions innate to cellular metabolism and, therefore, provides an indirect measure of viable cell number.

Finally, the metabolic activity of the cells is measure in a fluorescence plate reader. The absorbance in the samples is expressed in % of cells not stimulated with growth hormone compound or control and from the concentration-response curves the activity (amount of a compound that stimulates the cells with 50%) can be calculated.

Assay 3: Assay for Evaluating Pharmacokinetics Parameters of Growth Hormone Compounds in Normal Rats)

The pharmacokinetic of the compounds of the examples is investigated in male Sprague Dawley rats after intravenous (iv.) single dose administration.

Test compounds are diluted to a final concentration of 150 nmol/mL in a dilution buffer consisting of: Glycine 20 mg/mL, mannitol 2 mg/mL, NaHCO$_3$ 2.5 mg/mL, pH adjusted to 8.2.

The test compounds are studied in male Sprague Dawley rats weighing approximately 250 g. The test compounds are administered as a single injection either iv. in the tail vein with a 27 G needle at a predetermined dose such as of 15 nmol/rat in volume of 0.1 mL (concentration 150 nmol/mL) or approximately 60 nmol/kg body weight.

For each test compound blood sampling is conducted according to the following schedule:

| | | Time (h) | | | | | | | | | | | | |
|---|---|---|---|---|---|---|---|---|---|---|---|---|---|---|
| Animal | Predose | 0.08 | 0.5 | 1 | 2 | 4 | 6 | 8 | 18 | 24 | 48 | 72 | 96 | 168 | 240 | 336 |
| 1 | X | | | | X | | | | | X | | | X | | | |
| 2 | X | | | | X | | | | | X | | | X | | | |
| 3 | X | | | | X | | | | | X | | | X | | | |
| 4 | X | | X | | | X | | | | | X | | | X | | |
| 5 | X | | X | | | X | | | | | X | | | X | | |

|       |         | Time (h) | | | | | | | | | | | | | |
|-------|---------|------|-----|---|---|---|---|---|----|----|----|----|----|-----|-----|
| Animal | Predose | 0.08 | 0.5 | 1 | 2 | 4 | 6 | 8 | 18 | 24 | 48 | 72 | 96 | 168 | 240 | 336 |
| 6  |   | X |   |   |   | X |   |   |   | X |   |   | X |   |   |   |
| 7  |   |   | X |   |   |   | X |   |   |   | X |   |   |   | X |   |
| 8  |   |   | X |   |   |   | X |   |   |   | X |   |   |   | X |   |
| 9  |   |   | X |   |   |   | X |   |   |   | X |   |   |   | X |   |
| 10 |   |   |   | X |   |   |   | X |   |   |   | X |   |   |   | X |
| 11 |   |   |   | X |   |   |   | X |   |   |   | X |   |   |   | X |
| 12 |   |   |   | X |   |   |   | X |   |   |   | X |   |   |   | X |

At each sampling time 200 μL blood is drawn from the tail vein or the sublingual plexus using a 25 G needle. The blood is sampled into an EDTA coated test tube and stored on ice until centrifugation at 1200×G for 10 min at 4° C. Two times 50 μL plasma is transferred to two separate Micronic tubes and stored at −20° C. until analysis.

Test substance concentrations will be determined by Luminescence Oxygen Channeling Immunoassay (LOCI), which is a homogenous bead based assay. LOCI reagents include two latex bead reagents and biotinylated GH binding protein, which is one part of the sandwich. One of the bead reagents is a generic reagent (donor beads) and is coated with streptavidin and contains a photosensitive dye. The second bead reagent (acceptor beads) is coated with an antibody making up the sandwich. During the assay the three reactants combine with analyte to form a bead-aggregate-immune complex. Illumination of the complex releases singlet oxygen from the donor beads which channels into the acceptor beads and triggers chemiluminescence which is measured in the EnVision plate reader. The amount of light generated is proportional to the concentration of hGH derivative. 2 μL 40× in LOCI buffer diluted sample/calibrator/control is applied in 384-well LOCI plates. 15 μL of a mixture of biotinylated GH binding protein and mAb M94169 anti-(hGH) conjugated acceptor-beads is added to each well (21-22° C.). The plates are incubated for 1 hour at 21-22° C. 30 μL streptavidin coated donor-beads (67 μg/mL) is added to each well and all is incubated for 30 minutes at 21-22° C. The plates are read in an Envision plate reader at 21-22° C. with a filter having a bandwidth of 520-645 nmol after excitation by a 680 nmol laser. The total measurement time per well is 210 ms including a 70 ms excitation time. The limit of detection for growth hormone compounds is 50 pM. A non-compartmental pharmacokinetic analysis is performed on mean concentration-time profiles of each test compound using WinNonlin Professional (Pharsight Inc., Mountain View, Calif., USA). The pharmacokinetic parameter estimates of terminal half-life ($T_{1/2}$) and mean residence time (MRT) are calculated. IGF-1 Plasma concentration-time profiles are generated for each compound.

Assay 4: Assay for Evaluating the In Vivo Response of Growth Hormone Compounds in Hypophysectomised Sprague Dawley Rats.

The in vivo response is studied in hypophysectomised male Sprague Dawley rats. The hypophysectomised rat is a well-known and recognised animal model of growth hormone deficiency, where no production of growth hormone occurs after the surgical removal of the pituitary gland. This also leads to low circulating levels of insulin-like growth factor-1 (IGF-1) another important clinical feature of growth hormone deficiency in humans.

The hypophysectomy is usually performed on 4 week old male rats weighing 90-100 g. The animals entering the study 3-4 weeks after the surgery weighing 100-110 g. Animals with a body weight gain of more than 10% during the 3-4 weeks after surgery are not allowed to enter the study.

Hypophysectomy Procedure

Anaesthesia and Pre-Operative Analgesia

The rats are anaesthetised with fentanyl-fluanisone (Hypnorm 0.315 mg fentanyl and 10 mg fluanisone per mL) and midazolam (Midazolam Accord 5 mg midazolam per ml). The rats are dosed i.p. 2 mL/kg with a mixture of fentanyl-fluanisone and midazolam diluted in sterile water. The resulting mixture contains 0.079 mg fentanyl, 2.5 mg fluanisone and 1.25 mg midazolam per mL.

Surgical Procedure

The rats are prepared for aseptic surgery. The rats are mounted in the Hoffman-Reiter stereotactic device designed for the hypophysectomy procedure.

An 18G needle on a glass syringe is introduced into the right ear of the rat. During a rotating movement the needle passes through the tympanic membrane, middle ear and temporal bone. From this position the pituitary gland is aspirated.

The rat is dismounted from the stereotactic device and transferred to a thermo plate for recovery. When the rat recovers it will be transferred to its cage.

Post-Operative Analgesia and Care

Before recovery the rat is treated with carprofen sc. (Rimadyl 50 mg carprofen per mL) 1 mL/kg with a solution containing 5 mg carprofen per mL diluted in sterile water. Post-operative analgesia is sustained for 2 days after surgery by adding 0.05 mg carprofen per ml to a 5% dextrose solution which is provided to the rat instead of drinking water. After the first 2 days post-surgery the rat will be provided with at 5% dextrose solution as drinking water for up to 10-14 days post-surgery.

Hypophysectomised Sprague Dawley rats were randomly allocated to different dosing groups with ten animals in each group. One group received vehicle only and served as a control group. In all test groups each animal received a single sc. dose of 1, 5, 15, 50 and 150 nmol test compound respectively. The body weight was measured daily during the study between 8-10 am. Blood sampling for exposure and IGF-1 measurements were conducted at day 0, 1, 3, 5, 7, 10 and 14 between 8-10 am.

At each sampling time 200 μL blood is drawn from the tail vein or the sublingual plexus using a 25 G needle. The blood is sampled into an EDTA coated test tube and stored on ice until centrifugation at 1200×G for 10 min at 4° C. 50 μL plasma is transferred to a Micronic tube and stored at −20° C. until analysis. IGF-1 concentration-time profiles are generated for each compound.

Assay 5: Assay for Detecting IGF Response in Rats.

The plasma IGF-1 concentrations is determined by a commercial ELISA assay (Commercial assay from Immunodiagnostic Systems Ltd. Octeia Rat/Mouse IGF-1, Cat. no. AC-18F1 IDS Ltd., England). The assay is a sandwich ELISA using a highly IGF-1 specific polyclonal antibody as catcher, and a horseradish peroxidase labelled high affinity monoclonal antibody as detector. The assay lower limit of detection is 63 ng/mL. IGF-1 plasma concentration-time profiles are generated for each compound together with baseline corrected IGF-1 plasma concentration-time profiles. The time and extent the baseline corrected profile is above zero is used as a measure for the compound efficacy.

Assay 6: Assay for Evaluating Pharmacokinetics Parameters of Growth Hormone Compounds in Minipigs.

The pharmacokinetic of the compounds of the examples is investigated in female Göttingen minipigs after subcutaneous (sc.) single dose administration. Test compounds are diluted to a final concentration of 15 mg/mL in a dilution buffer consisting of: Glycine 20 mg/mL, mannitol 2 mg/mL, $NaHCO_3$ 2.5 mg/mL, pH adjusted to 8.2. The test compounds are studied in female Göttingen minipigs weighing approximately 10-12 kg.

The test compounds were administered as a single subcutaneous injection on the right side of the neck, approximately 5-7 cm from the ear and 7-9 cm from the middle of the neck. The injections were given with a stopper on the 21 G needle, allowing 0.5 cm of the needle to be introduced. Each animal received a dose of 20 nmol/kg in a dosing volume of 0.1 mL/kg.

For each test compound blood sampling was conducted from each animal according to the following schedule: Predose, 1, 4, 12, 24, 36, 48, 72, 96, 168, 240, 336, 504, 672, 840, and 1008 hours after dosing. Blood samples of 2 mL were collected from unanaesthetised minipigs by use of Vacutainers inserted in V. Jugularis into EDTA tubes. Immediately after blood collection the tubes were inverted gently in order to ensure sufficient mixing. The blood was kept on ice for max. 10 min before centrifugation at 1500 g for ten min at 4° C. Two hundred μL plasma was pipetted into Micronic tubes for compound concentration determination, and 200 μL plasma was be pipetted into Micronic tubes for IGF-1 determination. The plasma samples were stored at −20° C. until analysis.

Test substance concentrations were determined by Luminescence Oxygen Channeling Immunoassay (LOCI), which is a homogenous bead based assay. LOCI reagents include two latex bead reagents and biotinylated GH binding protein, which is one part of the sandwich. One of the bead reagents is a generic reagent (donor beads) and is coated with streptavidin and contains a photosensitive dye. The second bead reagent (acceptor beads) is coated with an antibody making up the sandwich. During the assay the three reactants combine with analyte to form a bead-aggregate-immune complex. Illumination of the complex releases singlet oxygen from the donor beads which channels into the acceptor beads and triggers chemiluminescence which is measured in the EnVision plate reader. The amount of light generated is proportional to the concentration of GH derivative. 2 μL 40× in LOCI buffer diluted sample/calibrator/control is applied in 384-well LOCI plates. 15 μL of a mixture of biotinylated GH binding protein and mAb M94169 anti-(hGH) conjugated acceptor-beads is added to each well (21-22° C.). The plates are incubated for 1 hr at 21-22° C. 30 μL streptavidin coated donor-beads (67 μg/mL) is added to each well and all is incubated for 30 min at 21-22° C. The plates are read in an Envision plate reader at 21-22° C. with a filter having a bandwidth of 520-645 nmol after excitation by a 680 nmol laser. The total measurement time per well is 210 ms including a 70 ms excitation time. The limit of detection for growth hormone compounds is 50 pM.

A non-compartmental pharmacokinetic analysis was performed on mean concentration-time profiles of each test compound using WinNonlin Professional (Pharsight Inc., Mountain View, Calif., USA). The pharmacokinetic parameter estimates of terminal half-life ($T_{1/2}$) and mean residence time (MRT) were calculated.

Example 1

Trivalent Linker 1

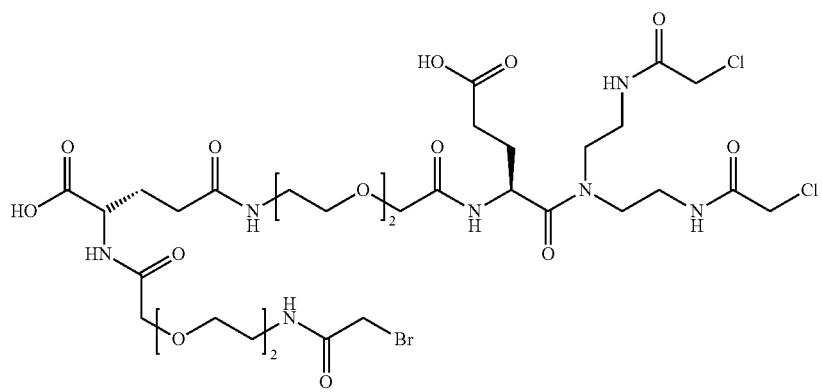

(4S,18S)-4-(bis(2-(2-Chloroacetamido)ethyl)carbamoyl)-18-(2-(2-(2-(2-bromoacetamido)ethoxy)ethoxy)acetamido)-6,15-dioxo-8,11-dioxa-5,14-diazanonadecanedioic acid
Reaction scheme:
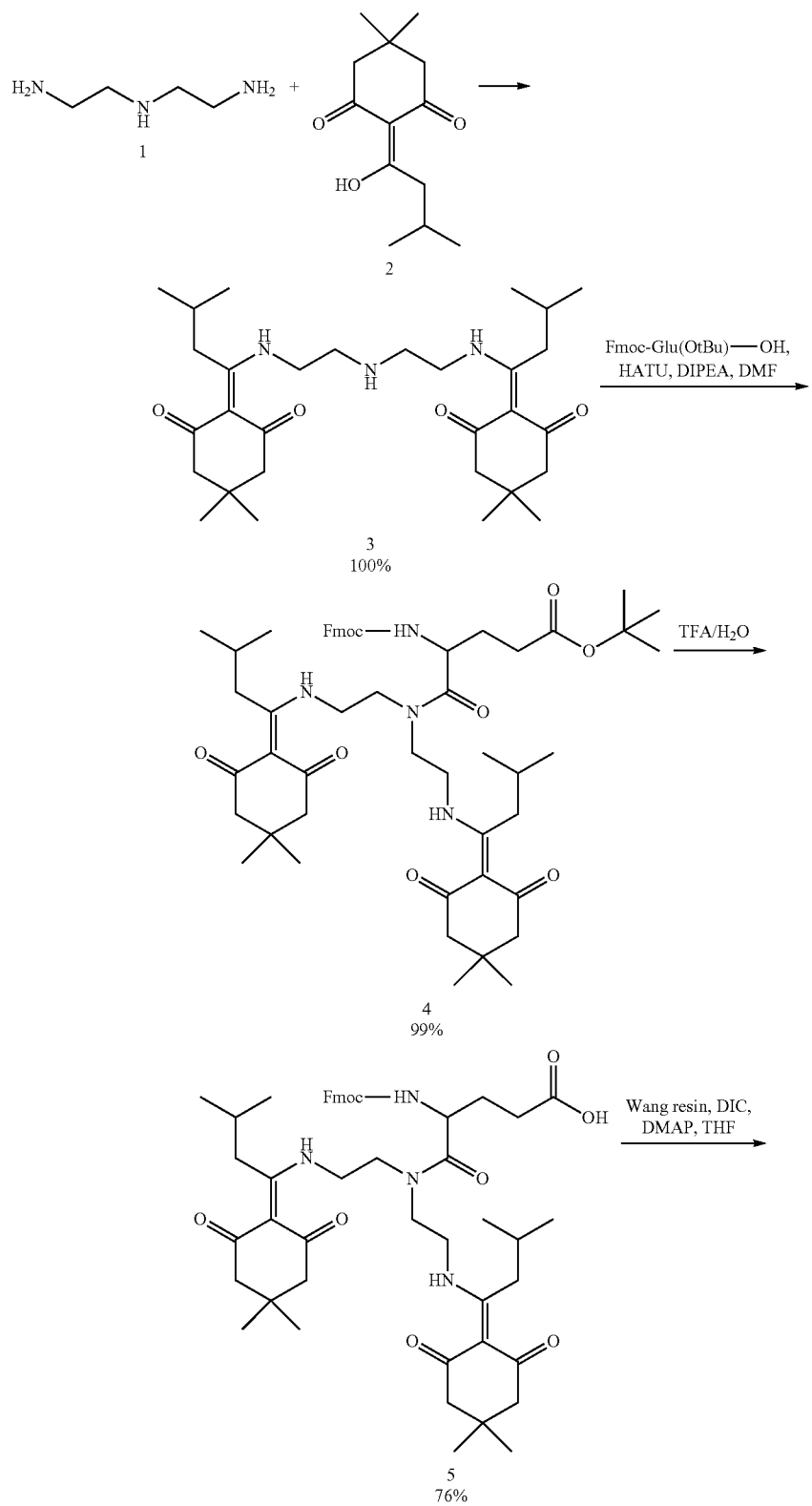

-continued

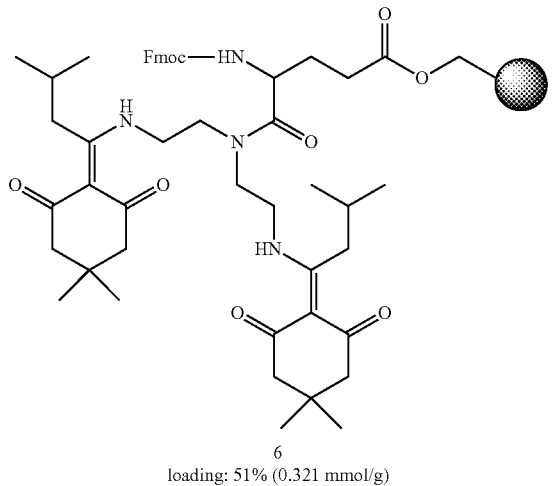

6
loading: 51% (0.321 mmol/g)

1. Fmoc-deprotection, 20% piperidine in DMF
2. Fmoc—OEG—OH, TCTU, DIPEA, DMF
3. Fmoc-deprotection, 20% piperidine in DMF
4. Fmoc-Glu(OH)—OtBu, TCTU, DIPEA, DMF
5. Fmoc-deprotection, 20% piperidine in DMF
6. Fmoc—OEG—OH, TCTU, DIPEA, DMF
7. Fmoc-deprotection, 20% piperidine in DMF 8. Mtt-Cl, DIPEA, DCM
9. ivDde-deprotection, 2% $N_2H_4$ monohydrate in DMF
10. $ClCH_2COOH$, PyBroP, DIPEA, DMF
11. Mtt-deprotection, 80% HFIP in DCM
12. $BrCH_2COOH$, DIC, DMF
13. Cleavage from resine, TFA/TIS/$H_2O$ (95:2.5:2.5)

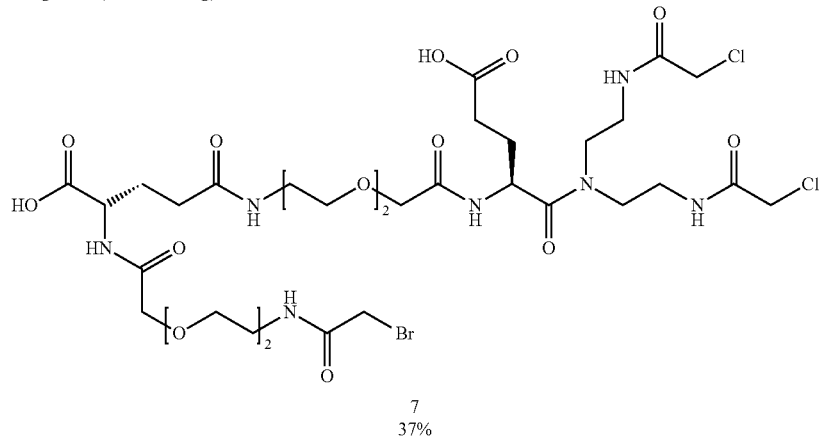

7
37%

Synthetic Protocol:

The solution of 2-(1-hydroxy-3-methylbutylidene)-5,5-dimethylcyclohexane-1,3-dione (2) (37.7 g, 168 mmol) in DCM (200 mL) was added dropwise to a solution of diethylenetriamine (1) (8.64 mL, 80.0 mmol) in DCM (130 mL). The reaction mixture was stirred overnight, then solvent was evaporated giving 2,2'-(((azanediylbis(ethane-2,1-diyl))bis(azanediyl))bis(3-methylbutan-1-yl-1-ylidene))bis(5,5-dimethylcyclohexane-1,3-dione) (3) as pale yellow oil.

Yield: 41.2 g (100%).

$^1$H NMR spectrum (300 MHz, CDCl$_3$, δ$_H$): 3.57 (q, 4H); 3.06-2.89 (m, 8H); 2.36 (bs, 8H); 2.05-1.89 (m, 2H); 1.09-0.94 (m, 26H).

The solution of the above amine (3) (33.4 g, 64.8 mmol) in DMF (320 mL) was added to a solution of 2-(9H-fluoren-9-ylmethoxycarbonylamino)-pentanedioic acid 5-tert-butyl ester (Fmoc-Glu(OtBu)-OH, 63.4 g, 149 mmol), HATU (56.6 g, 149 mmol), DIPEA (40.0 mL, 227 mmol) in DMF (530 mL). The reaction mixture was stirred at room temperature overnight. Then EtOAc (1.6 L) and water (1.6 L) were added. Separated organic layer was washed with aqueous solution of 10% K$_2$CO$_3$ (2×1.6 L), dried over anhydrous Na$_2$SO$_4$, filtered and evaporated in vacuo. The residue was purified by flash column chromatography (Silicagel 60, 0.063-0.040 mm; eluent: DCM/MeOH 50:1-40:1) to give tert-butyl 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoate (4) as pale yellow viscous oil.

Yield: 59.2 g (99%).

$^1$H NMR spectrum (300 MHz, CDCl$_3$, δ$_H$): 7.77 (d, J=7.5 Hz, 2H); 7.59 (m, 2H); 7.40 (t, J=7.5 Hz, 2 Hz); 7.36-7.26 (m, 2H); 5.65 (d, J=9.2 Hz, 1H); 4.72-4.59 (m, 1H); 4.46-4.27 (m, 2H); 4.24-4.16 (m, 1H); 4.12-3.99 (m, 1H); 3.94-3.53 (m, 6H); 3.48-3.33 (m, 1H); 2.97 (bs, 4H); 2.46-2.26 (m, 10H); 2.08-1.83 (m, 4H); 1.79-1.64 (m, 1H); 1.43 (s, 9H); 1.07-0.90 (m, 24H). tert-Butyl 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoate (4) (59.2 g, 64.8 mmol) dissolved in DCM (50 mL) was added to TFA/water mixture (95:5, 400 mL) and stirred for 2 hrs. Then solvent was evaporated and residue was co-evaporated with toluene for three times. The residue was dissolved in DCM (800 mL) and washed with water (3×800 mL). The solvent was evaporated under reduced pressure. The residue was purified by column chromatography (Silicagel 60, 0.063-0.040 mm; eluent: DCM/MeOH 60:1-10:1) to give 4-((((9H-fluoren-9-yl)methoxy)carbonyl)amino)-5-(bis(2-((1-(4,4-dimethyl-2,6-dioxocyclohexylidene)-3-methylbutyl)-amino)ethyl)amino)-5-oxopentanoic acid (5) as white powder.

Yield: 42.1 g (76%).

$^1$H NMR spectrum (300 MHz, AcOD-d$_4$, 80° C., δ$_H$): 7.79 (d, J=7.3 Hz, 2H); 7.64 (d, J=7.5 Hz, 2H); 7.39 (t, J=7.4 Hz, 2H); 7.36-7.26 (m, 2H); 4.83 (bs, 1H); 4.48-4.30 (m, 2H); 4.27-4.19 (m, 1H); 4.19-3.62 (m, 7H); 3.61-3.46 (m, 1H); 3.28-2.90 (m, 4H); 2.55 (t, J=6.7 Hz, 2H); 2.43 (s, 8H); 2.01-1.81 (m, 4H); 1.07-0.88 (m, 24H).

Wang resin 0.63 mmol/g (25.7 g, 16.2 mmol) was left to swell in THF (250 mL) for 20 min. A solution of the 4-((((9H-fluoren-9-yl)methoxy)carbonyl)amino)-5-(bis(2-((1-(4,4-dimethyl-2,6-dioxocyclohexylidene)-3-methyl-butyl)amino)ethyl)amino)-5-oxopentanoic acid (5) (42.0 g, 48.5 mmol) in THF (250 mL) was added to resin and then DIC (7.60 mL, 48.5 mmol) and 4-dimethylaminopyridine (DMAP, 200 mg, 1.62 mmol). The mixture was shaken for 18 hrs. Resin was filtered and washed with DCM (6×250 mL). Resin was treated by solution of acetic anhydride (40 mL), pyridine (40 mL) in DMF (360 mL) for 15 min and washed with DCM (6×250 mL) to give compound (6) as yellow solid.

Yield: 36.0 g.

Loading: 51% (0.321 mmol/g).

The above compound (6) (6.27 g, 2.01 mmol) was left to swell in DCM (50 mL) for 20 min. Fmoc group was removed by treatment with 20% piperidine in DMF (1×5 min, 1×30 min, 2×30 mL). Resin was washed with DMF (3×30 mL), 2-propanol (3×30 mL) and DCM (3×30 mL). A solution of {2-[2-(9H-fluoren-9-ylmethoxycarbonylamino)-ethoxy]-ethoxy}-acetic acid (Fmoc-OEG-OH, 1.25 g, 3.24 mmol), O-(6-chloro-benzotriazol-1-yl)-N,N,N',N'-tetramethyluronium tetrafluoroborate (TCTU, 1.15 g, 3.24 mmol) and DIPEA (1.13 mL, 6.48 mmol) in DMF (35 mL) was added to resin and the mixture was shaken for 3 hrs. Resin was filtered and washed with DMF (3×30 mL), DCM (3×30 mL) and DMF (3×30 mL). Fmoc group was removed by treatment with 20% piperidine in DMF (1×5 min, 1×30 min, 2×30 mL). Resin was washed with DMF (3×30 mL), 2-propanol (3×30 mL) and DCM (3×30 mL). Solution of (S)-2-(9H-fluoren-9-ylmethoxycarbonylamino)-pentanedioic acid 1-tert-butyl ester (Fmoc-LGlu-OtBu, 1.38 g, 3.24 mmol), O-(6-chloro-benzotriazol-1-yl)-N,N,N',N'-tetramethyluronium tetrafluoroborate (TCTU, 1.15 g, 3.24 mmol) and DIPEA (1.13 mL, 6.48 mmol) in DMF (35 mL) was added to resin and mixture was shaken for 2 hrs. Fmoc group was removed by treatment with 20% piperidine in DMF (1×5 min, 1×30 min, 2×30 mL). Resin was washed with DMF (3×30 mL), 2-propanol (3×30 mL) and DCM (3×30 mL). A solution of {2-[2-(9H-fluoren-9-ylmethoxycarbonylamino)-ethoxy]-ethoxy}-acetic acid (Fmoc-OEG-OH, 1.25 g, 3.24 mmol), O-(6-chloro-benzotriazol-1-yl)-N,N,N',N'-tetramethyluronium tetrafluoroborate (TCTU, 1.15 g, 3.24 mmol) and DIPEA (1.13 mL, 6.48 mmol) in DMF (35 mL) was added to resin and the mixture was shaken for 3.5 hrs. Resin was filtered and washed with DMF (3×30 mL), DCM (3×30 mL) and DMF (3×30 mL). Fmoc group was removed by treatment with 20% piperidine in DMF (1×5 min, 1×30 min, 2×30 mL). Resin was washed with DMF (3×30 mL), 2-propanol (3×30 mL) and DCM (3×30 mL).

A solution of 1-(chloro-diphenyl-methyl)-4-methyl-benzene (MttCl, 2.02 g, 6.90 mmol) and DIPEA (2.55 mL, 14.6 mmol) in dry DCM (50 mL) was added to resin and mixture was shaken for 2 hrs. Resin was filtered and washed with DCM (4×30 mL) and DMF (4×30 mL). IvDde group was removed by treatment with 2% hydrazine monohydrate in DMF (3×30 mL, 3×3 min). Resin was washed with DMF (8×30 mL). A solution of chloroacetic acid (0.92 g, 9.74 mmol), bromo-tris-pyrrolidino-phosphonium hexafluorophosphate (PyBrOP, 4.54 g, 9.74 mmol) and DIPEA (3.39 mL, 19.5 mmol) in DMF (60 mL) was added to resin and mixture was shaken for 3 hrs. Resin was filtered and washed with DMF (4×30 mL), DCM (4×30 mL), DMF (4×30 mL), DCM (10×30 mL). Mtt group was removed by treatment with 80% 1,1,1,3,3,3-hexafluoro-2-propanol in DCM (4×30 mL, 2×10 min, 2×30 min). Resin was washed with DCM (5×30 mL) and DMF (4×30 mL). A solution of bromoacetic acid (4.50 g, 32.4 mmol) and DIC (4.27 mL, 27.6 mmol) in DMF (50 mL) was added to resin and mixture was shaken for 25 min. Resin was filtered and washed with DMF (4×30 mL), MeCN (2×30 mL) and DCM (10×30 mL). The product was cleaved from resin by treatment with cleavage cocktail of TFA/TIS/H$_2$O (95:2.5:2.5, 50 mL) for 2 hrs. Resin was filtered and washed with TFA/DCM mixture (1:1, 50 mL) and DCM (10×50 mL). Solutions were combined and solvents were evaporated to dryness. The solvent was co-evaporated with toluene for three times. The residue was purified by Column X-Bridge3 C18, OBD, 5 μm, 50×250 mm (Mobile Phase: A=0.05% TFA/H$_2$O, B=0.05% TFA/MeCN, gradient: 5% to 35%) to give (4S,18S)-4-(bis(2-(2-chloroacetamido)ethyl)carbamoyl)-18-(2-(2-(2-(2-bromoacetamido)ethoxy)-ethoxy)acetamido)-6,15-dioxo-8,11-dioxa-5,14-diazanonadecanedioic acid (7) as white solid.

Yield: 694 mg (37%).

$^1$H NMR spectrum (300 MHz, AcOD-d$_4$, 80° C., $\delta_H$): 5.13 (dd, J=9.3 Hz, J=4.2 Hz, 1H); 4.68 (dd, J=8.3 Hz, J=5.3 Hz, 1H); 4.20-4.06 (m, 8H); 3.95 (s, 2H); 3.91-3.41 (m, 24H); 2.61-2.08 (m, 7H); 2.08-1.88 (m, 1H).

LC-MS purity: 100%.

LC-MS Rt (Kinetex 4.6 mm×50 mm, MeCN/water 5:95 to 100:0+0.1% FA): Rt=4.74 min.

LC-MS m/z: 926.6 (M+H)$^+$.

UPLC purity: 97.5% (214 nm).

UPLC Rt (Acquity UPLC BEHC 18, 1.7 μm, 2.1×150 mm; MeCN/water 5:95 to 95:5+0.05% TFA): Rt=1.64 min.

Trivalent Linker 2

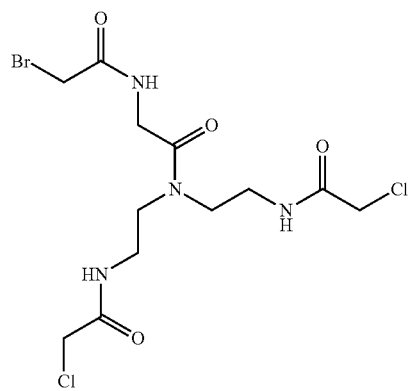 [SMILES: O=C(CCl)NCCN(CCNC(=O)CCl)C(=O)CNC(=O)CBr]

2-(2-Bromoacetamido)-N,N-bis(2-(2-chloroacetamido)ethyl)acetamide

Reaction scheme:

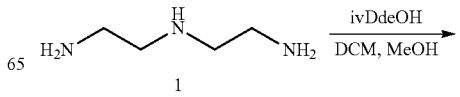

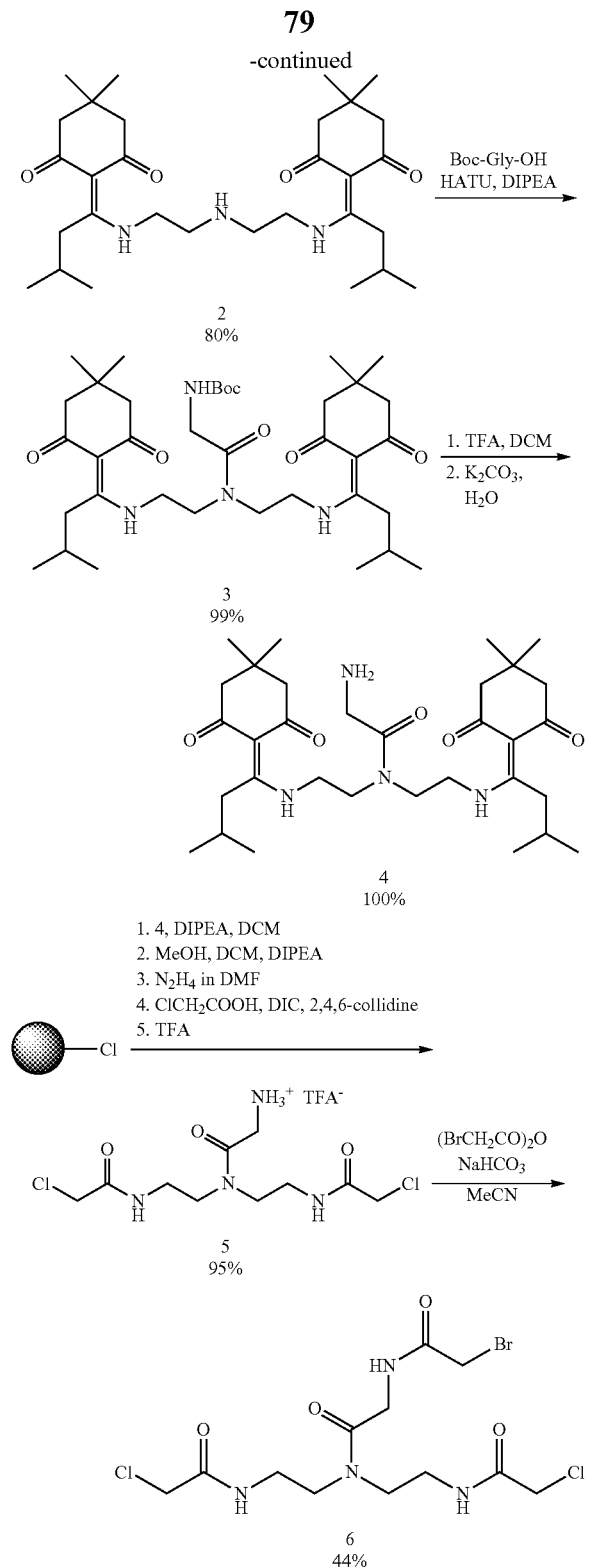

Synthetic Protocol:

Solution of 2-(1-hydroxy-3-methylbutylidene)-5,5-dimethylcyclohexane-1,3-dione (44.9 g, 200 mmol) in MeOH (400 mL) was added to diethylenetriamine (1) (DETA, 10.3 g, 100 mmol) in DCM (1.50 L) within 40 min. The reaction mixture was stirred overnight. The solvents were removed under reduced pressure and crude product was purified by flash column chromatography (Silicagel 60, 0.040-0.063 mm; eluent: DCM/MeOH 25/1) giving pure compound (2) as yellowish waxy solid.

Yield: 41.0 g (80%).

$^1$H NMR spectrum (300 MHz, CDCl$_3$, δ$_H$): 13.83 (bs, 2H); 3.57 (q, J=5.7 Hz, 4H); 3.10-2.91 (m, 8H); 2.36 (bs, 8H); 1.97 (sep, J=6.8 Hz, 2H); 1.05-0.96 (m, 24H).

To a solution of the above compound (2) (3.09 g, 6.00 mmol) was added a mixture of (tert-butoxycarbonyl)glycine (BocGlyOH, 2.10 g, 12.0 mmol), HATU (4.56 g, 12.0 mmol), and DIPEA (4.19 mL, 3.10 g, 24.0 mmol) in the mixture of DCM (200 mL) and DMF (40 mL). The reaction mixture was allowed to stirred for 2 hrs. Then 1M aqueous solution of potassium carbonate (200 mL) was added. The organic phase was separated and washed with 1M solution of hydrochloric acid (200 mL) and dried over anhydrous Na$_2$SO$_4$. The solvent was removed under reduced pressure. The residue was purified by flash column chromatography (Silicagel 60, 0.040-0.063 mm; eluent: EtOAc) giving pure compound (3) as brownish viscous oil.

Yield: 3.98 g (99%).

RF (SiO$_2$, EtOAc): 0.50.

$^1$H NMR spectrum (300 MHz, CDCl$_3$, δ$_H$): 14.03 (bs, 1H); 13.87 (bs, 1H); 5.43 (bs, 1H); 4.01 (d, J=4.7 Hz, 2H); 3.79-3.56 (m, 8H); 3.06-2.89 (m, 4H); 2.48-2.27 (m, 8H); 1.95 (sep, J=6.8 Hz, 2H); 1.45 (s, 9H); 1.05-0.95 (m, 24H).

The above compound (3) (3.98 g, 5.91 mmol) was dissolved in DCM (5 mL) and TFA (30 mL) was added. After 2 hrs the volatiles were removed under reduced pressure and saturated aqueous solution of potassium carbonate was added (60 mL). The product was extracted with EtOAc (3×40 mL). The organic phase was dried over anhydrous Na$_2$SO$_4$ and the solvent was removed under reduced pressure giving pure compound (4) as off-white solid foam.

Yield: 3.38 g (100%).

$^1$H NMR spectrum (300 MHz, CDCl$_3$, δ$_H$): 14.01 (s, 1H); 13.88 (s, 1H); 3.80-3.70 (m, 2H); 3.68-3.58 (m, 6H); 3.52 (s, 2H); 3.06-2.93 (m, 4H); 2.45-2.29 (m, 8H), 1.95 (sep, J=6.8 Hz, 2H); 1.06-0.95 (m, 24H).

2-Chlorotrityl resin 100-200 mesh 1.8 mmol/g (4) (2 g, 7.43 mmol) was left to swell in dry DCM (100 mL) for 20 min. A solution of above compound (4) (2.83 g, 4.95 mmol) and DIPEA (3.28 mL, 18.8 mmol) in dry DCM (60 mL) was added to resin and the mixture was shaken overnight. Resin was filtered and treated with a solution of DIPEA (1.73 mL, 9.90 mmol) in MeOH/DCM mixture (4:1, 100 mL, 2×5 min). Then resin was washed with DMF (3×90 mL), 2-propanol (2×90 mL) and DCM (3×90 mL). The protecting groups were removed by treatment with hydrazine monohydrate (2% solution in DMF, 3×90 mL, 3×5 min). Then resin was washed with DMF (3×90 mL), 2-propanol (2×90 mL) and DCM (3×90 mL). Solution of chloroacetic acid (3.74 g, 39.6 mmol), 2,4,6-collidine (7.83 mL, 59.4 mmol) and DIC (6.13 mL, 39.6 mmol) in DMF (70 mL) was added to resin and mixture was shaken for 45 min. Resin was filtered and washed with DMF (4×90 mL), 2-propanol (2×90 mL) and DCM (8×90 mL). The product was cleaved from resin by treatment with cleavage cocktail (50% TFA in DCM, 80 mL) for 1 hour. Resin was filtered off and washed with DCM (3×40 mL). Solutions were combined and solvents were evaporated to dryness giving the desired compound (5) as thick brownish oil.

Yield: 2.01 g (95%).

$^1$H NMR spectrum (300 MHz, AcOD-d$_4$, δ$_H$): 4.23 (s, 2H); 4.19 (s, 2H); 4.16 (s, 2H); 3.71-3.51 (m, 8H).

Mixture of sodium bicarbonate (1.58 g, 18.8 mmol) and bromoacetic anhydride (1.71 g, 6.59 mmol) in MeCN (20 mL) was added to a solution of above compound (5) (2.01 g, 4.71 mmol) in MeCN (20 mL). After 90 min the reaction mixture was filtered through sintered glass and the solvent was removed under reduced pressure. The residue was purified by HPLC (Column X-Bridge4 C18, OBD, 5 μm, 50×250 mm, MeCN/H$_2$O 5:95 to 45:55+0.05% TFA). Resulting solution was freeze-dried to give the title compound as colourless viscous oil. Addition of MeCN (8 mL) led to the formation of colourless crystals and the solvent was removed under reduced pressure affording 2-(2-bromo-acetamido)-N,N-bis(2-(2-chloroacetamido)ethyl)acetamide (6) as colourless solid.

Yield: 900 mg (44%).

$^1$H NMR spectrum (300 MHz, AcOD-d$_4$, δ$_H$): 4.27 (s, 2H); 4.19 (s, 2H); 4.13 (s, 2H); 4.02 (s, 2H); 3.70-3.50 (m, 8H).

LC-MS purity: 100%.

LC-MS Rt (Kinetex 4.6 mm×50 mm, MeCN/water 5:95 to 100:0+0.1% FA): 2.90 min.

LC-MS m/z: 433.0 (M+H)$^+$.

Trivalent Linker 3

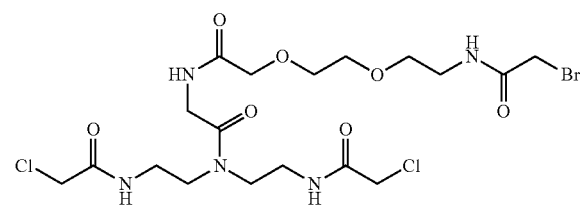 [SMILES: O=C(CCl)NCCN(CCNC(=O)CCl)C(=O)CNC(=O)COCCOCCNC(=O)CBr]

2-(2-(2-(2-(2-Bromoacetamido)ethoxy)ethoxy)acetamido)-N,N-bis(2-(2-chloroacetamido)ethyl)acetamide Reaction scheme:

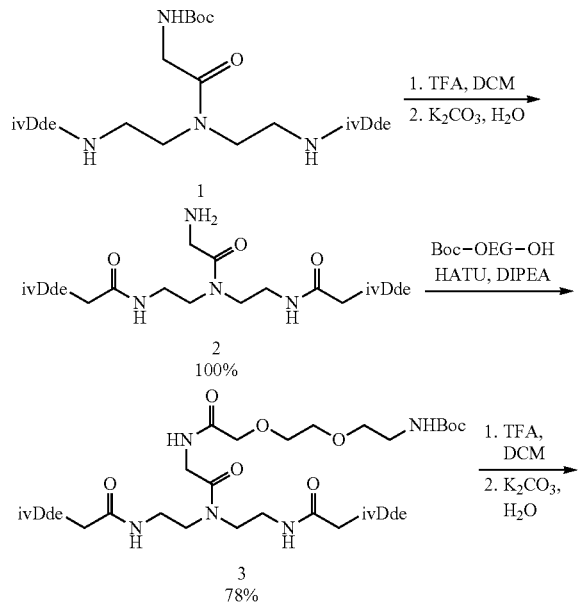

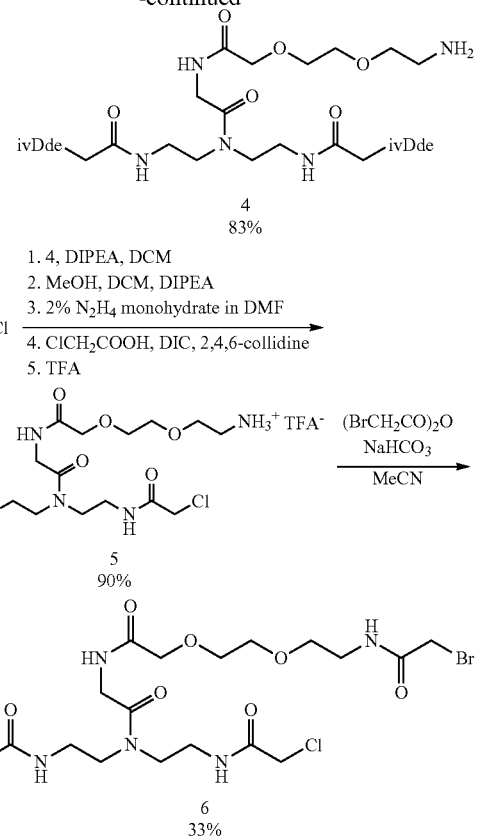

Synthetic Protocol:

TFA (30 mL) was added to a solution of tert-butyl (2-(bis(2-((1-(4,4-dimethyl-2,6-dioxocyclohexylidene)-3-methylbutyl)amino)ethyl)amino)-2-oxoethyl)carbamate (1) (3.98 g, 5.91 mmol, prepared as described in Example 2, compound (3)) in DCM (5 mL). After 2 hrs the volatiles were removed under reduced pressure and saturated aqueous solution of potassium carbonate was added (60 mL). The product was extracted with EtOAc (3×40 mL). The organic phase was dried over anhydrous Na$_2$SO$_4$ and the solvent was removed under reduced pressure giving pure compound (2) as off-white solid foam.

Yield: 3.38 g (100%).

$^1$H NMR spectrum (300 MHz, CDCl$_3$, δ$_H$): 14.01 (s, 1H); 13.88 (s, 1H); 3.80-3.70 (m, 2H); 3.68-3.58 (m, 6H); 3.52 (s, 2H); 3.06-2.93 (m, 4H); 2.45-2.29 (m, 8H); 1.95 (sep, J=6.8 Hz, 2H); 1.06-0.95 (m, 24H).

To a solution of the above compound (2) (2.84 g, 4.97 mmol) was added a mixture of 2,2-dimethyl-4-oxo-3,8,11-trioxa-5-azatridecan-13-oic acid (Boc-OEG-OH, 1.31 g, 4.97 mmol), HATU (1.89 g, 4.97 mmol), and DIPEA (1.74 mL, 9.94 mmol) in DCM (200 mL) and DMF (30 mL). The reaction mixture was allowed to stir overnight. Then 1M aqueous solution of potassium carbonate (200 mL) was added. The organic phase was separated and washed with 1M solution of hydrochloric acid (200 mL) and dried over anhydrous Na$_2$SO$_4$. The solvent was removed under reduced pressure. The residue was purified by flash column chromatography (Silicagel 60, 0.040-0.063 mm; eluent: DCM/MeOH 20:1) giving pure compound (3) as brownish viscous oil.

Yield: 3.19 g (78%).

RF (SiO$_2$ DCM/MeOH 20:1): 0.15.

$^1$H NMR spectrum (300 MHz, CDCl$_3$, δ$_H$): 14.06 (bs, 1H); 13.91 (bs, 1H); 7.66 (bs, 1H); 5.45 (bs, 1H); 4.19 (d, J=4.7 Hz, 2H); 4.05 (s, 2H); 3.79-3.62 (m, 12H); 3.57 (t, J=5.1 Hz, 2H); 3.38-3.29 (m, 2H); 3.04-2.92 (m, 4H); 2.45-2.27 (m, 8H); 1.93 (sep, J=6.8 Hz, 2H); 1.43 (s, 9H); 1.05-0.94 (m, 24H).

TFA (30 mL) was added to a solution the above compound (3) (3.19 g, 3.89 mmol) in DCM (5 mL). After 2 hrs the volatiles were removed under reduced pressure and 1M aqueous solution of sodium hydroxide was added (60 mL). The product was extracted with ethyl acetate (7×30 mL). The organic phase was dried over anhydrous sodium sulfate and the solvent was removed under reduced pressure giving pure compound (4) as off-white solid foam.

Yield: 2.97 g (83%).

$^1$H NMR spectrum (300 MHz, CDCl$_3$, δ$_H$): 13.95 (bs, 1H); 13.79 (bs, 1H); 7.69 (bs, 1H); 4.17-4.10 (m, 2H); 4.03 (s, 2H); 3.74-3.56 (m, 12H); 3.52 (t, J=5.1 Hz, 2H); 3.03-2.83 (in, 6H); 2.32 (s, 8H); 2.13 (bs, 2H); 1.93 (sep, J=6.8 Hz, 2H); 1.43 (s, 9H); 1.03-0.90 (m, 24H).

2-Chlorotrityl resin 100-200 mesh 1.8 mmol/g (2.97 g, 5.35 mmol) was left to swell in dry DCM (100 mL) for 20 min. A solution of above compound (4) (2.92 g, 3.57 mmol) and DIPEA (2.36 mL, 13.6 mmol) in dry DCM (40 mL) was added to resin and the mixture was shaken overnight. Resin was filtered and treated with a solution of DIPEA (1.38 mL, 10.7 mmol) in MeOH/DCM mixture (4:1, 2×5 min, 70 mL). Then resin was washed with DMF (3×70 mL), 2-propanol (2×70 mL) and DCM (3×70 mL). The protecting groups were removed by treatment with hydrazine monohydrate (2% solution in DMF, 3×6 min, 3×70 mL). Then resin was washed with DMF (3×70 mL), 2-propanol (2×70 mL) and DCM (3×70 mL). Solution of chloroacetic acid (2.70 g, 28.6 mmol), 2,4,6-collidine (5.63 mL, 42.8 mmol) and DIC (4.42 mL, 28.6 mmol) in DMF (70 mL) was added to resin and mixture was shaken for 45 min. Resin was filtered and washed with DMF (4×70 mL), 2-propanol (2×70 mL) and DCM (8×70 mL). The product was cleaved from resin by treatment with cleavage cocktail (50% TFA in DCM, 80 mL) for 1 hour. Resin was filtered off and washed with DCM (3×40 mL). Solutions were combined and solvents were evaporated to dryness giving the desired compound (5) as thick brownish oil.

Yield: 1.84 g (90%).

$^1$H NMR spectrum (300 MHz, AcOD-d$_4$, δ$_H$): 4.32 (s, 2H); 4.20 (s, 2H); 4.18 (s, 2H); 4.16 (s, 2H); 3.84 (t, J=4.8 Hz, 2H); 3.81-3.72 (m, 4H); 3.68-3.51 (m, 8H); 3.38 (t, J=4.8 Hz, 2H).

Mixture of sodium bicarbonate (0.81 g, 9.63 mmol) and bromoacetic anhydride (1.67 g, 6.42 mmol) in MeCN (20 mL) was added to a solution of the above compound (5) (1.84 g, 3.21 mmol) in MeCN (20 mL). After 90 min the reaction mixture was filtered through sintered glass and the solvent was removed under reduced pressure. The residue was purified by HPLC (Column labio DeltaPak C18, 15 μm, 50×500 mm, MeCN/water 5:95 to 45:55+0.05% TFA). Resulting solution was freeze-dried to give 2-(2-(2-(2-(2-bromoacetamido)ethoxy)ethoxy)acetamido)-N,N-bis(2-(2-chloroacetamido)ethyl)acetamide (6) as colourless viscous oil.

Yield: 516 mg (33%).

$^1$H NMR spectrum (300 MHz, AcOD-d$_4$, δ$_H$): 4.29 (s, 2H); 4.19 (s, 2H); 4.16 (s, 2H); 4.14 (s, 2H); 3.98 (s, 2H); 3.75-3.49 (m, 16H).

LC-MS purity: 100%.

LC-MS Rt (Kinetex 4.6 mm×50 mm, MeCN/water 5:95 to 100:0+0.1% FA): 3.02 min.

LC-MS m/z: 480.2 (M+H)$^+$.

Trivalent Linker 4

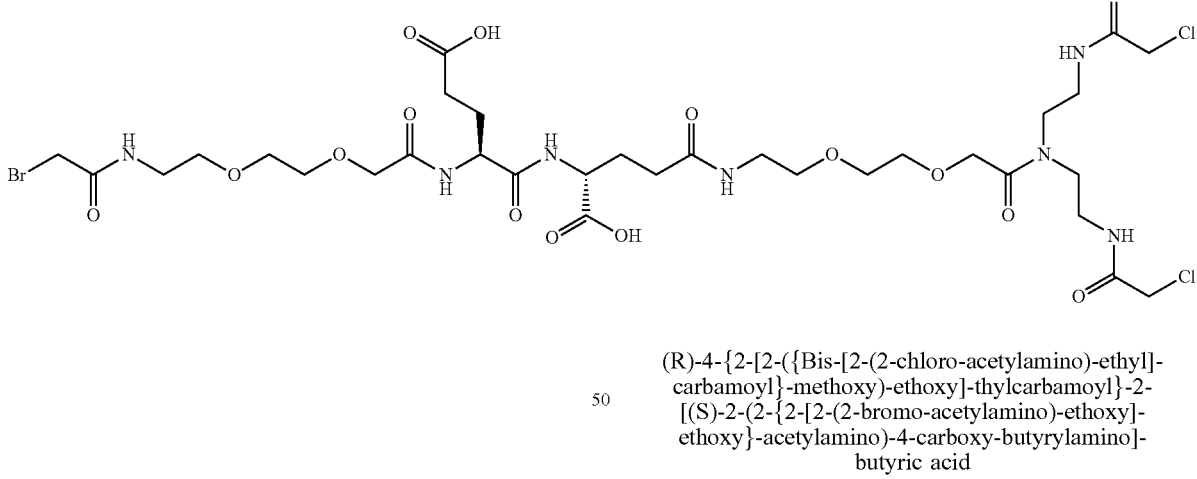

(R)-4-{2-[2-({Bis-[2-(2-chloro-acetylamino)-ethyl]-carbamoyl}-methoxy)-ethoxy]-thylcarbamoyl}-2-[(S)-2-(2-{2-[2-(2-bromo-acetylamino)-ethoxy]-ethoxy}-acetylamino)-4-carboxy-butyrylamino]-butyric acid Reaction scheme:

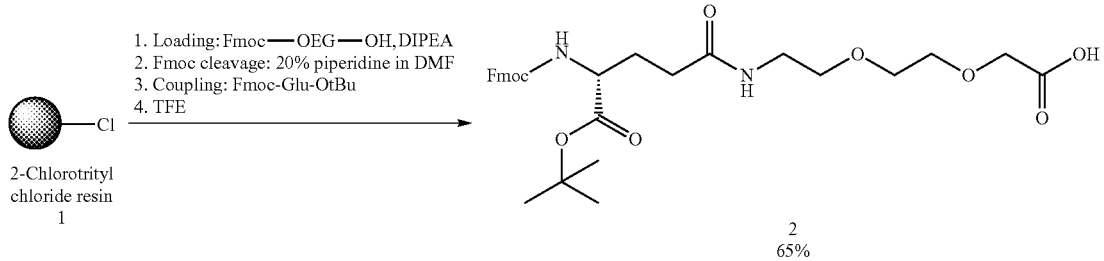

-continued
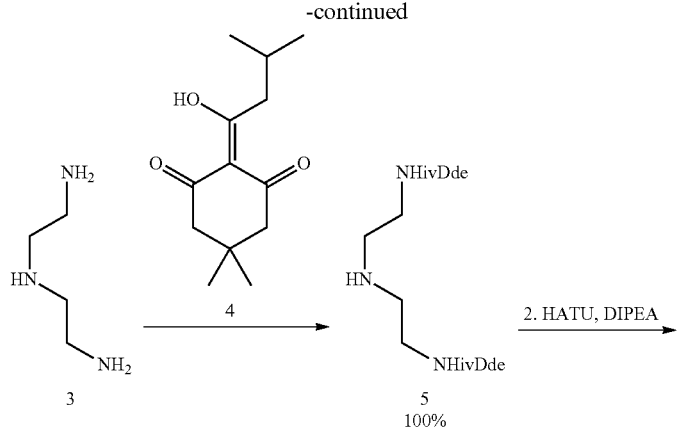
5
100%
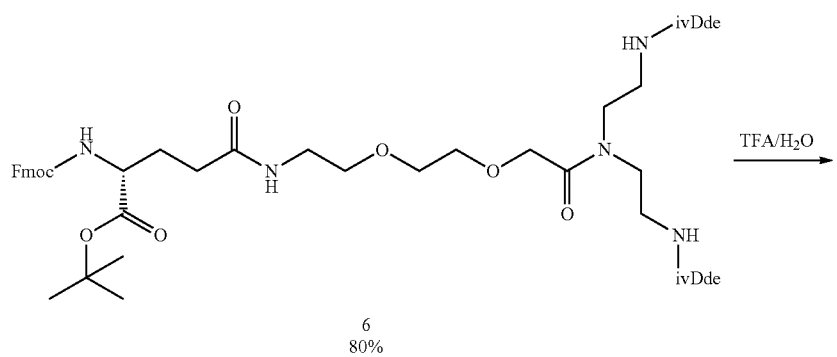
6
80%
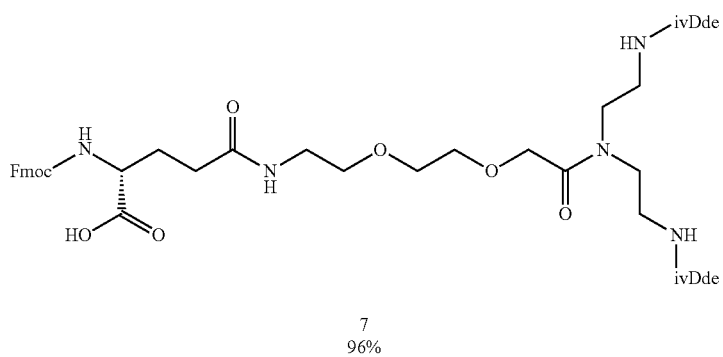
7
96%
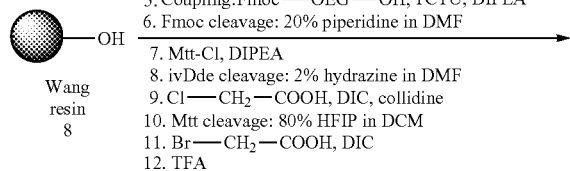
1. Loading: 7, DIC, DMAP
2. Fmoc cleavage: 20% piperidine in DMF
3. Coupling: Fmoc-Glu(OtBu)—OH, TCTU, DIPEA
4. Fmoc cleavage: 20% piperidine in DMF
5. Coupling: Fmoc—OEG—OH, TCTU, DIPEA
6. Fmoc cleavage: 20% piperidine in DMF
7. Mtt-Cl, DIPEA
8. ivDde cleavage: 2% hydrazine in DMF
9. Cl—CH$_2$—COOH, DIC, collidine
10. Mtt cleavage: 80% HFIP in DCM
11. Br—CH$_2$—COOH, DIC
12. TFA

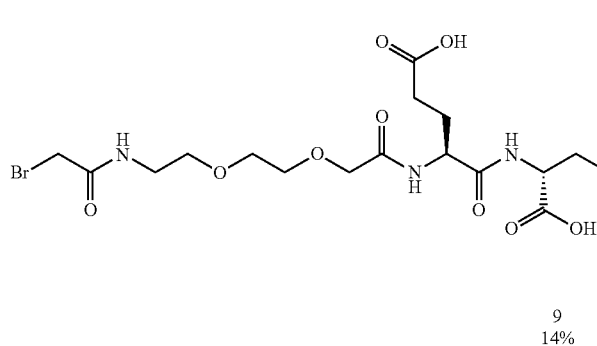

9
14%

Synthetic Protocol:

2-Chlorotrityl resin 100-200 mesh 1.8 mmol/g (1, 41.7 g, 75.1 mmol) was left to swell in dry DCM (350 mL) for 20 min. A solution of {2-[2-(9H-fluoren-9-ylmethoxycarbonylamino)-ethoxy]-ethoxy}-acetic acid (Fmoc-OEG-OH, 19.3 g, 50.1 mmol) and DIPEA (33.1 mL, 190 mmol) in dry DCM (250 mL) was added to resin and the mixture was shaken overnight. The resin was filtered and treated with a solution of DIPEA (17.4 mL, 100 mmol) in MeOH/DCM mixture (4:1, 5 min, 200 mL). Then resin was washed with DCM (2×250 mL) and DMF (2×250 mL). Fmoc group was removed by treatment with 20% piperidine in DMF (1×5 min, 1×15 min, 2×250 mL). The resin was washed with DMF (2×250 mL), 2-propanol (2×250 mL), DCM (2×250 mL) and DMF (2×250 mL). Solution of 2-(9H-fluoren-9-ylmethoxycarbonylamino)-pentanedioic acid 1-tert-butyl ester (Fmoc-Glu-OtBu, 42.6 g, 100 mmol), O-(6-chloro-benzotriazol-1-yl)-N,N,N',N'-tetramethyluronium tetrafluoroborate (TCTU, 35.6 g, 100 mmol) and DIPEA (31.4 mL, 180 mmol) in DMF (200 mL) was added to resin and mixture was shaken for 4 hours. Resin was filtered and washed with DMF (2×250 mL) and DCM (10×250 mL). The product was cleaved from resin by treatment with 2,2,2-trifluoroethanol (350 mL) overnight. Resin was filtered off and washed with DCM (2×200 mL), solvent was evaporated and crude product was purified by flash column chromatography (Silicagel 60, 0.040-063 mm; eluent: DCM/MeOH 95:5 to 85:15) giving (R)-4-[2-(2-carboxymethoxy-ethoxy)-ethylcarbamoyl]-2-(9H-fluoren-9-ylmethoxycarbonylamino)-butyric acid tert-butyl ester (2) as yellowish waxy solid.

Yield: 18.6 g (65%).

$^1$H NMR spectrum (300 MHz, CDCl$_3$, $\delta_H$): 7.77 (d, J=7.5 Hz, 2H); 7.65-7.50 (m, 2H); 7.47-7.37 (m, 2H); 7.37-6.72 (m, 2H); 6.84-6.72 (m, 1H); 5.92-5.81 (m, 1H); 4.58-4.30 (m, 2H); 4.30-3.95 (m, 4H); 3.79-3.51 (m, 6H); 3.43 (q, J=4.6 Hz, 2H); 2.39-1.90 (m, 4H); 1.54-1.39 (m, 9H).

LC-MS purity: 100%.

LC-MS Rt (Kinetex C18, 4.6 mm×50 mm, MeCN/water 20:80 to 100:0+0.1% FA): 3.65 min.

LC-MS m/z: 570.6 (M+H)$^+$.

Diethylenetriamine (3) (1.62 mL, 15.0 mmol) was added to a solution of 2-(1-hydroxy-3-methyl-butylidene)-5,5-dimethyl-cyclohexane-1,3-dione (4) (6.73 g, 30.0 mmol) in DCM (125 mL). The resulting solution was stirred overnight, then the solvent was evaporated and residue was dried in vacuo affording 2,2'-(((azanediylbis(ethane-2,1-diyl))bis (azanediyl))bis(3-methylbutan-1-yl-1-ylidene))bis(5,5-dimethylcyclohexane-1,3-dione) (5) as yellow oil.

Yield: 7.74 g (100%).

$^1$H NMR spectrum (300 MHz, CDCl$_3$, $\delta_H$): 13.81 (bs, 2H); 3.64-3.44 (m, 4H); 3.12-2.83 (m, 8H); 2.34 (s, 8H); 2.06-1.86 (m, 2H); 1.05-0.87 (m, 24H).

The compound (2) (18.5 g, 32.5 mmol) was dissolved in DCM (220 mL) followed by addition of HATU (12.4 g, 32.5 mmol), DIPEA (8.30 mL, 47.6 mmol) and solution of the amine (5) (7.04 g, 13.6 mmol) in DCM (150 mL). The resulting solution was stirred overnight and then the solvent was evaporated. The residue was dissolved in ethyl acetate (250 mL) and washed with water (4×250 mL). Organic layer was dried over anhydrous sodium sulphate, filtered and evaporated. The residue was purified by flash column chromatography (Silicagel 60, 0.040-063 mm; eluent: DCM/MeOH 97:3 to 96:4) giving (R)-4-(2-{2-[(bis-{2-[1-(4,4-dimethyl-2,6-dioxo-cyclohexylidene)-3-methyl-butylamino]-ethyl}-carbamoyl)-methoxy]-ethoxy}-ethylcarbamoyl)-2-(9H-fluoren-9-ylmethoxycarbonylamino)-butyric acid tert-butyl ester (6) as white solid.

Yield: 11.6 g (80%).

$^1$H NMR spectrum (300 MHz, CDCl$_3$, $\delta_H$): 14.02-13.78 (m, 2H); 7.77 (d, J=7.2 Hz, 2H); 7.60 (d, J=6.8 Hz, 2H); 7.40 (t, J=7.1 Hz, 2H); 7.35-7.24 (m, 2H); 6.76 (bs, 1H); 5.85 (d, J=8.5 Hz, 1H); 4.50-4.13 (m, 6H); 3.79-3.35 (m, 16H); 3.06-2.85 (m, 4H); 2.45-2.12 (m, 11H); 2.09-1.82 (m, 3H); 1.47 (s, 9H); 1.07-0.85 (m, 24H).

LC-MS purity: 100%.

LC-MS Rt (Kinetex C18, 4.6 mm×50 mm, MeCN/water 70:30 to 100:0+0.1% FA): 2.12 min.

LC-MS m/z: 1068.3 (M+H)$^+$.

The above prepared compound (6) (11.6 g, 10.9 mmol) was dissolved in mixture of TFA/H$_2$O (95:5, 150 mL) and left to stay for 2.5 hrs. Then solvent was evaporated. The residue was dissolved in DCM (30 mL) and diethyl ether (200 mL) was added. The mixture was stirred overnight; then diethyl ether was decanted. The residue was treated with diethyl ether (200 mL) and then decanted again. The procedure was repeated once more. The residue was dried in vacuo to yield (R)-4-(2-{2-[(bis-{2-[1-(4,4-dimethyl-2,6-dioxo-cyclohexylidene)-3-methyl-butylamino]-ethyl}-carbamoyl)-methoxy]-ethoxy}-ethylcarbamoyl)-2-(9H-fluoren-9-ylmethoxycarbonylamino)-butyric acid (7) as pale yellow solid.

Yield: 10.7 g (96%).

$^1$H NMR spectrum (300 MHz, CDCl$_3$, $\delta_H$): 13.90-13.65 (m, 2H); 7.77 (d, J=7.5 Hz, 2H); 7.67-7.53 (m, 2H); 7.40 (t, J=7.2 Hz, 2H); 7.35-7.23 (m, 3H); 6.01 (d, J=7.5 Hz, 1H); 4.49-4.34 (m, 3H); 4.31-4.15 (m, 3H); 3.86-3.30 (m, 16H); 3.14-2.84 (m, 4H); 2.55-2.31 (m, 10H); 2.30-2.05 (m, 2H); 2.03-1.78 (m, 2H); 1.11-0.88 (m, 24H).

LC-MS purity: 100%.

LC-MS Rt (Kinetex C18, 4.6 mm×50 mm, MeCN/water 35:65 to 100:0+0.1% FA): 3.68 min.

LC-MS m/z: 1012.2 (M+H)$^+$.

Wang resin 0.68 mmol/g (1) (4.97 g, 3.38 mmol) was swollen in THF (110 mL) for 60 min. A solution of compound (7) (10.3 g, 10.1 mmol), DIC (1.57 mL, 10.1 mmol) and 4-dimethylamino-pyridine (0.04 g, 0.34 mmol) in THF (80 mL) was added to resin and the mixture was shaken overnight. Resin was filtered, washed with DCM (2×100 mL) and treated with a solution of acetic anhydride (5.00 mL, 50.1 mmol) and pyridine (5.00 mL, 61.6 mmol) in DCM (70 mL) for 10 minutes. Resin was washed with DCM (6×100 mL). Fmoc group was removed by treatment with 20% piperidine in DMF (1×5 min, 1×15 min, 2×80 mL). Resin was washed with DMF (2×100 mL), 2-propanol (2×100 mL), DCM (2×100 mL) and DMF (2×100 mL). A solution of (S)-2-((((9H-fluoren-9-yl)methoxy)carbonyl)amino)-5-(tert-butoxy)-5-oxopentanoic acid (Fmoc-Glu(OtBu)-OH, 4.31 g, 10.1 mmol), 5-chloro-1-((dimethylamino)(dimethyliminio)methyl)-1H-benzo[d][1,2,3]triazole 3-oxide tetrafluoroborate (TCTU, 3.60 g, 10.1 mmol) and DIPEA (3.18 mL, 18.2 mmol) in DMF (70 mL) was added to resin and the mixture was shaken for 3 hours. Resin was filtered and washed with DMF (2×100 mL), DCM (2×100 mL) and DMF (2×100 mL). Fmoc group was removed by treatment with 20% piperidine in DMF (1×5 min, 1×15 min, 2×80 mL). Resin was washed with DMF (2×100 mL), 2-propanol (2×100 mL), DCM (2×100 mL) and DMF (2×100 mL). A solution of {2-[2-(9H-fluoren-9-ylmethoxycarbonylamino)-ethoxy]-ethoxy}-acetic acid (Fmoc-OEG-OH, 3.90 g, 10.1 mmol), 5-chloro-1-((dimethylamino)(dimethyliminio)methyl)-1H-benzo[d][1,2,3]triazole 3-oxide tetrafluoroborate (TCTU, 3.60 g, 10.1 mmol) and DIPEA (3.18 mL, 18.2 mmol) in DMF (70 mL) was added to resin and the mixture was shaken overnight. Resin was filtered and washed with DMF (2×100 mL), DCM (2×100 mL) and DMF (2×100 mL). Fmoc group was removed by treatment with 20% piperidine in DMF (1×5 min, 1×15 min, 2×80 mL). Resin was washed with DMF (2×100 mL), 2-propanol (2×100 mL), DCM (2×100 mL) and DMF (2×100 mL). A solution of 1-(chloro-diphenyl-methyl)-4-methyl-benzene (MttCl, 2.97 g, 10.1 mmol) and DIPEA (3.53 mL, 20.3 mmol) in dry DCM (70 mL) was added to resin and mixture was shaken for 4.5 hrs. Resin was filtered and washed with DMF (2×100 mL), DCM (3×100 mL) and DMF (3×100 mL). The IvDde group was removed by treatment with 2% hydrazine monohydrate in DMF (3×3 min, 3×80 mL). Resin was washed with DMF (6×100 mL). A solution of chloroacetic acid (1.91 g, 20.3 mmol), DIC (3.14 mL, 20.3 mmol) and 2,4,6-trimethylpyridine (5.35 mL, 40.5 mmol) in DMF (80 mL) was added to resin and mixture was shaken for 2.5 hrs. Resin was filtered and washed with DMF (3×100 mL) and DCM (3×100 mL). The Mtt group was removed by treatment with 80% 1,1,1,3,3,3-hexafluoro-2-propanol in DCM (2×10 min, 3×30 min, 5×75 mL). Resin was washed with DCM (3×100 mL) and DMF (3×100 mL). A solution of bromoacetic acid (9.39 g, 67.6 mmol) and DIC (8.90 mL, 57.5 mmol) in DMF (80 mL) was added to resin and mixture was shaken for 20 min. Resin was filtered and washed with DMF (3×100 mL) and DCM (10×100 mL). The product was cleaved from resin by treatment with mixture of TFA and water (98:2, 100 mL) for 1 hr. Resin was filtered and washed with DCM (2×80 mL). Solutions were combined and solvents were evaporated to dryness. The residue was purified by HPLC (Column DeltaPak C18, 15 um; 50×500 mm; MeCN/water 5:95 to 60:40+0.05% TFA) and freeze-dried to give the title compound (9) as a white solid.

Yield: 425 mg (14%).

$^1$H NMR spectrum (300 MHz, AcOD-d$_4$, $\delta_H$): 4.76 (dd, J=7.8 and 5.9 Hz, 1H); 4.57 (dd, J=8.9 and 4.9 Hz, 1H); 4.36 (s, 2H); 4.20 (s, 2H); 4.14 (s, 4H); 3.98 (s, 2H); 3.81-3.41 (m, 24H); 2.56 (t, J=8.0 Hz, 2H); 2.47 (t, J=7.2 Hz, 2H); 2.37-2.20 (m, 2H); 2.20-2.05 (m, 2H).

LC-MS purity: 100%.

LC-MS Rt (Kinetex C18, 4.6 mm×50 mm, MeCN/water 5:95 to 100:0+0.1% FA): 3.58 min.

LC-MS m/z: 925.6 (M+H)$^+$.

Trivalent Linker 5

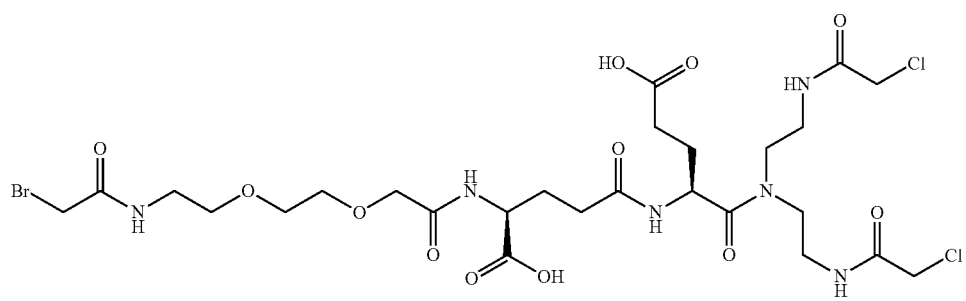 [SMILES: O=C(O)CC[C@H](NC(=O)CC[C@H](NC(=O)COCCOCCNC(=O)CBr)C(=O)O)C(=O)N(CCNC(=O)CCl)CCNC(=O)CCl]

(13R,18S)-18-(bis(2-(2-Chloroacetamido)ethyl)carbamoyl)-1-bromo-13-carboxy-2,11,16-trioxo-6,9-dioxa-3,12,17-triazahenicosan-21-oic acid Reaction scheme:

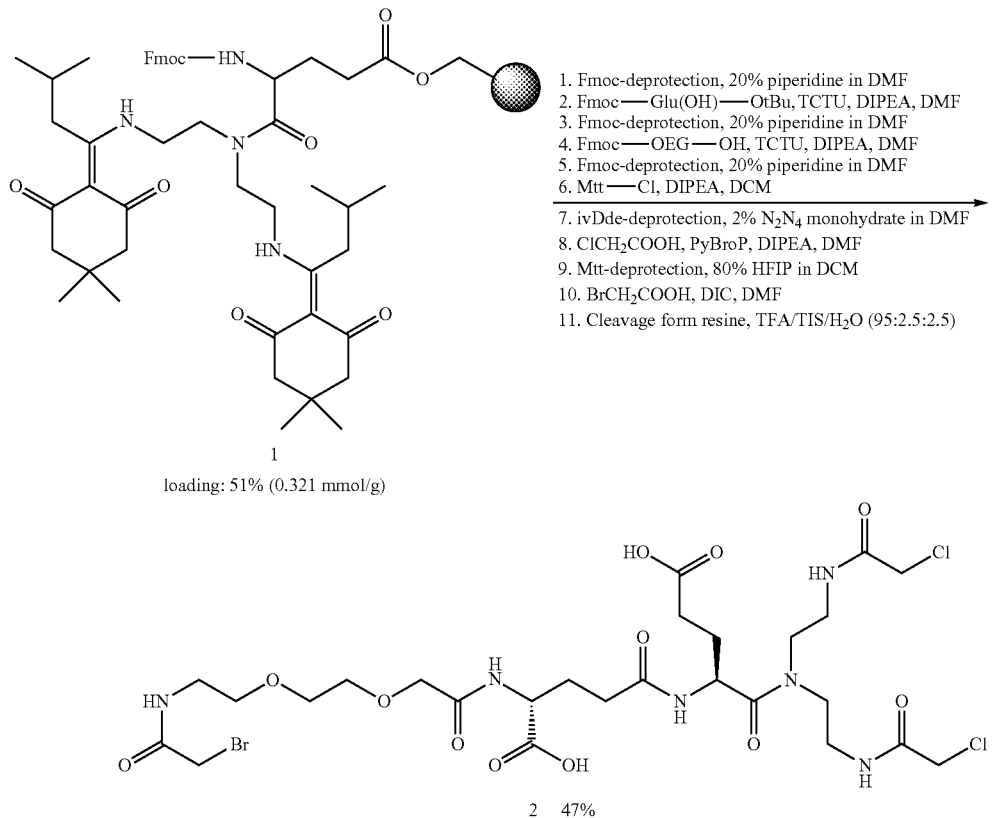

1. Fmoc-deprotection, 20% piperidine in DMF
2. Fmoc—Glu(OH)—OtBu, TCTU, DIPEA, DMF
3. Fmoc-deprotection, 20% piperidine in DMF
4. Fmoc—OEG—OH, TCTU, DIPEA, DMF
5. Fmoc-deprotection, 20% piperidine in DMF
6. Mtt—Cl, DIPEA, DCM
7. ivDde-deprotection, 2% $N_2H_4$ monohydrate in DMF
8. ClCH$_2$COOH, PyBroP, DIPEA, DMF
9. Mtt-deprotection, 80% HFIP in DCM
10. BrCH$_2$COOH, DIC, DMF
11. Cleavage form resine, TFA/TIS/H$_2$O (95:2.5:2.5)

1
loading: 51% (0.321 mmol/g)

2  47%

Synthetic Protocol:

Preparation of Wang resin-bound 1 was described in protocol REaD-24247 (Batch No. 218-004-1).

Wang resin-bound (1, 2.85 g, 0.92 mmol) was left to swell in DCM (20 mL) for 20 min. Fmoc group was removed by treatment with 20% piperidine in DMF (1×5 min, 1×30 min, 2×20 mL). Resin was washed with DMF (3×20 mL), 2-propanol (3×20 mL) and DCM (3×20 mL). Solution of (S)-2-(9H-fluoren-9-ylmethoxycarbonylamino)-pentanedioic acid 1-tert-butyl ester (Fmoc-LGlu-OtBu, 1.17 g, 2.75 mmol), TCTU (0.98 g, 2.75 mmol) and DIPEA (0.96 mL, 5.49 mmol) in DMF (20 mL) was added to resin and mixture was shaken for 2 hrs. Fmoc group was removed by treatment with 20% piperidine in DMF (1×5 min, 1×30 min, 2×20 mL). Resin was washed with DMF (3×20 mL), 2-propanol (3×20 mL) and DCM (3×20 mL). A solution of {2-[2-(9H-fluoren-9-ylmethoxycarbonylamino)-ethoxy]-ethoxy}-acetic acid (Fmoc-OEG-OH, 1.06 g, 2.75 mmol), TCTU (0.98 g, 2.75 mmol) and DIPEA (0.96 mL, 5.49 mmol) in DMF (20 mL) was added to resin and the mixture was shaken for 3.5 hrs. Resin was filtered and washed with DMF (3×20 mL), DCM (3×20 mL) and DMF (3×20 mL). Fmoc group was removed by treatment with 20% piperidine in DMF (1×5 min, 1×30 min, 2×20 mL). Resin was washed with DMF (3×20 mL), 2-propanol (3×20 mL) and DCM (3×20 mL).

A solution of 1-(chloro-diphenyl-methyl)-4-methyl-benzene (MttCl, 1.20 g, 4.10 mmol) and DIPEA (1.44 mL, 8.27 mmol) in dry DCM (40 mL) was added to resin and mixture was shaken for 1 hour. Resin was filtered and washed with DCM (4×20 mL) and DMF (4×20 mL). IvDde group was removed by treatment with 2% hydrazine monohydrate in DMF (3×3 min, 3×20 mL). Resin was washed with DMF (8×20 mL). A solution of chloroacetic acid (0.52 g, 5.49 mmol), PyBroP (2.56 g, 5.49 mmol) and DIPEA (1.91 mL, 11.0 mmol) in DMF (25 mL) was added to resin and mixture was shaken for 3 hrs. Resin was filtered and washed with DMF (4×20 mL), DCM (4×20 mL), DMF (4×20 mL), DCM (10×20 mL). Mtt group was removed by treatment with 80% 1,1,1,3,3,3-hexafluoro-2-propanol in DCM (2×10 min, 2×30 min, 4×25 mL). Resin was washed with DCM (5×20 mL) and DMF (4×20 mL). A solution of bromoacetic acid (2.54 g, 18.3 mmol) and DIC (2.41 mL, 15.6 mmol) in DMF (30 mL) was added to resin and mixture was shaken for 25 minutes. Resin was filtered and washed with DMF (4×20 mL), MeCN (2×20 mL) and DCM (10×20 mL). The product was cleaved from resin by treatment with cleavage cocktail of TFA/TIS/H$_2$O (95:2.5:2.5, 30 mL) for 1 hour. Resin was filtered and washed with DCM (10×30 mL). Solutions were combined and solvents were evaporated to dryness. The solvent was co-evaporated with toluene for three times. The residue was purified by HPLC (Column X-Bridge3 C18, OBD, 5 µm, 50×250 mm, MeCN/water 5% to 35%+0.05% TFA) to give (13R,18S)-18-(bis(2-(2-chloroacetamido)ethyl)carbamoyl)-1-bromo-13-carboxy-2,11,16-trioxo-6,9-dioxa-3,12,17-triazahenicosan-21-oic acid (2) as white solid.

Yield: 333 mg (47%).

1H NMR spectrum (300 MHz, AcOD-$d_4$, 80° C., $\delta_H$): 5.08 (dd, J=9.5 Hz, J=4.2 Hz, 1H); 4.71 (dd, J=8.1 Hz, J=5.1 Hz, 1H); 4.19-4.09 (m, 6H); 3.96 (s, 2H); 3.90-3.44 (m, 16H); 2.59-2.07 (m, 7H); 2.01-1.86 (m, 1H).

LC-MS purity: 100%.

LC-MS Rt (Kinetex 4.6 mm×50 mm, MeCN/$H_2O$ 5:95 to 100:0+0.1% FA): 4.56 min.

LC-MS m/z: 781.5 $(M+H)^+$.

UPLC purity: 99% (220 nm).

UPLC Rt (Acquity UPLC BEHC 18, 1.7 μm, 2.1×150 mm; MeCN/$H_2O$ 5:95 to 100:0+0.1% TFA): 1.57 min.

Trivalent Linker 6

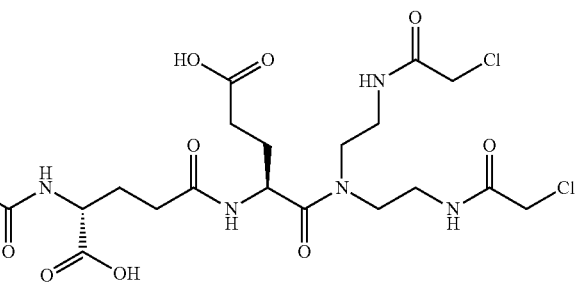

(18R,23S)-23-(Bis(2-(2-chloroacetamido)ethyl)carbamoyl)-1-bromo-18-carboxy-2,7,16,21-tetraoxo-11,14-dioxa-3,8,17,22-tetraazahexacosan-26-oic acid Reaction Scheme:

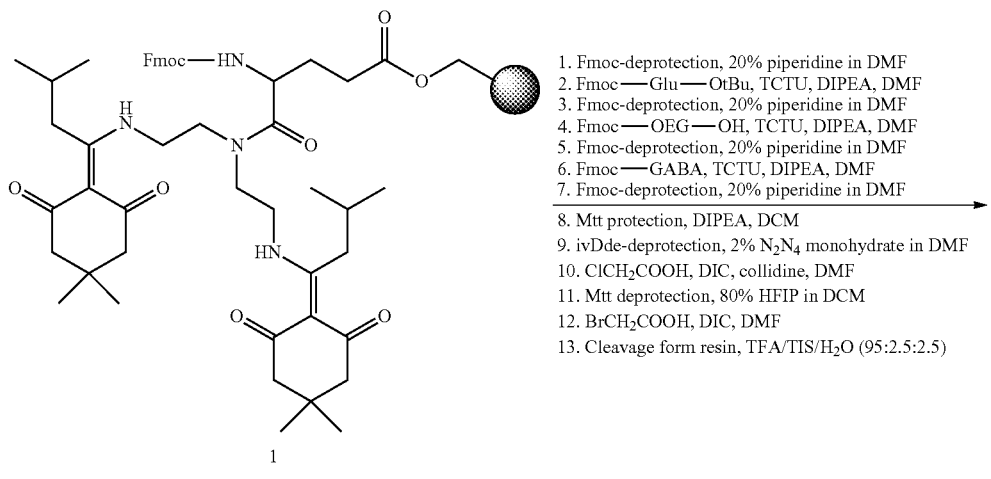

1
loading: 51% (0.321 mmol/g)

1. Fmoc-deprotection, 20% piperidine in DMF
2. Fmoc—Glu—OtBu, TCTU, DIPEA, DMF
3. Fmoc-deprotection, 20% piperidine in DMF
4. Fmoc—OEG—OH, TCTU, DIPEA, DMF
5. Fmoc-deprotection, 20% piperidine in DMF
6. Fmoc—GABA, TCTU, DIPEA, DMF
7. Fmoc-deprotection, 20% piperidine in DMF
8. Mtt protection, DIPEA, DCM
9. ivDde-deprotection, 2% $N_2N_4$ monohydrate in DMF
10. ClCH$_2$COOH, DIC, collidine, DMF
11. Mtt deprotection, 80% HFIP in DCM
12. BrCH$_2$COOH, DIC, DMF
13. Cleavage form resin, TFA/TIS/$H_2O$ (95:2.5:2.5)

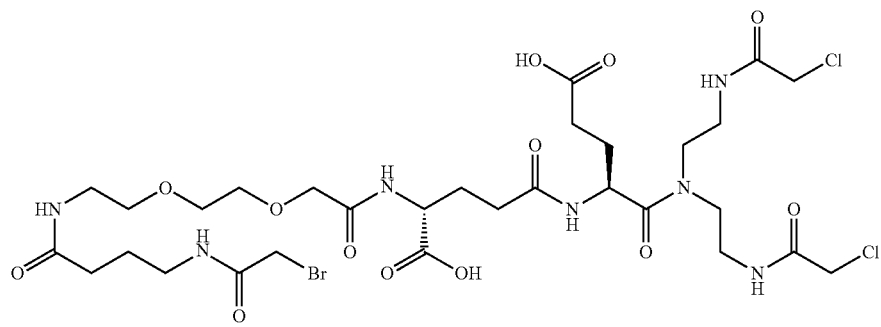

2    43%

Synthetic Protocol:
Preparation of Compound (1).

The solution of 2-(1-hydroxy-3-methylbutylidene)-5,5-dimethylcyclohexane-1,3-dione (37.7 g, 168 mmol) in DCM (200 mL) was added dropwise to a solution of diethylenetriamine (8.64 mL, 80.0 mmol) in DCM (130 mL). The reaction mixture was stirred overnight, then solvent was evaporated affording 2,2'-(((azanediylbis(ethane-2,1-diyl))bis(azanediyl))bis(3-methylbutan-1-yl-1-ylidene))bis(5,5-dimethylcyclohexane-1,3-dione) as pale yellow oil.

Yield: 41.2 g (100%).

1H NMR spectrum (300 MHz, CDCl$_3$, $\delta_H$): 3.57 (q, 4H); 3.06-2.89 (m, 8H); 2.36 (bs, 8H); 2.05-1.89 (m, 2H); 1.09-0.94 (m, 26H).

The solution of the above amine (33.4 g, 64.8 mmol) in DMF (320 mL) was added to a solution of 2-(9H-fluoren-9-ylmethoxycarbonylamino)-pentanedioic acid 5-tert-butyl ester (Fmoc-Glu(OtBu)-OH, 63.4 g, 149 mmol), HATU (56.6 g, 149 mmol), DIPEA (40.0 mL, 227 mmol) in DMF (530 mL). The reaction mixture was stirred at room temperature overnight. Then ethyl acetate (1.6 L) and water (1.6 L) were added. Separated organic layer was washed with aqueous solution of 10% K$_2$CO$_3$ (2×1.6 L), dried over anhydrous Na$_2$SO$_4$, filtered and evaporated in vacuo. The residue was purified by flash column chromatography (Silicagel 60, 0.063-0.040 mm; eluent: DCM/MeOH 50:1-40:1) to give tert-butyl 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoate as pale yellow viscous oil.

Yield: 59.2 g (99%).

1H NMR spectrum (300 MHz, CDCl$_3$, $\delta_H$): 7.77 (d, J=7.5 Hz, 2H); 7.59 (m, 2H); 7.40 (t, J=7.5 Hz, 2 Hz); 7.36-7.26 (m, 2H); 5.65 (d, J=9.2 Hz, 1H); 4.72-4.59 (m, 1 H); 4.46-4.27 (m, 2H); 4.24-4.16 (m, 1H); 4.12-3.99 (m, 1H); 3.94-3.53 (m, 6H); 3.48-3.33 (m, 1H); 2.97 (bs, 4H); 2.46-2.26 (m, 10H); 2.08-1.83 (m, 4H); 1.79-1.64 (m, 1H); 1.43 (s, 9H); 1.07-0.90 (m, 24H).

tert-Butyl 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoate (59.2 g, 64.8 mmol) dissolved in DCM (50 mL) was added to TFA/H$_2$O mixture (95:5, 400 mL) and stirred for 2 hrs. Then solvent was evaporated and the residue was co-evaporated with toluene for three times. The residue was dissolved in DCM (800 mL) and washed with water (3×800 mL). The solvent was evaporated under reduced pressure. The residue was purified by column chromatography (Silicagel 60, 0.063-0.040 mm; eluent: DCM/methanol 60:1-10:1) affording 4-((((9H-fluoren-9-yl)methoxy)-carbonyl)amino)-5-(bis(2-((1-(4,4-dimethyl-2,6-dioxocyclohexylidene)-3-methylbutyl)-amino)ethyl)amino)-5-oxopentanoic acid as white powder.

Yield: 42.1 g (76%).

1H NMR spectrum (300 MHz, AcOD-d$_4$, 80° C., $\delta_H$): 7.79 (d, J=7.3 Hz, 2H); 7.64 (d, J=7.5 Hz, 2H); 7.39 (t, J=7.4 Hz, 2H); 7.36-7.26 (m, 2H); 4.83 (bs, 1H); 4.48-4.30 (m, 2H); 4.27-4.19 (m, 1H); 4.19-3.62 (m, 7H); 3.61-3.46 (m, 1H); 3.28-2.90 (m, 4H); 2.55 (t, J=6.7 Hz, 2H); 2.43 (s, 8H); 2.01-1.81 (m, 4H); 1.07-0.88 (m, 24H).

Wang resin 0.63 mmol/g (25.7 g, 16.2 mmol) was left to swell in tetrahydrofuran (250 mL) for 20 minutes. A solution of the 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoic acid (42.0 g, 48.5 mmol) in THF (250 mL) was added to resin and then DIC (7.60 mL, 48.5 mmol) and 4-dimethylaminopyridine (DMAP, 200 mg, 1.62 mmol). The mixture was shaken for 18 hrs. The resin was filtered off and washed with DCM (6×250 mL). Resin was treated with a solution of acetic anhydride (40 mL), pyridine (40 mL) in DMF (360 mL) for 15 min. and washed with DCM (6×250 mL) affording compound (1) as yellow solid.

Yield: 36.0 g.

Loading: 51% (0.321 mmol/g).

Wang resin-bound compound (1) (2.85 g, 0.92 mmol) was swollen in DCM (20 mL) for 20 min. The Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL). Solution of (S)-2-(9H-fluoren-9-ylmethoxycarbonylamino)-pentanedioic acid 1-tert-butyl ester (Fmoc-LGlu-OtBu, 1.17 g, 2.75 mmol), TCTU (0.98 g, 2.75 mmol) and DIPEA (0.96 mL, 5.49 mmol) in DMF (60 mL) was added to resin and mixture was shaken for 3 hrs. Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL). A solution of {2-[2-(9H-fluoren-9-ylmethoxy-carbonylamino)-ethoxy]-ethoxy}-acetic acid (Fmoc-OEG-OH, 1.06 g, 2.75 mmol), TCTU (0.98 g, 2.75 mmol) and DIPEA (0.96 mL, 5.49 mmol) in DMF (50 mL) was added to resin and the mixture was shaken for 2 hrs. Resin was filtered and washed with DMF (3×70 mL), DCM (3×70 mL) and DMF (3×70 mL). Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL).

A solution of 4-((((9H-fluoren-9-yl)methoxy)carbonyl)amino)butanoic acid (Fmoc-GABA, 0.88 g, 2.70 mmol), TCTU (0.96 g, 2.70 mmol) and DIPEA (0.94 mL, 5.40 mmol) in DMF (50 mL) was added to resin and the mixture was shaken for 2 hrs. Resin was filtered and washed with DMF (3×70 mL), DCM (3×70 mL) and DMF (3×70 mL). Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL). A solution of 1-(chloro-diphenyl-methyl)-4-methyl-benzene (MttCl, 0.79 g, 2.70 mmol) and DIPEA (0.94 mL, 5.4 mmol) in dry DCM (60 mL) was added to resin and mixture was shaken for 3 hrs. The resin was filtered off and washed with DCM (3×70 mL) and DMF (3×70 mL). The IvDde group was removed by treatment with 2% hydrazine monohydrate in DMF (3×3 min, 3×30 mL). The resin was washed with DMF (5×40 mL). A solution of chloroacetic acid (0.51 g, 5.40 mmol), DIC (0.85 mL, 5.40 mmol) and 2,4,6-trimethylpyridine (1.43 mL, 10.8 mmol) in DMF (50 mL) was added to the resin and the mixture was shaken for 2.5 hrs. The resin was filtered off and washed with DMF (3×70 mL) and DCM (3×70 mL). The Mtt group was removed by treatment with 80% 1,1,1,3,3,3-hexafluoro-2-propanol in DCM (2×10 min, 2×30 min, 4×50 mL). The resin was washed with DCM (5×50 mL) and DMF (4×50 mL). A solution of bromoacetic acid (0.38 g, 2.70 mmol) and DIC (0.42 mL, 2.70 mmol) in DMF (50 mL) was added to resin and mixture was shaken for 2.5 hrs. Resin was filtered and washed with DMF (3×70 mL) and DCM (3×70 mL). The product was cleaved from resin by treatment with cleavage cocktail of TFA/TIS/H$_2$O (95:2.5:2.5, 26 mL) for 1 hr. The resin was filtered off and washed with DCM (6×40 mL). Solutions were combined and solvents were evaporated to dryness. The residue was purified by HPLC (Column Gemini C18, 5 µm; 50×250 mm; MeCN/

H₂O 5:95 to 40:60 during 180 min. and 5:95 to 35:65 during 60 min.+0.05% TFA) and freeze-dried to give title compound (2) as white solid.

Yield: 336 mg (43%).

¹H NMR spectrum (300 MHz, AcOD-d₄, $\delta_H$): 5.07 (dd, J=9.9 and 2.9 Hz, 1H); 4.72 (dd, J=8.7 and 4.7 Hz, 1H); 4.22-4.12 (m, 6H); 3.96 (s, 2H); 3.93-3.37 (m, 16H); 3.33 (t, J=6.8 Hz, 3H); 2.59-2.29 (m, 7H); 2.10 (d, J=4.9 Hz, 2H); 1.97-1.80 (m, 3H).

LC-MS purity: 100%.
LC-MS Rt (Kinetex 4.6 mm×50 mm, MeCN/H₂O 5:95 to 100:0+0.1% FA): 2.86 min.
LC-MS m/z: 866.5 (M+H)⁺.
UPLC purity: 98.7% (214 nm).
UPLC Rt (Acquity UPLC BEHC 18, 1.7 μm, 2.1×150 mm; MeCN/H₂O 5:95 to 100:0+0.05% TFA): 2.74 min.

Trivalent Linker 6

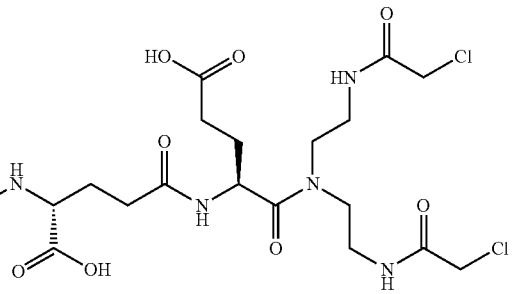

(18R,23S)-23-(Bis(2-(2-chloroacetamido)ethyl)carbamoyl)-1-bromo-18-carboxy-2,7,16,21-tetraoxo-11,14-dioxa-3,8,17,22-tetraazahexacosan-26-oic acid Reaction scheme:

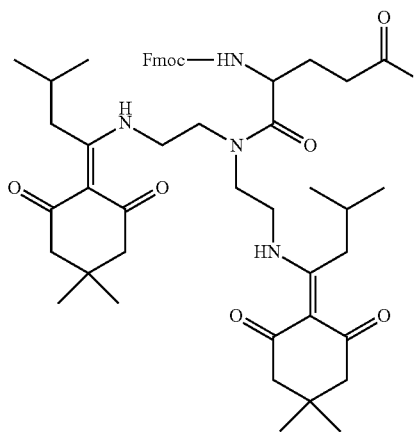

1. Fmoc-deprotection, 20% piperidine in DMF
2. Fmoc-Glu-OtBu, TCTU, DIPEA, DMF
3. Fmoc-deprotection, 20% piperidine in DMF
4. Fmoc—OEG—OH, TCTU, DIPEA, DMF
5. Fmoc-deprotection, 20% piperidine in DMF
6. Fmoc—GABA, TCTU, DIPEA, DMF
7. Fmoc-deprotection, 20% piperidine in DMF
8. Mtt protection, DIPEA, DCM
9. ivDde-deprotection, 2% N₂H₄ monohydrate in DMF
10. ClCH₂COOH, DIC, collidine, DMF
11. Mtt deprotection, 80% HFIP in DCM
12. BrCH₂COOH, DIC, DMF
13. Cleavage from resine, TFA/TIS/H₂O (95:2.5:2.5)

1
loading: 51% (0.321 mmol/g)

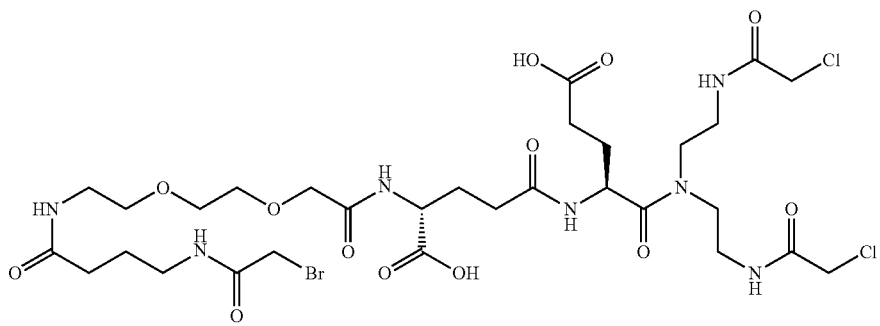

2
43%

Synthetic Protocol:
Preparation of Compound (1).

The solution of 2-(1-hydroxy-3-methylbutylidene)-5,5-dimethylcyclohexane-1,3-dione (37.7 g, 168 mmol) in DCM (200 mL) was added dropwise to a solution of diethylenetriamine (8.64 mL, 80.0 mmol) in DCM (130 mL). The reaction mixture was stirred overnight, then solvent was evaporated affording 2,2'-(((azanediylbis(ethane-2,1-diyl))bis(azanediyl))bis(3-methylbutan-1-yl-1-ylidene))bis(5,5-dimethylcyclohexane-1,3-dione) as pale yellow oil.

Yield: 41.2 g (100%).

1H NMR spectrum (300 MHz, CDCl$_3$, $\delta_H$): 3.57 (q, 4H); 3.06-2.89 (m, 8H); 2.36 (bs, 8H); 2.05-1.89 (m, 2H); 1.09-0.94 (m, 26H).

The solution of the above amine (33.4 g, 64.8 mmol) in DMF (320 mL) was added to a solution of 2-(9H-fluoren-9-ylmethoxycarbonylamino)-pentanedioic acid 5-tert-butyl ester (Fmoc-Glu(OtBu)-OH, 63.4 g, 149 mmol), HATU (56.6 g, 149 mmol), DIPEA (40.0 mL, 227 mmol) in DMF (530 mL). The reaction mixture was stirred at room temperature overnight. Then ethyl acetate (1.6 L) and water (1.6 L) were added. Separated organic layer was washed with aqueous solution of 10% K$_2$CO$_3$ (2×1.6 L), dried over anhydrous Na$_2$SO$_4$, filtered and evaporated in vacuo. The residue was purified by flash column chromatography (Silicagel 60, 0.063-0.040 mm; eluent: DCM/MeOH 50:1-40:1) to give tert-butyl 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoate as pale yellow viscous oil.

Yield: 59.2 g (99%).

1H NMR spectrum (300 MHz, CDCl$_3$, $\delta_H$): 7.77 (d, J=7.5 Hz, 2H); 7.59 (m, 2H); 7.40 (t, J=7.5 Hz, 2 Hz); 7.36-7.26 (m, 2H); 5.65 (d, J=9.2 Hz, 1H); 4.72-4.59 (m, 1H); 4.46-4.27 (m, 2H); 4.24-4.16 (m, 1H); 4.12-3.99 (m, 1H); 3.94-3.53 (m, 6H); 3.48-3.33 (m, 1H); 2.97 (bs, 4H); 2.46-2.26 (m, 10H); 2.08-1.83 (m, 4H); 1.79-1.64 (m, 1H); 1.43 (s, 9H); 1.07-0.90 (m, 24H).

tert-Butyl 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoate (59.2 g, 64.8 mmol) dissolved in DCM (50 mL) was added to TFA/H$_2$O mixture (95:5, 400 mL) and stirred for 2 hrs. Then solvent was evaporated and the residue was co-evaporated with toluene for three times. The residue was dissolved in DCM (800 mL) and washed with water (3×800 mL). The solvent was evaporated under reduced pressure. The residue was purified by column chromatography (Silicagel 60, 0.063-0.040 mm; eluent: DCM/methanol 60:1-10:1) affording 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoic acid as white powder.

Yield: 42.1 g (76%).

1H NMR spectrum (300 MHz, AcOD-d$_4$, 80° C., $\delta_H$): 7.79 (d, J=7.3 Hz, 2H); 7.64 (d, J=7.5 Hz, 2H); 7.39 (t, J=7.4 Hz, 2H); 7.36-7.26 (m, 2H); 4.83 (bs, 1H); 4.48-4.30 (m, 2H); 4.27-4.19 (m, 1H); 4.19-3.62 (m, 7H); 3.61-3.46 (m, 1H); 3.28-2.90 (m, 4H); 2.55 (t, J=6.7 Hz, 2H); 2.43 (s, 8H); 2.01-1.81 (m, 4H); 1.07-0.88 (m, 24H).

Wang resin 0.63 mmol/g (25.7 g, 16.2 mmol) was left to swell in tetrahydrofuran (250 mL) for 20 minutes. A solution of the 4-((((9H-fluoren-9-yl)methoxy)carbonyl)amino)-5-(bis(2-((1-(4,4-dimethyl-2,6-dioxocyclohexylidene)-3-methylbutyl)amino)ethyl)amino)-5-oxopentanoic acid (42.0 g, 48.5 mmol) in THF (250 mL) was added to resin and then DIC (7.60 mL, 48.5 mmol) and 4-dimethylaminopyridine (DMAP, 200 mg, 1.62 mmol). The mixture was shaken for 18 hrs. The resin was filtered off and washed with DCM (6×250 mL). Resin was treated with a solution of acetic anhydride (40 mL), pyridine (40 mL) in DMF (360 mL) for 15 min. and washed with DCM (6×250 mL) affording compound (1) as yellow solid.

Yield: 36.0 g.

Loading: 51% (0.321 mmol/g).

Wang resin-bound compound (1) (2.85 g, 0.92 mmol) was swollen in DCM (20 mL) for 20 min. The Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL). Solution of (S)-2-(9H-fluoren-9-ylmethoxycarbonylamino)-pentanedioic acid 1-tert-butyl ester (Fmoc-LGlu-OtBu, 1.17 g, 2.75 mmol), O-(6-chloro-benzotriazol-1-yl)-N,N,N',N'-tetramethyluronium tetrafluoroborate (TCTU, 0.98 g, 2.75 mmol) and DIPEA (0.96 mL, 5.49 mmol) in DMF (60 mL) was added to resin and mixture was shaken for 3 hrs. Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL). A solution of {2-[2-(9H-fluoren-9-ylmethoxycarbonylamino)-ethoxy]-ethoxy}-acetic acid (Fmoc-OEG-OH, 1.06 g, 2.75 mmol), O-(6-chloro-benzotriazol-1-yl)-N,N,N',N'-tetramethyluronium tetrafluoroborate (TCTU, 0.98 g, 2.75 mmol) and DIPEA (0.96 mL, 5.49 mmol) in DMF (50 mL) was added to resin and the mixture was shaken for 2 hours. Resin was filtered and washed with DMF (3×70 mL), DCM (3×70 mL) and DMF (3×70 mL). Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL).

A solution of 4-((((9H-fluoren-9-yl)methoxy)carbonyl)amino)butanoic acid (Fmoc-GABA, 0.88 g, 2.70 mmol), O-(6-chloro-benzotriazol-1-yl)-N,N,N',N'-tetramethyluronium tetrafluoroborate (TCTU, 0.96 g, 2.70 mmol) and DIPEA (0.94 mL, 5.40 mmol) in DMF (50 mL) was added to resin and the mixture was shaken for 2 hours. Resin was filtered and washed with DMF (3×70 mL), DCM (3×70 mL) and DMF (3×70 mL). Fmoc group was removed by treatment with 20% piperidine in DMF (1×5 min, 1×30 min, 2×40 mL). Resin was washed with DMF (3×70 mL), 2-propanol (3×70 mL) and DCM (3×70 mL). A solution of 1-(chloro-diphenyl-methyl)-4-methyl-benzene (MttCl, 0.79 g, 2.70 mmol) and DIPEA (0.94 mL, 5.4 mmol) in dry DCM (60 mL) was added to resin and mixture was shaken for 3 hrs. The resin was filtered off and washed with DCM (3×70 mL) and DMF (3×70 mL). The IvDde group was removed by treatment with 2% hydrazine monohydrate in DMF (3×3 min, 3×30 mL). The resin was washed with DMF (5×40 mL). A solution of chloroacetic acid (0.51 g, 5.40 mmol), DIC (0.85 mL, 5.40 mmol) and 2,4,6-trimethylpyridine (1.43 mL, 10.8 mmol) in DMF (50 mL) was added to the resin and the mixture was shaken for 2.5 hrs. The resin was filtered off and washed with DMF (3×70 mL) and DCM (3×70 mL). The Mtt group was removed by treatment with 80% 1,1,1,3,3,3-hexafluoro-2-propanol in DCM (2×10 min, 2×30 min, 4×50 mL). The resin was washed with DCM (5×50 mL) and DMF (4×50 mL). A solution of bromoacetic acid (0.38 g, 2.70 mmol) and DIC (0.42 mL, 2.70 mmol) in DMF (50 mL) was added to resin and mixture was shaken for 2.5 hrs. Resin was filtered and washed with DMF (3×70 mL) and DCM (3×70 mL). The product was cleaved from resin by treatment with cleavage cocktail of TFA/TIS/H$_2$O (95:2.5:2.5, 26 mL) for 1 hr. The resin was filtered off and washed with DCM (6×40 mL). Solutions were combined and solvents were evaporated to dryness. The residue was purified by HPLC (Column Gemini C18, 5 um; 50×250 mm; MeCN/H₂O 5:95 to 40:60 during 180 min. and 5:95 to 35:65 during 60 min.+0.05% TFA) and freeze-dried to give title compound (2) as white solid.

Yield: 336 mg (43%).

$^1$H NMR spectrum (300 MHz, AcOD-d$_4$, $\delta_H$): 5.07 (dd, J=9.9 and 2.9 Hz, 1H); 4.72 (dd, J=8.7 and 4.7 Hz, 1H); 4.22-4.12 (m, 6H); 3.96 (s, 2H); 3.93-3.37 (m, 16H); 3.33 (t, J=6.8 Hz, 3H); 2.59-2.29 (m, 7H); 2.10 (d, J=4.9 Hz, 2H); 1.97-1.80 (m, 3H).

LC-MS purity: 100%.

LC-MS Rt (Kinetex 4.6 mm×50 mm, MeCN/H₂O 5:95 to 100:0+0.1% FA): 2.86 min.

LC-MS m/z: 866.5 (M+H)$^+$.

UPLC purity: 98.7% (214 nm).

UPLC Rt (Acquity UPLC BEHC 18, 1.7 μm, 2.1×150 mm; MeCN/H₂O 5:95 to 100:0+0.05% TFA): 2.74 min.

Trivalent Linker 7

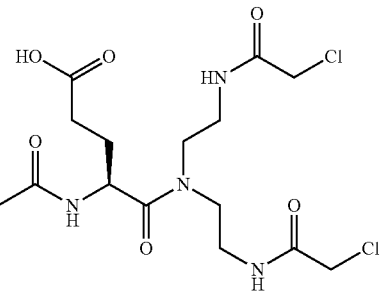

(S)-4-(2-{2-[((S)-1-{Bis-[2-(2-chloro-acetylamino)-ethyl]-carbamoyl}-3-carboxy-propylcarbamoyl)-methoxy]-ethoxy}-ethylcarbamoyl)-2-(2-bromo-acetylamino)-butyric acid Reaction scheme:

1. Loading: REaD 24026, DIC, DMAP, THF
2. Fmoc cleavage: 20% piperidine in DMF
3. Loading: Fmoc—OEG—OH, TCTU, DIPEA
4. Fmoc cleavage: 20% piperidine in DMF
5. Loading: Fmoc-Glu-OtBu, TCTU, DIPEA
6. Dde cleavage: 2% hydrazine in DMF
7. ClCH₂COOH, PyBroP, DIPEA
8. Mtt cleavage: 80% HFIP in DCM
9. BrCH₂COOH, DIC
10. TFA

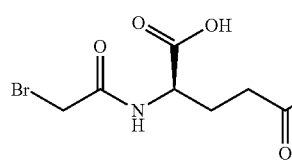

Wang resin
1

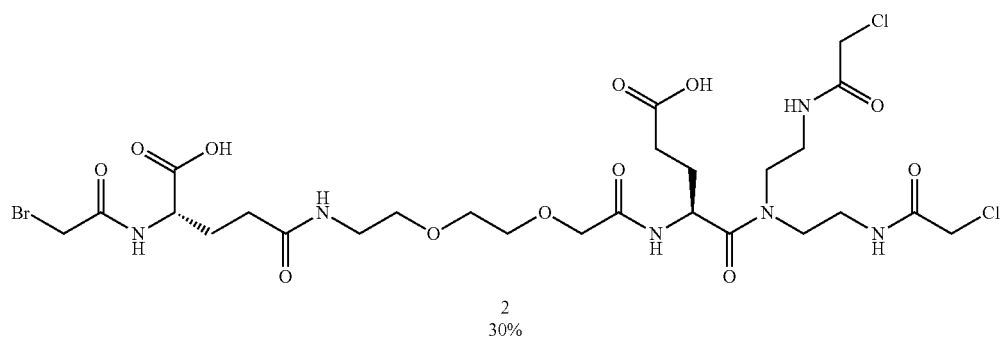

2
30%

Synthetic Protocol:

Wang resin 0.63 mmol/g (1, 5.08 g, 3.20 mmol) was left to swell in THF (60 mL) for 45 minutes. A solution of (S)-4-(bis-{2-[1-(4,4-dimethyl-2,6-dioxo-cyclohexylidene)-ethylamino]-ethyl}-carbamoyl)-4-(9H-fluoren-9-yl-methoxycarbonylamino)-butyric acid (7.52 g, 9.61 mmol), DIC (1.49 mL, 9.61 mmol) and 4-dimethylaminopyridine (DMAP, 0.04 g, 0.32 mmol) in THF (50 mL) was added to resin and the mixture was shaken overnight. Resin was filtered and washed with DMF (2×50 mL), DCM (2×50 mL) and DMF (2×50 mL). The Fmoc group was removed by treatment with 20% piperidine in DMF (2×50 mL, 1×5 min, 1×20 min). Resin was washed with DMF (2×50 mL), 2-propanol (2×50 mL), DCM (2×50 mL) and DMF (2×50 mL). A solution of {2-[2-(9H-fluoren-9-ylmethoxycarbonylamino)-ethoxy]-ethoxy}-acetic acid (Fmoc-OEG-OH, 2.47 g, 6.41 mmol), TCTU (2.28, 6.41 mmol) and DIPEA (2.01 mL, 11.5 mmol) in DMF (50 mL) was added to resin and mixture was shaken for 2 hrs. Resin was filtered and washed with DMF (2×50 mL), DCM (2×50 mL) and DMF (2×50 mL). The Fmoc group was removed by treatment with 20% piperidine in DMF (2×50 mL, 1×5 min, 1×20 min). Resin was washed with DMF (2×50 mL), 2-propanol (2×50 mL), DCM (2×50 mL) and DMF (2×50 mL). A solution of (S)-2-(9H-fluoren-9-ylmethoxycarbonylamino)-pentanedioic acid 1-tert-butyl ester (Fmoc-Glu-OtBu, 2.04 g, 4.80 mmol), TCTU (1.71, 4.80 mmol) and DIPEA (1.67 mL, 9.61 mmol) in DMF (50 mL) was added to resin and mixture was shaken for 1.5 hrs. Resin was filtered and washed with DMF (2×50 mL), DCM (2×50 mL) and DMF (2×50 mL). The Fmoc group was removed by treatment with 20% piperidine in DMF (2×50 mL, 1×5 min, 1×20 min). Resin was washed with DMF (2×50 mL), 2-propanol (2×50 mL), DCM (2×50 mL) and DMF (2×50 mL). A solution of 1-(chloro-diphenyl-methyl)-4-methyl-benzene (MttCl, 1.13 g, 3.84 mmol) and DIPEA (1.67 mL, 9.61 mmol) in dry DCM (50 mL) was added to resin and mixture was shaken for 2 hrs. Resin was filtered and washed with DCM (4×50 mL) and DMF (4×50 mL). Dde group was removed by treatment with 2% hydrazine in DMF (3×50 mL, 3×3 min). Resin was washed with DMF (8×50 mL). A solution of chloroacetic acid (0.91 g, 9.61 mmol), PyBrOP (4.48 g, 9.61 mmol) and DMF (3.35 mL, 19.2 mmol) in DMF (50 mL) was added to resin and mixture was shaken overnight. Ninhydrin test was still positive, therefore recoupling was made. A solution of chloroacetic acid (0.91 g, 9.61 mmol), PyBrOP (4.48 g, 9.61 mmol) and DIPEA (3.35 mL, 19.2 mmol) in DMF (50 mL) was added to resin and mixture was shaken for 3 hrs. Resin was filtered and washed with DMF (4×50 mL) and DCM (4×50 mL). Mtt group was removed by treatment with 80% 1,1,1,3,3,3-hexafluoro-2-propanol in DCM (7×50 mL, 2×10 min, 5×30 min). Resin was washed with DCM (5×50 mL) and DMF (4×50 mL). A solution of bromoacetic acid (8.90 g, 64.1 mmol) and DIC (8.43 mL, 54.5 mmol) in DMF (50 mL) was added to resin and mixture was shaken for 20 minutes. Resin was filtered and washed with DMF (4×30 mL) and DCM (10×30 mL). The product was cleaved from resin by treatment with TFA (50 mL) for 1.5 hrs. Resin was filtered off and washed with TFA (1×50 mL) and DCM (2×50 mL). Solutions were combined and solvents were evaporated. The residue was co-evaporated with toluene twice and purified by preparative LC/MS (SunFire Prep C18 OBD 5m, 19×100 mm, gradient 5-100% MeCN/H$_2$O in 0.1% FA). Fractions containing pure product were combined and freeze-dried yielding the title compound as beige solid.

Yield: 150 mg (30%).

1H NMR spectrum (300 MHz, AcOD-d$_4$, $\delta_H$): 5.19-5.05 (m, 1H); 4.72-4.56 (m, 1H); 4.27-4.07 (m, 6H); 4.06-3.37 (m, 18H); 2.60-2.37 (m, 4H); 2.36-2.22 (m, 1H); 2.21-1.87 (m, 3H).

LC-MS purity: 100%.

LC-MS Rt (Kinetex 4.6 mm×50 mm, MeCN/water 05:95 to 100:0+0.1% FA): 2.94 min.

LC-MS m/z: 780.4 (M+H)$^+$.

Trivalent Linker 8

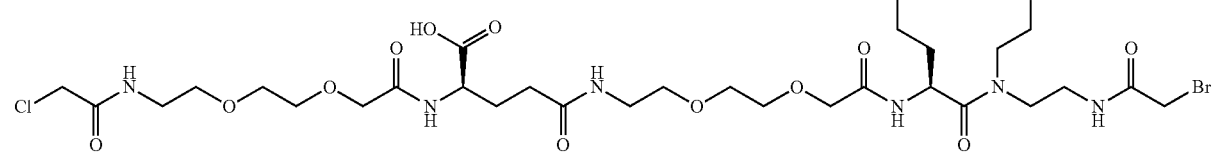

(4S,18S)-4-(bis(2-(2-Bromoacetamido)ethyl)carbamoyl)-18-(2-(2-(2-(2-chloroacetamido)ethoxy)ethoxy)acetamido)-6,15-dioxo-8,11-dioxa-5,14-diazanonadecanedioic acid Reaction scheme:

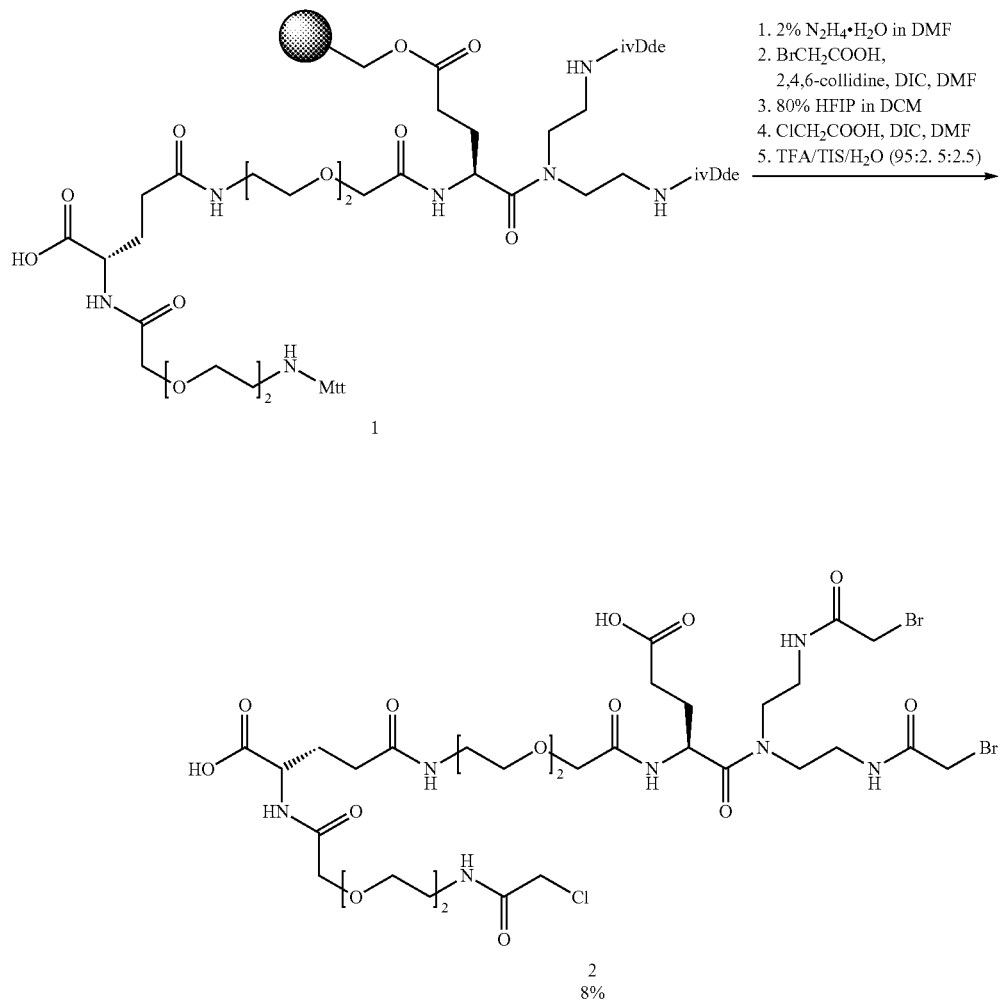

Synthetic Protocol:

IvDde group from one portion of resin (1) (8.25 g, 2.71 mmol, preparation as described in Example 5) was removed by treatment with 2% hydrazine monohydrate in DMF (3×3 min, 3×50 mL). Resin was washed with DMF (6×50 mL). A solution of bromoacetic acid (2.26 g, 16.3 mmol), DIC (2.52 mL, 16.3 mmol) and 2,4,6-collidine (4.30 mL, 32.5 mmol) in DMF (50 mL) was added to resin and mixture was shaken for 2.5 hrs. Resin was filtered and washed with DMF (3×50 mL), DCM (3×50 mL), DMF (3×50 mL) and DCM (4×50 mL). Mtt group was removed by treatment with 80% 1,1,1,3,3,3-hexafluoro-2-propanol in DCM (2×10 min, 2×30 min, 4×50 mL). Resin was washed with DCM (5×50 mL) and DMF (4×50 mL). A solution of chloroacetic acid (5.12 g, 54.2 mmol) and DIC (7.13 mL, 46.1 mmol) in DMF (50 mL) was added to resin and mixture was shaken for 30 min. Resin was filtered and washed with DMF (4×50 mL) and DCM (10×50 mL). The product was cleaved from resin by treatment with cleavage cocktail of TFA/TIS/H$_2$O (95:2.5:2.5, 50 mL) for 2 hrs. Resin was filtered and washed with TFA/DCM mixture (1:1, 50 mL) and DCM (10×30 mL). Solutions were combined and solvents were evaporated to dryness. The residue was purified by HPLC (column X-Bridge3 C18, OBD, 5 µm, 50×250 mm MeCN/H$_2$O 3:35 to 35:40+0.05% TFA) to give (4S,18S)-4-(bis(2-(2-bromoacetamido)ethyl)carbamoyl)-18-(2-(2-(2-(2-chloroacetamido)ethoxy)ethoxy)acetamido)-6,15-dioxo-8,11-dioxa-5,14-diazanonadecanedioic acid (2) as white solid.

Yield: 213 mg (8%).

$^1$H NMR spectrum (300 MHz, AcOD-d$_4$, 80° C., $\delta_H$): 5.12 (dd, J=9.5 and 3.9 Hz, 1H); 4.69 (dd, J=8.0 and 5.4 Hz, 1H); 4.19-4.10 (m, 6H); 3.94 (s, 2H); 3.90-3.43 (m, 24H); 2.55 (t, J=7.0 Hz, 2H); 2.48 (m, 2H); 2.41-1.99 (m, 4H).

LC-MS purity: 100%.

LC-MS Rt (Kinetex 4.6 mm×50 mm, MeCN/H$_2$O 5:95 to 100:0+0.1% FA): 3.06 min.

LC-MS m/z: 970.5 (M+H)$^+$.

UPLC purity: 98.3% (214 nm).

UPLC Rt (Acquity UPLC BEHC 18, 1.7 µm, 2.1×150 mm; MeCN/H$_2$O 5:95 to 95:5+0.05% TFA): 1.66 min.

Trivalent Linker 9

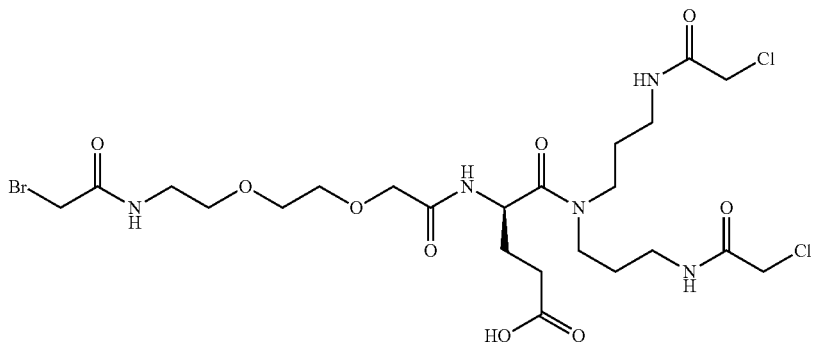 [SMILES: O=C(O)CC[C@@H](NC(=O)COCCOCCNC(=O)CBr)C(=O)N(CCCNC(=O)CCl)CCCNC(=O)CCl]

(4S)-5-[bis[3-[(2-chloroacetyl)amino]propyl]amino]-4-[[2-[2-[2-[(2-bromoacetyl)amino]ethoxy]ethoxy]acetyl]amino]-5-oxo-pentanoic acid Trivalent linker 9 was prepared in a similar way as described in Example 1 for Trivalent linker 1 substituting 2,2'-(((azanediylbis(ethane-2,1-diyl))bis(azanediyl))bis(3-methylbutan-1-yl-1-ylidene))bis(5,5-dimethylcyclohexane-1,3-dione) with 2,2'-(((azanediylbis(propane-3,1-diyl))bis(azanediyl))bis(3-methylbutan-1-yl-1-ylidene))bis(5,5-dimethylcyclohexane-1,3-dione).

Crude (4S)-5-[bis[3-[(2-chloroacetyl)amino]propyl]amino]-4-[[2-[2-[2-[(2-bromoacetyl)amino]ethoxy]ethoxy]acetyl]amino]-5-oxo-pentanoic acid was purified by preparative LC-MS (Column Labio C18, 50×500 mm, MeCN/water+0.05% TFA, gradient 10:40 during 120 min to give pure (4S)-5-[bis[3-[(2-chloroacetyl)amino]propyl]amino]-4-[[2-[2-[2-[(2-bromoacetyl)amino]ethoxy]ethoxy]acetyl]amino]-5-oxo-pentanoic acid as colorless oil.

Yield: 0.25 g (56%).
LC-MS purity: 100% (ELSD).
LC-MS Rt (Kinetex C18, 4.6 mm×50 mm, MeCN/H$_2$O 5:95 to 100:0+0.1% FA): 3.01 min.
LC-MS m/z: 680.2 (M+H)$^+$.
$^1$H NMR spectrum (300 MHz, CDCl$_3$, $\delta_H$): 7.71-7.60 (m, 2H); 7.49-7.41 (m, 1H); 7.35-7.29 (m, 1H); 5.17-5.07 (m, 1H); 4.43 (bs, 1H); 4.12-3.98 (m, 6H); 3.90 (s, 2H); 3.76-3.57 (m, 8H); 3.50-3.14 (m, 8H); 2.50-2.42 (m, 2H); 2.10-1.70 (m, 6H).

Trivalent Linker 10

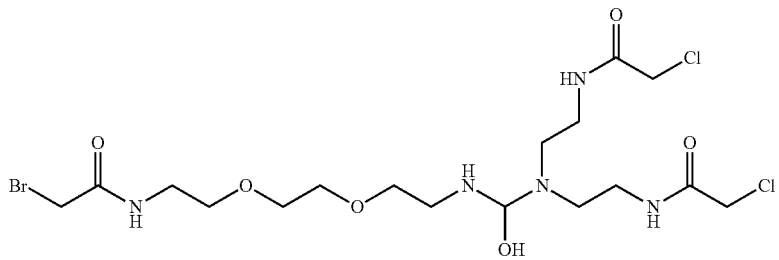 [SMILES: O=C(CCl)NCCN(CCNC(=O)CCl)C(O)NCCOCCOCCNC(=O)CBr]

N-[2-[2-[2-[2-[(2-bromoacetyl)amino]ethoxy]ethoxy]ethylcarbamoyl-[2-[(2-chloroacetyl)amino]ethyl]amino]ethyl]-2-chloro-acetamide Reaction scheme:

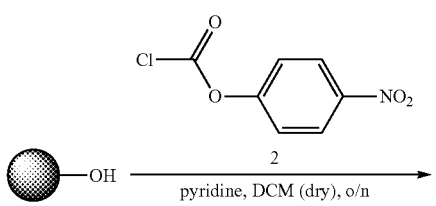

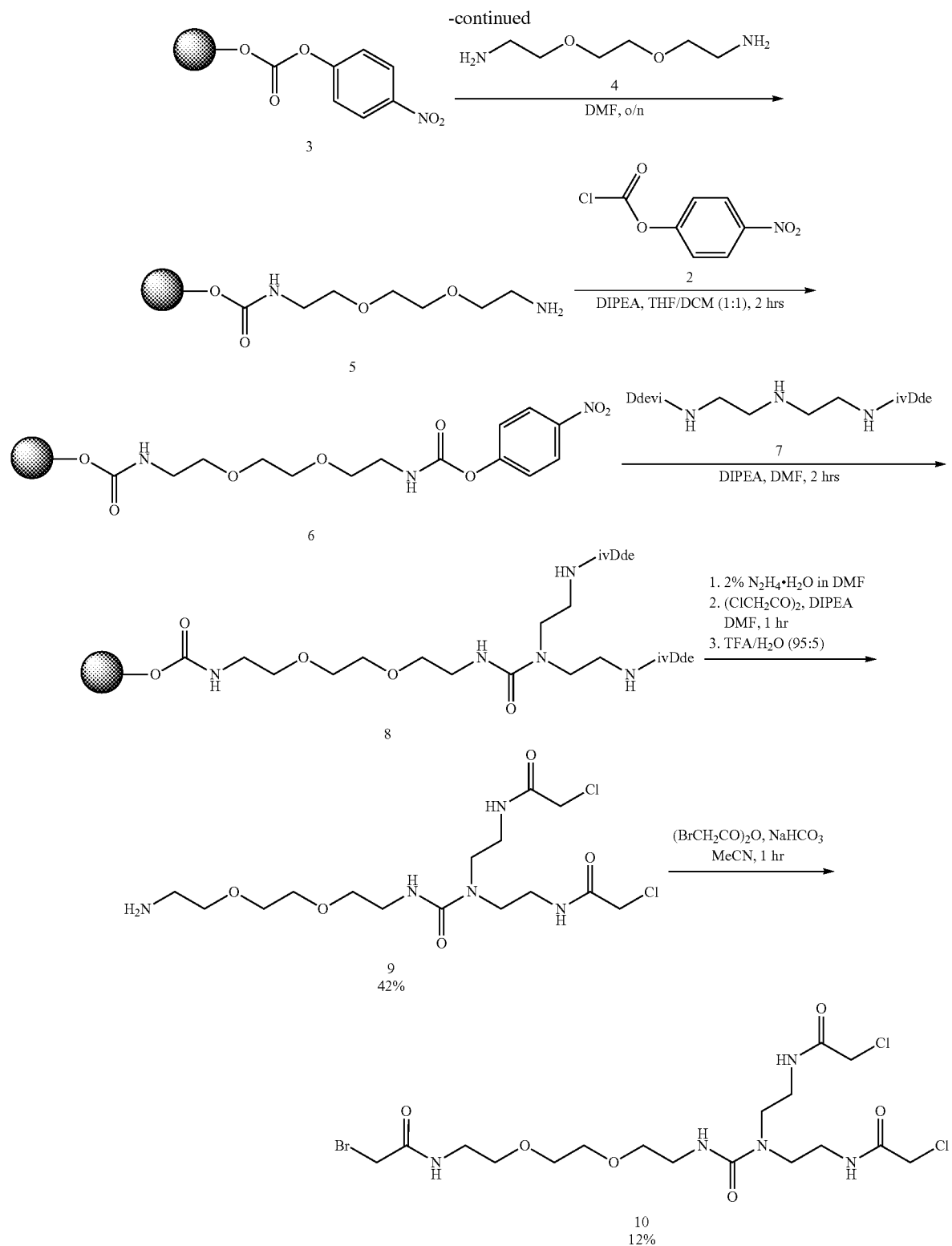

Synthetic Protocol:

Wang-OH resin 0.53 mmol/g (1, 3.85 g, 2.04 mmol) was left to swell in dry DCM (40 mL) for 30 min. A solution of 4-nitrophenyl carbonochloridate (2, 0.27 g, 1.36 mmol) and pyridine (0.12 mL, 1.50 mmol) in dry DCM (40 mL) was added to resin (1) and mixture was shaken overnight. Resin (3) was washed with ice water (1×30 mL), ice water/1,4-dioxane mixture (1:1, 1×30 mL), DMF (3×30 mL) and DCM (3×30 mL).

A solution of 2,2'-(ethane-1,2-diylbis(oxy))bis(ethan-1-amine) (4) (0.59 mL, 4.08 mmol) in DMF (30 mL) was added to resin (3) and mixture was shaken overnight. Resin (5) was washed with DMF (4×30 mL), DCM (3×30 mL), DMF (2×30 mL) and DCM (2×30 mL).

A solution of 4-nitrophenyl carbonochloridate (2) (1.10 g, 5.44 mmol) and N,N-diisopropylethylamine (1.88 mL, 6.80 mmol) in DMF/tetrahydrofuran mixture (1:1, 30 mL) was added to resin (5) and mixture was shaken for 2 hrs. Resin (6) was washed with DMF (4×30 mL), DCM (4×30 mL) and DMF (4×30 mL).

A solution of 2,2'-(((azanediylbis(ethane-2,1-diyl))bis(azanediyl))bis(3-methylbutan-1-yl-1-ylidene))bis(5,5-dimethylcyclohexane-1,3-dione) (7) (1.40 g, 2.72 mmol) and N,N-diisopropylethylamine (0.47 mL, 2.72 mmol) in DMF (30 mL) was added to resin (6) and mixture was shaken for 2 hrs. Resin (8) was washed with DMF (4×30 mL), DCM (4×30 mL) and DMF (4×30 mL).

The ivDde-protecting groups were removed by treatment with 2% solution of hydrazine monohydrate in DMF (3×5 min, 3×30 mL). Resin was washed with DMF (3×30 mL), DCM (3×30 mL) and DMF (3×30 mL). Solution of chloroacetic anhydride (0.93 g, 5.44 mmol) and N,N-diisopropylethylamine (1.90 mL, 10.9 mmol) in DMF (30 mL) was added to resin and the mixture was shaken for 1 hr. Resin was filtered and washed with DMF (3×30 mL), DCM (3×30 mL), DMF (3×30 mL) and DCM (10×30 mL). The product (9) was cleaved from resin by treatment with 95% trifluoroacetic acid in water (30 mL) for 3 hrs. Resin was filtered off and washed with DCM (3×10 mL). Solutions were combined and solvents were evaporated to dryness. The residue was dissolved in 60% aqueous solution of MeCN (50 mL) and freeze-dried to give the desired compound (9) as a thick yellow oil.

Yield: 240 mg (42%).
LC-MS purity: 93% (ELSD).
LC-MS Rt (Kinetex C18, 4.6 mm×50 mm, MeCN/H$_2$O 5:95 to 100:0+0.1% FA): 2.42 min.
LC-MS m/z: 430.29 (M+H)$^+$.

A stirred solution of the above compound (9) (0.24 g, 0.56 mmol) in MeCN (20 mL) was cooled at 0° C. and bromoacetic anhydride (0.22 g, 0.84 mmol) and sodium bicarbonate (0.18 g, 2.09 mmol) were added. The reaction mixture was stirred for 1 hr at 0° C. Freeze-drying of the reaction mixture gave the title crude compound (10) as colorless oil. The crude compound (10) was twice purified by preparative LC/MS (SunFire Prep C18 OBD, 5 µm, 19×100 mm, MeCN/H$_2$O 5:95 to 100:0+0.1% FA) to give title compound N-[2-[2-[2-[2-[(2-bromoacetyl)amino]ethoxy]ethoxy]ethylcarbamoyl-[2-[(2-chloroacetyl)amino]ethyl]amino]ethyl]-2-chloro-acetamide as colorless oil.

Yield: 35.0 mg (12%).
$^1$H NMR spectrum (300 MHz, CDCl$_3$, δ$_H$): 7.45 (bs, 2H); 7.27 (bs, 1H); 6.06-5.93 (m, 1H); 4.06 (s, 4H); 3.90 (s, 2H); 3.64 (s, 4H); 3.62-3.55 (m, 4H); 3.53-3.38 (m, 12H).
LC-MS purity: 100% (ELSD).
LC-MS Rt (Kinetex C18, 4.6 mm×50 mm, MeCN/H$_2$O 5:95 to 100:0+0.1% FA): 2.91 min.
LC-MS m/z: 552.3 (M+H)$^+$.

Trivalent Linker 11

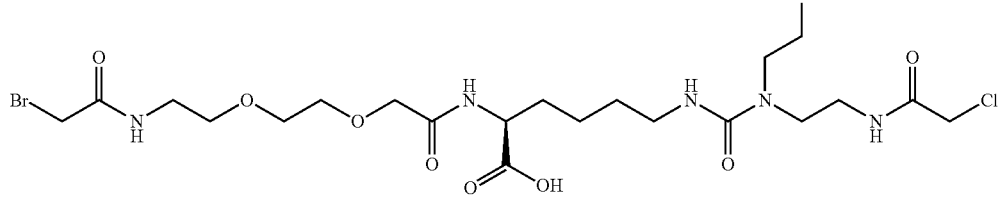

(2R)-6-[bis[2-[(2-chloroacetyl)amino]ethyl]carbamoylamino]-2-[[2-[2-[2-[(2-bromoacetyl)amino]ethoxy]ethoxy]acetyl]amino]hexanoic acid Trivalent linker 11 was prepared in a similar way as described for Trivalent linker 10.

Trivalent Linker 12

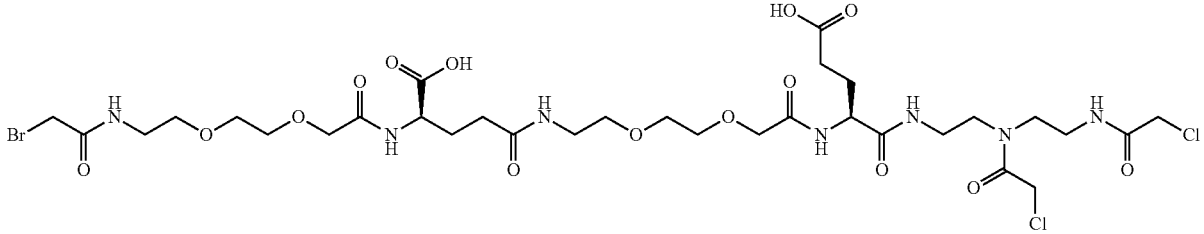 [SMILES: O=C(O)CC[C@H](NC(=O)COCCOCCNC(=O)CC[C@@H](NC(=O)COCCOCCNC(=O)CBr)C(=O)O)C(=O)NCCN(CCNC(=O)CCl)C(=O)CCl]

(2R)-2-[[2-[2-[2-[(2-bromoacetyl)amino]ethoxy]
ethoxy]acetyl]amino]-5-[2-[2-[2-[[(1S)-3-carboxy-1-
[2-[(2-chloroacetyl)-[2-[(2-chloroacetyl)amino]
ethyl]amino]ethylcarbamoyl]propyl]amino]-2-oxo-
ethoxy]ethoxy]ethylamino]-5-oxo-pentanoic acid Reaction scheme:

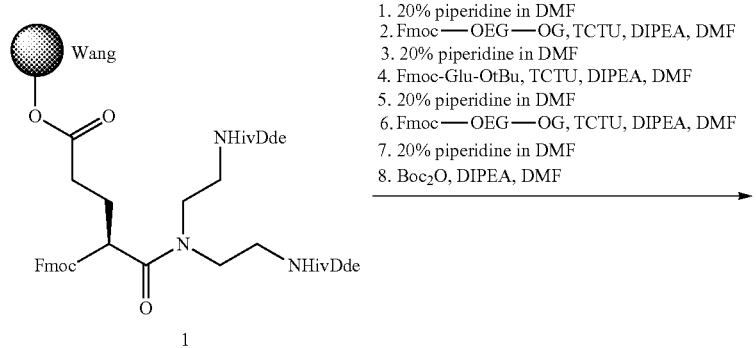

1. 20% piperidine in DMF
2. Fmoc—OEG—OG, TCTU, DIPEA, DMF
3. 20% piperidine in DMF
4. Fmoc-Glu-OtBu, TCTU, DIPEA, DMF
5. 20% piperidine in DMF
6. Fmoc—OEG—OG, TCTU, DIPEA, DMF
7. 20% piperidine in DMF
8. Boc$_2$O, DIPEA, DMF

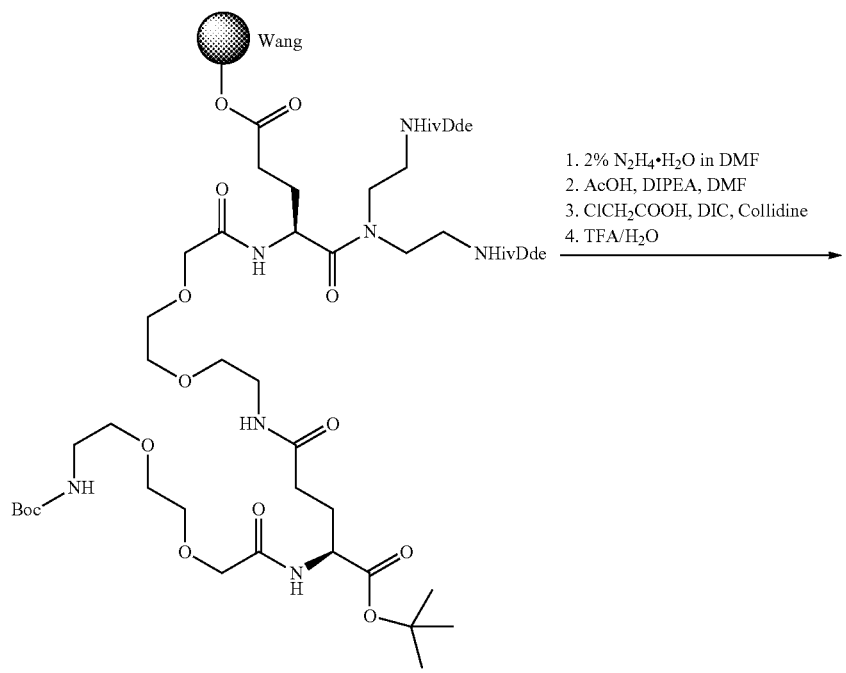

1. 2% N$_2$H$_4$·H$_2$O in DMF
2. AcOH, DIPEA, DMF
3. ClCH$_2$COOH, DIC, Collidine
4. TFA/H$_2$O

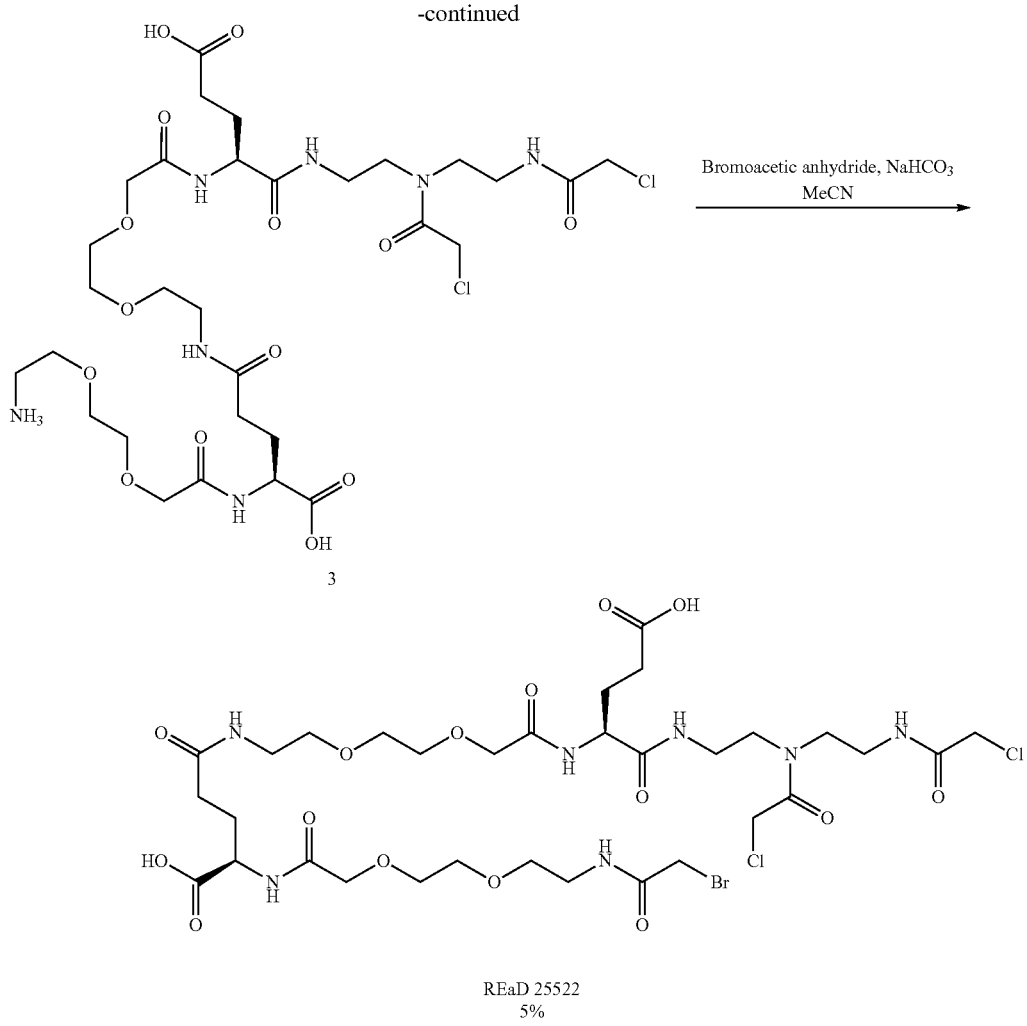

REaD 25522
5%

Synthetic Protocol:

Wang resin-bound compound (1) (1.42 g, 0.70 mmol) was left to swell in DCM (20 mL) for 20 min. Fmoc group was removed by treatment with 20% piperidine in DMF (2×5 min, 1×20 min, 3×10 mL). Resin was washed with DMF (3×15 mL), 2-propanol (3×15 mL) and DCM (3×15 mL). A solution of {2-[2-(9H-fluoren-9-ylmethoxycarbonylamino)-ethoxy]-ethoxy}-acetic acid (Fmoc-OEG-OH, 0.77 g, 2.00 mmol), 5-chloro-1-((dimethylamino)(dimethyliminio)methyl)-1H-benzo[d][1,2,3]triazole 3-oxide tetrafluoroborate (TCTU, 0.71 g, 2.00 mmol) and N,N-diisopropylethylamine (0.63 mL, 3.60 mmol) in DMF (10 mL) was added to resin and the mixture was shaken for 2 hrs. Resin was filtered and washed with DMF (3×15 mL), DCM (3×15 mL) and DMF (3×15 mL). Fmoc group was removed by treatment with 20% piperidine in DMF (2×5 min, 1×20 min, 3×10 mL). Resin was washed with DMF (3×15 mL), 2-propanol (3×15 mL) and DCM (3×15 mL). Solution of (S)-2-(9H-fluoren-9-ylmethoxycarbonylamino)-pentanedioic acid 1-tert-butyl ester (Fmoc-L-Glu-OtBu, 0.85 g, 2.00 mmol), 5-chloro-1-((dimethylamino)(dimethyliminio)methyl)-1H-benzo[d][1,2,3]triazole 3-oxide tetrafluoroborate (TCTU, 0.71 g, 2.00 mmol) and N,N-diisopropylethylamine (0.63 mL, 3.60 mmol) in DMF (10 mL) was added to resin and mixture was shaken for 2 hrs. Resin was filtered and washed with DMF (3×15 mL), DCM (3×15 mL) and DMF (3×15 mL). Fmoc group was removed by treatment with 20% piperidine in DMF (2×5 min, 1×20 min, 3×10 mL). Resin was washed with DMF (3×15 mL), 2-propanol (3×15 mL) and DCM (3×15 mL). A solution of {2-[2-(9H-fluoren-9-ylmethoxycarbonylamino)-ethoxy]-ethoxy}-acetic acid (Fmoc-OEG-OH, 0.77 g, 2.00 mmol), 5-chloro-1-((dimethylamino)(dimethyliminio)methyl)-1H-benzo[d][1,2,3]triazole 3-oxide tetrafluoroborate (TCTU, 0.71 g, 2.00 mmol) and N,N-diisopropylethylamine (0.63 mL, 3.60 mmol) in DMF (10 mL) was added to resin and the mixture was shaken for 2 hrs. Resin was filtered and washed with DMF (3×15 mL), DCM (3×15 mL) and DMF (3×15 mL). Fmoc group was removed by treatment with 20% piperidine in DMF (2×5 min, 1×20 min, 3×10 mL). Resin was washed with DMF (3×15 mL), 2-propanol (3×15 mL) and DCM (3×15 mL).

A solution of di-tert-butyl dicarbonate (0.44 g, 2.00 mmol) and N,N-diisopropylethylamine (0.35 mL, 2.00 mmol) dissolved in DCM (10 mL) was added to resin and the mixture was shaken for 2 hrs. Resin was washed with DMF (3×15 mL), DCM (3×15 mL) and DMF (3×15 mL). Resin was treated with hydrazine monohydrate solution in DMF (2% v/v solution, 3×10 min, 3×15 mL). Resin (2) was washed with DMF (3×15 mL), DCM (3×15 mL) and DMF (3×15 mL). Resin (2) was treated with solution of acetic acid (0.12 mL, 2.00 mmol) and N,N-diisopropylethylamine (0.34 mL, 2.00 mmol) in DMF (10 mL) for 16 hrs. Resin was washed with DMF (3×15 mL), N,N-diisopropylethylamine (0.34 mL, 2.00 mmol) in DMF (10 mL), DCM (2×15 mL) and DMF (3×15 mL). Chloroacetic acid (0.53 g, 5.60 mmol), N,N'-diisopropylcarbodiimide (0.86 mL, 5.60 mmol) and 2,4,6-collidine (0.74 mL, 5.60 mmol) was added and the mixture was shaken for 2 hrs. Resin was washed with DMF (3×15 mL), DCM (6×15 mL). The product was cleaved from resin by treatment with trifluoroacetic acid/water mixture (98:2, 20 mL) for 2 hrs. The solution was concentrated in vacuo and the residue of trifluoroacetic acid was removed by co-evaporation with toluene. A solution of bromoacetic acid (276 mg, 2.00 mmol) and N,N'-dicyclohexylcarbodiimide (DCC, 0.21 mL, 1.00 mmol) was dissolved in MeCN (5 mL), stirred for 15 min and filtered. This solution was added to the crude product cleaved from the resin cooled to 0° C. and sodium hydrogencarbonate (0.24 mmol, 2.80 mmol) was added. The mixture was stirred and let worm to 25° C. for 3 hrs. The mixture was filtered, evaporated and crude product was purified by preparative HPLC (Gemini NX C18, 5 μm, 50×250 mm, MeCN/H$_2$O 5:95 to 45:55 during 180 min and 45:55 to 50:50 during 10 min+0.05% TFA) to give title compound (2R)-2-[[2-[2-[2-[(2-bromoacetyl)amino]ethoxy]ethoxy]acetyl]amino]-5-[2-[2-[2-[[(1S)-3-carboxy-1-[2-[(2-chloroacetyl)-[2-[(2-chloroacetyl)amino]ethyl]amino]ethylcarbamoyl]propyl]amino]-2-oxo-ethoxy]ethoxy]ethylamino]-5-oxo-pentanoic acid Yield: 33 mg (5%).

$^1$H NMR spectrum (300 MHz, AcOD-d$_4$, $\delta_H$): 4.74-4.55 (m, 2H); 4.33 (s, 1H); 4.31 (s, 1H); 4.23-4.10 (m, 6H); 3.98 (s, 2H); 3.83-3.42 (m, 24H); 2.59-2.41 (m, 4H); 2.38-2.08 (m, 4H).

LC-MS purity: 100% (ELSD).

LC-MS Rt (Kinetex C18, 4.6 mm×50 mm, MeCN/water 5:95 to 100:0+0.1% TFA): 3.04 min.

LC-MS m/z: 927.0 (M+H)$^+$.

Example 2

GH-Fc Conjugate 1
GH-trivalent linker 1 intermediate

[(bis(2-(2-Chloroacetamido)ethylamine)))-Glu-OEG-γGlu-OEG]-carbonylmethylene-S$^{101}$-hGH [L101C]

Step 1

Preparation of hGH[L101C]:

hGH[L101C] as obtained above had part of its free cysteine blocked with glutathione and cystamine. Deblocking was performed enzymatically using glutaredoxin II (Grx2) in an equilibrium buffer containing GSH and GSSG. Deblocked hGH[L101C] was separated from low molecular weight GSH/GSSG by buffer exchanged on a Sephadex G25 column.

hGH[101C] used: 100 mg (20.2 mL, Mw=22190.93

Fc used: 200 mg (100 mL in 50 mM ammoniumbicarbonate pH 7.8).

Concentration 2.03 mg/mL

Procedure (step 1): To a vial containing hGH[L101C] (50 mg, 4.95 mg/mL, 225 μM, in 20 mM triethylamine, 100 mM NaCl, pH 8) was added 3 eq. bis(p-sulfonatophenyl)phenylphosphine dihydrate dipotassium (TPPDS, 3.6 mg) at room temperature. After 1 hr incubation, 3 eq. of (4S,18S)-4-(bis(2-(2-chloroacetamido)ethyl)carbamoyl)-18-(2-(2-(2-(2-bromoacetamido)-ethoxy)ethoxy)acetamido)-6,15-dioxo-8,11-dioxa-5,14-diazanonadecanedioic acid (from Example 1, 6.3 mg) along with NaCl (177 mg giving 0.3 M NaCl final concentration) were added and the resulting reaction mixture allowed to incubate at room temperature for 18 hrs, whereupon it was buffer exchanged into 20 mM HEPES, 10 mM EDTA, pH 7.5 and up-concentrated to 22 mg/mL by ultrafiltration (2.2 mL).

Yield=50 mg (99%).

LC-MS (electrospray): Found m/z=22959,43; Calculated m/z=22959,48

Purity on HPLC: 93% at 214 nm.

System: Agilent 1200 series HPLC

Column: Zorbax 300SB-C3, 4.6×50 mm, 3.5μ

Detector: Agilent Technologies LC/MSD TOF (G1969A)

Detector setup: DAD: 280 nm, (G1315A)

Scanning range: m/z min. 100, m/z max. 3000

Linear reflector mode

Positive mode

Conditions: Step gradient: 5% to 90% B

Run-time: 12 minutes: 0-1 min 5% B, 1-8 min 5-90% B, 8-9 min 90% B, 9-9.1 min 90-5% B 9.1-12 min 5% B Flow rate: 1.00 mL/min fixed Column temperature: 40° C.

Eluents: Solvent A: 99.9% H$_2$O, 0.1% Formic Acid

Solvent B: 99.9% MeCN, 0.1% Formic Acid

Reaction overview of step 2 including 3 separate steps describe below

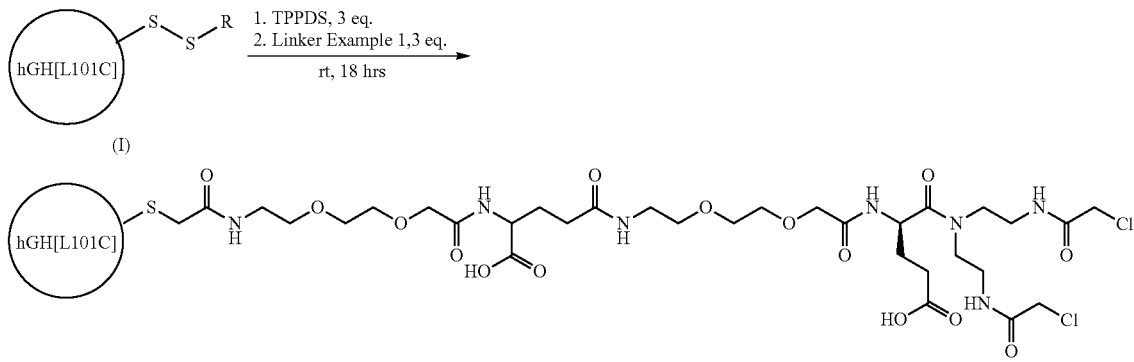

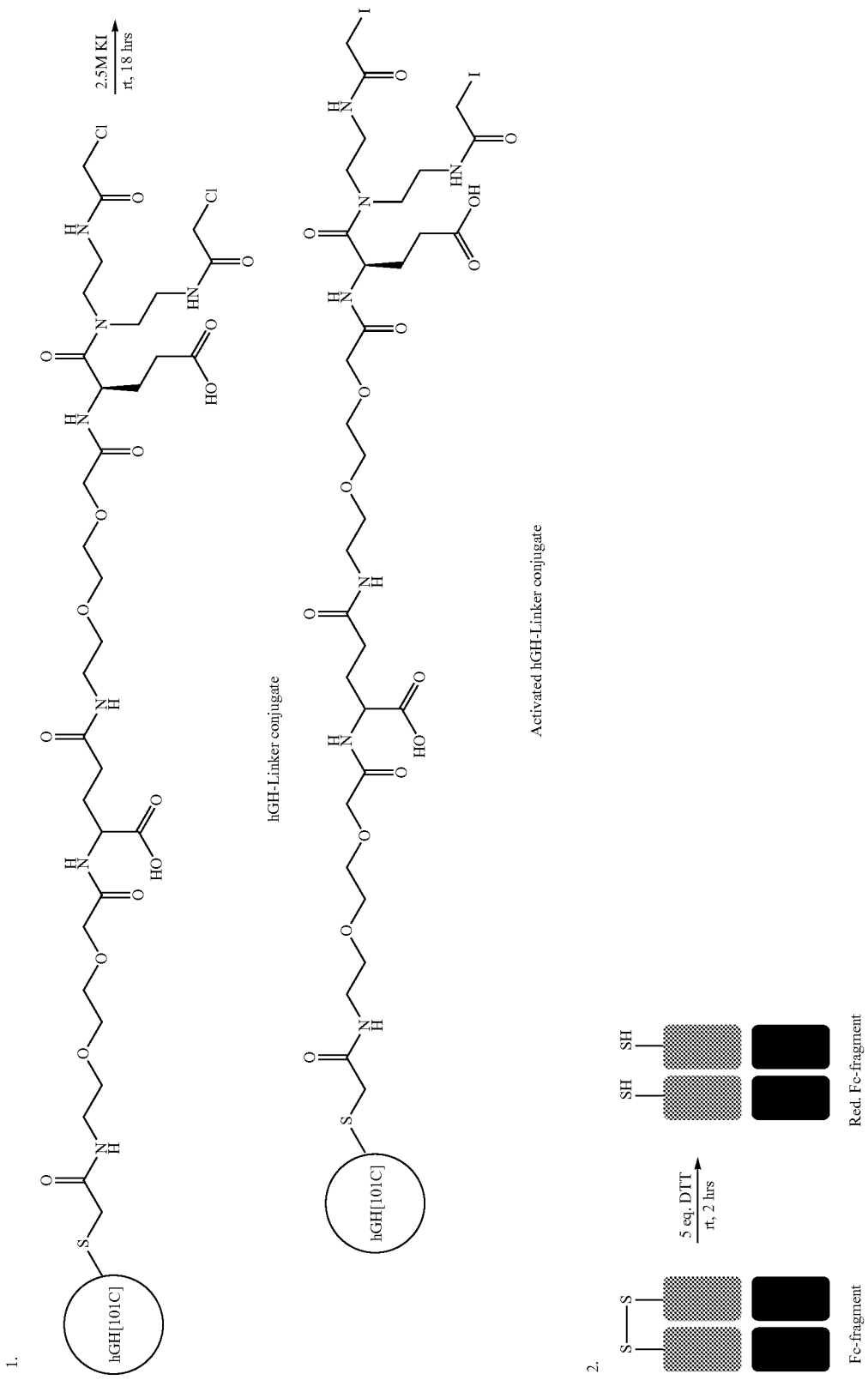

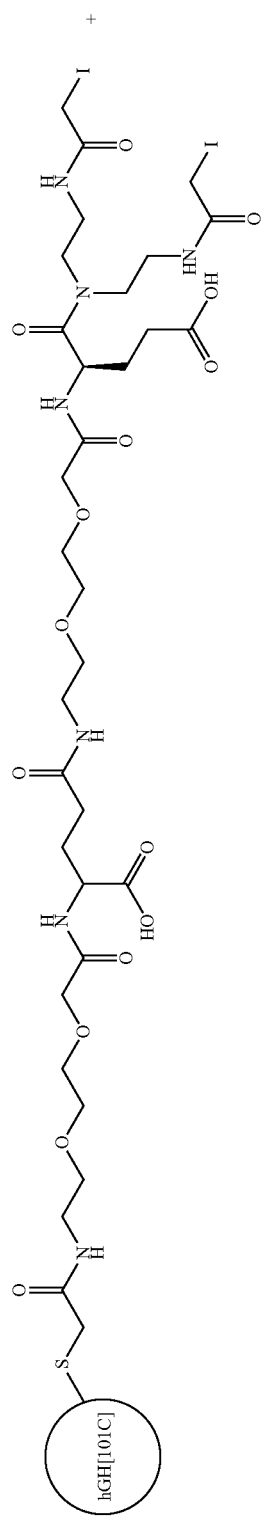
-continued
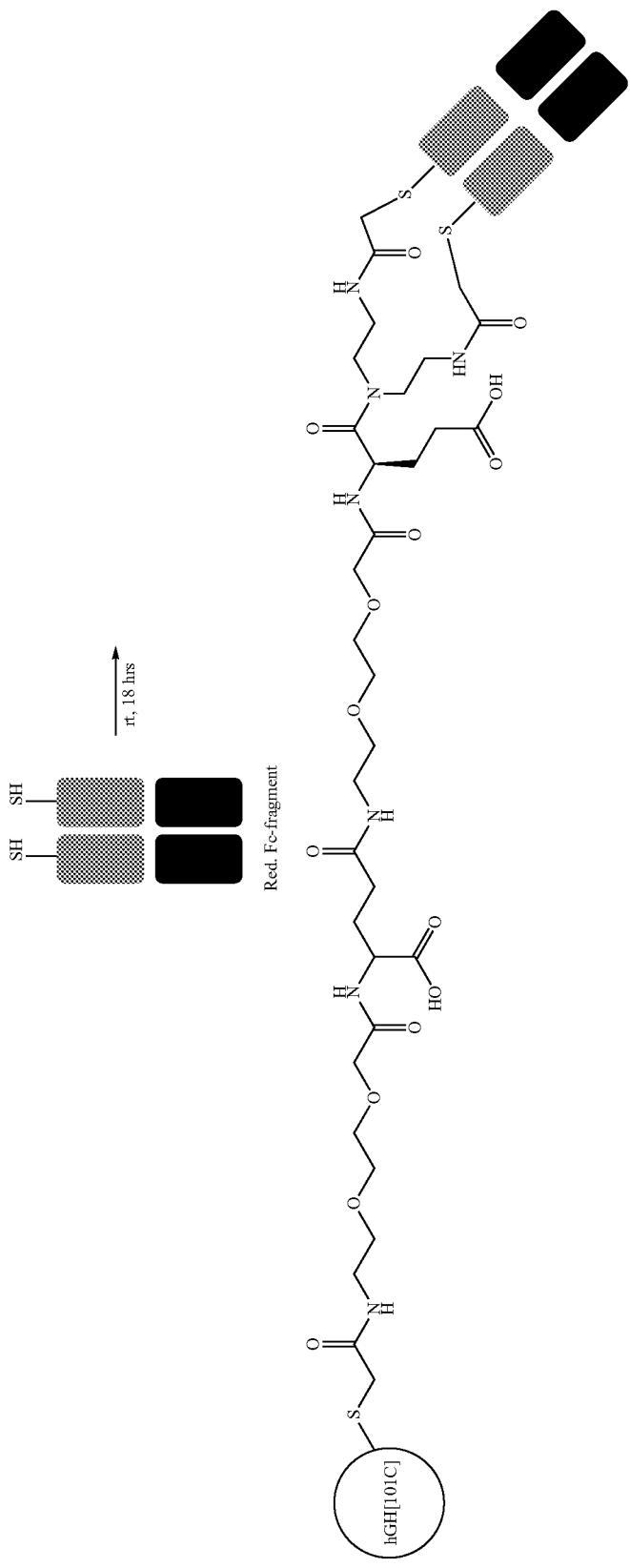
hGH-Fc conjugate

[(bis(2-(2-Fc-S³-acetamido)ethylamine)))-Glu-OEG-γGlu-OEG]-carbonylmethylene-S¹⁰¹-hGH[L101C]

Procedure for step 2:

1. Chloro to Iodo exchange (Finkelstein reaction): The above compound [(bis(2-(2-Chloroacetamido)ethylamine)))-Glu-OEG-γGlu-OEG]-carbonylmethylene-S¹⁰¹-hGH[L101C] from step 1. (2.2 mL, 22 mg/mL, 956 µM) was diluted with 2.2 mL of an aq. 5M KI, 50 mM ascorbic acid solution and incubated at room temperature for 18 hrs in the dark. Finally, the reaction mixture was buffer exchanged in 20 mM HEPES, 10 mM EDTA, pH 7.5 buffer (2.3 mL, 21.7 mg/mL, 945 µM) and used directly in step 3. below.

2. Fc-fragment disulphide bridge reduction: To the Fc-fragment obtained as described above (50 mL, 2.03 mg/mL, 41 µM in 50 mM ammonium bicarbonate, pH 7.8) was added 5 eq. dithiothreitol (DTT, 52 µL of a 195 mM solution in 20 mM HEPES, 10 mM EDTA, pH 7.5) and incubated for 2 hrs at room temperature whereupon the reaction mixture was buffer exchanged and up-concentrated to 4.3 mL (23.6 mg/mL, 475 µM as dimer) by ultrafiltration and used directly in step 3. below.

3. hGH[L101C]-Fc conjugate formation: The hGH[L101C] compound from step 1. (50 mg, 21.7 mg/mL, 945 µM) was mixed with reduced Fc-fragment from step 2. (100 mg, 23.6 mg/mL, 475 µM) obtaining a molar ratio between hGH[L101C] and Fc of 1.1 to 1. The reaction mixture (6.6 mL) was allowed to incubate in the dark for 18 hrs whereupon the desired conjugate was purified from the reaction mixture on a Capto Adhere 16/10 column operated in HIC mode (CV=20 mL; A: 20 mM TEA, pH 7.5; B: 40 mM MES, 40 mM formic acid, pH 3.5; application buffer: 20 mM TEA, 200 mM NaCl, pH 7.5; segment gradient: segment 1: 0-30% B, 1 CV; segment 2: 30-70% B, 15 CV; segment C: 70-100% B, 1 CV; flow 3 mL/min). Fractions containing product were buffer exchanged in PBS giving 50 mg of the desired conjugate (25 mL, 2.0 mg/mL, 27.5 µM).

Yield=50 mg (34%).

LC-MS (electrospray): Found m/z=72682.09; Calculated m/z=72682.13

Purity on HPLC: 96% at 214 nm.

GH-Fc Conjugate 2

[(bis(2-(2-Fc-S³-acetamido)ethylamine)))-Gly]-carbonylmethylene-S1⁰¹-hGH[L101C]

The compound was prepared using the method as described in Example 2 conjugate 1 except that the linker (4S,18S)-4-(bis(2-(2-chloroacetamido)-ethyl)carbamoyl)-18-(2-(2-(2-(2-bromoacetamido)-ethoxy)ethoxy)acetamido)-6,15-dioxo-8,11-dioxa-5,14-diazanonadecanedioic acid (Example 1, linker 1) was substituted with 2-(2-bromoacetamido)-N,N-bis(2-(2-chloroacetamido) ethyl)acetamide (Example 1, linker 2) 100 mg in HEPES/EDTA Purification:

The above reaction mixture was buffer changed to loading buffer (TRIS+salt) and loaded on a G25 column:

Column: 50/30 Sephadex G25 fine

Buffer A: 10 mM Ammonium bicarbonate

Flow: 10 mL/min

Temp: RT

Fractions: 40 mL per fraction

Fraction A4+A5 were pooled and applied onto a Capto Adhere column:

Column: Capto Adhere 16/10

Buffer A: 20 mM TEA pH 7.5

Buffer A2: 40 mM TEA+0,2M NaCl pH 7.5

Buffer B: 40 mM MES+40 mM Formic acid pH 3.5

Gradient 1: 0-30% Buffer B over 1 CV

Gradient 2: 30-70% Buffer B over 15 CV

Gradient 3: 70-100% Buffer B over 1 CV

Flow: 3 mL/min

Temp: RT

Fractions: 1 mL per fraction in peak fractionation

Fractions A6-A10 were pooled and buffer changed to PBS buffer by UF (Amicon ultra 15K).

Concentration=>7.22 mg/mL=>101 mg in total

Yield: 101 mg (31%)

LC-MS (electrospray): Found m/z=72193.48; Calculated m/z=72190.6444

Purity on HPLC: ~100% at 214 nm.

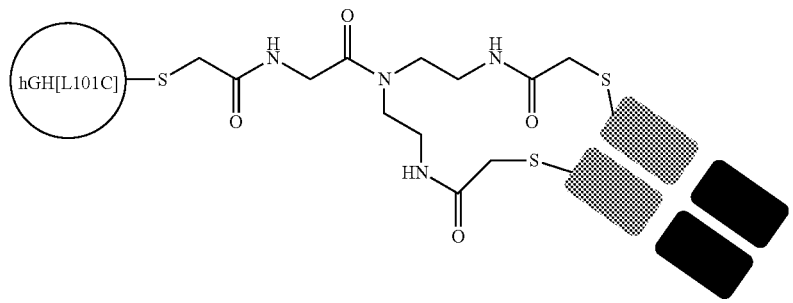

hGH-Fc conjugate

GH-FC Conjugate 3

[(bis(2-(2-Fc-S³-acetamido)ethylamine)))-Gly-OEG]-carbonylmethylene-S¹⁰¹-hGH[L101C]

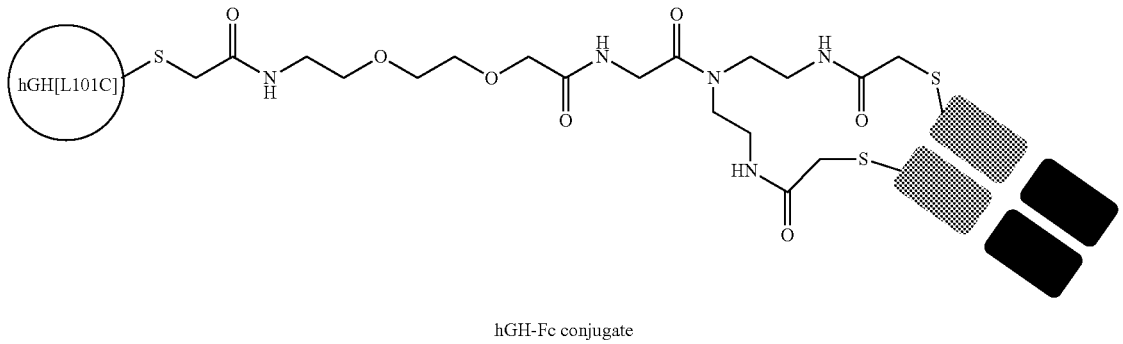

hGH-Fc conjugate

The compound was prepared using the method as described in Example 2 conjugate 1 except that the linker (4S,18S)-4-(bis(2-(2-chloroacetamido)-ethyl)carbamoyl)-18-(2-(2-(2-(2-bromoacetamido)-ethoxy)ethoxy)acetamido)-6,15-dioxo-8,11-dioxa-5,14-diazanonadecanedioic acid (Example 1) was substituted with 2-(2-(2-(2-(2-bromoacetamido)ethoxy)ethoxy)acetamido)-N,N-bis(2-(2-chloroacetamido)-ethyl)acetamide (Example 1, linker 3) 100 mg in HEPES/EDTA hGH[L101C] used: 100 mg (20.2 mL) as described above. Mw=22190.93 Fc used: 200 mg (100 mL in 50 mM ammoniumbicarbonate pH 7.8).

Concentration 2.03 mg/mL
Purification:

The above reaction mixture was buffer changed to loading buffer (TRIS+salt) and loaded on a G25 column:

Column: 50/30 Sephadex G25 fine
Buffer A: 10 mM Ammonium bicarbonate
Flow: 10 mL/min
Temp: RT
Fractions: 40 mL per fraction Fractions A4+A5 were pooled and applied onto a Capto Adhere column:

Column: Capto Adhere 16/10
Buffer A: 20 mM TEA pH 7.5
Buffer A2: 40 mM TEA+0.2M NaCl pH 7.5
Buffer B: 40 mM MES+40 mM Formic acid pH 3.5
Gradient 1: 0-30% Buffer B over 1 CV
Gradient 2: 30-65% Buffer B over 15 CV
Gradient 3: 65-100% Buffer B over 1 CV
Flow: 3 mL/min
Temp: RT
Fractions: 3 mL per fraction in peak fractionation Fractions A4-A9 were pooled and buffer changed to PBS buffer by UF (Amicon ultra 15K) affording the desired hGH-linker-Fc conjugate [(bis(2-(2-Fc-S3-acetamido)ethylamine)))-Gly-OEG]-carbonylmethylene-S¹⁰¹-hGH[L101C].

Yield: 91 mg (28%)
LC-MS (electrospray): Found m/z=72338.69; Calculated m/z=72335.8008
Purity on HPLC: 81% at 214 nm.

GH-FC Conjugate 4

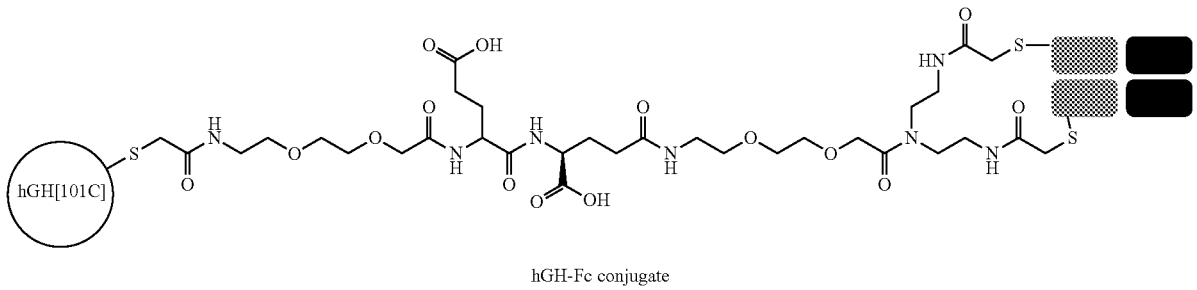 [SMILES: CSCC(=O)NCCOCCOCC(=O)NC(CCC(=O)O)C(=O)N[C@@H](CCC(=O)NCCOCCOCC(=O)N(CCNC(=O)CSC)CCNC(=O)CSC)C(=O)O]

hGH-Fc conjugate

In a similar way as described above for conjugates 1-3 a conjugate 4 was prepared using trivalent linker 4 of Example 1.

GH-FC Conjugate 5

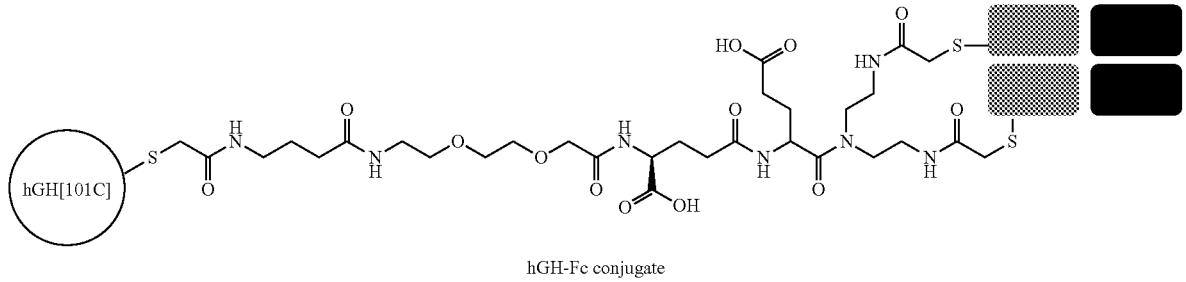

hGH-Fc conjugate

In a similar way as described above for conjugates 1-3 a conjugate was prepared using trivalent linker 6 of Example 1.

GH-Fc Conjugate 1 by Alternative Method
Fc-Linker Intermediate
Step 1

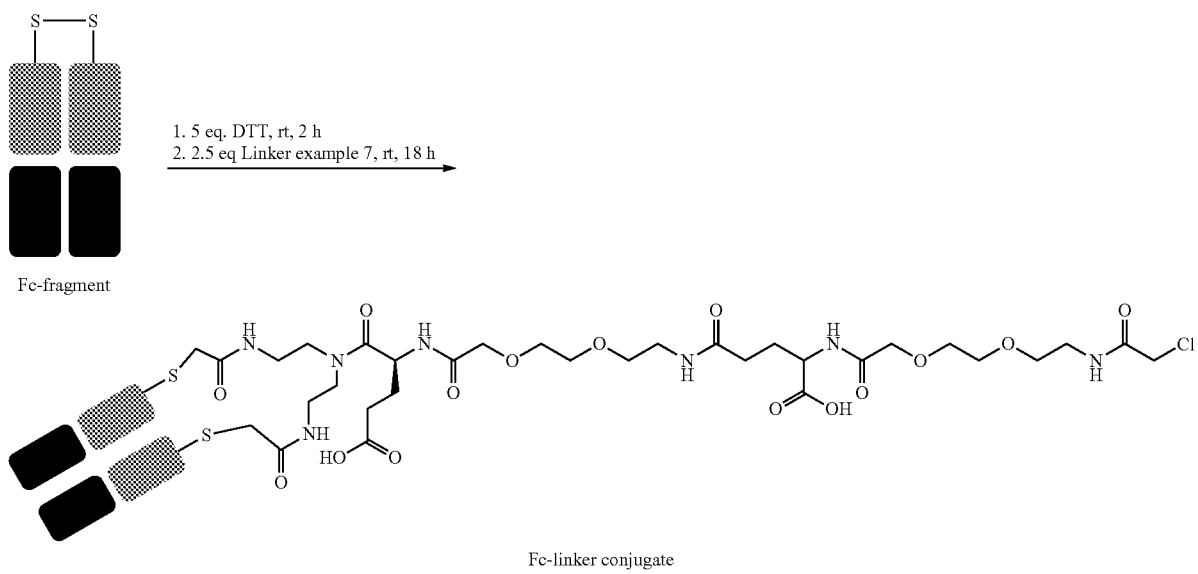

Fc-linker conjugate

Procedure Step 1:

To the Fc-fragment obtained as described above (12 mL, 2.03 mg/mL, 41 µM in 50 mM ammonium bicarbonate, pH 7.8) was up-concentrated with a vivaspin UF device (CU 30 kDa, PES membrane) to 1.9 mL (22 mg, 11.6 mg/mL, 232 µM) was added 220 µL of a 10 mM TCEP solution in PBS (4.3 eq) and incubated for 1 hrs at room temperature. The reaction mixture was buffer exchanged into 50 mM phosphate buffer, 400 mM NaCl, 10 mM EDTA to get 19.25 mg of reduced Fc (7.7 mg/mL, 154 µM as dimer) to which 375 uL of a 5 mM freshly prepared solution of (4S,18S)-4-(bis (2-(2-Bromoacetamido)ethyl)carbamoyl)-18-(2-(2-(2-(2-chloroacetamido)ethoxy)ethoxy)acetamido)-6,15-dioxo-8, 11-dioxa-5,14-diazanonadecanedioic acid in the same buffer was added (2.5 eq) and allowed to incubate in the dark for 18 hrs at rt whereupon the reaction mixture was buffer exchanged by gel filtration into PBS to furnish the target Fc-linker conjugate quantitatively.

Yield=50 mg (95%).

LC-MS (electrospray): Found m/z=50605.58; Calculated m/z=50605,68

Purity on HPLC: 92% at 214 nm.
System: Agilent 1200 series HPLC
Column: Zorbax 300SB-C3, 4.6×50 mm, 3.5µ
Detector: Agilent Technologies LC/MSD TOF (G1969A)
Detector setup: DAD: 280 nm, (G1315A)
Scanning range: m/z min. 100, m/z max. 3000
Linear reflector mode
Positive mode
Conditions: Step gradient: 5% to 90% B
Run-time: 12 minutes: 0-1 min 5% B, 1-8 min 5-90% B, 8-9 min 90% B,
9-9.1 min 90-5% B 9.1-12 min 5% B
Flow rate: 1.00 mL/min fixed
Column temperature: 40° C.
Eluents: Solvent A: 99.9% $H_2O$, 0.1% Formic Acid
Solvent B: 99.9% MeCN, 0.1% Formic Acid Reaction Overview of Step 2 Including 3 Separate Steps as Described Below.

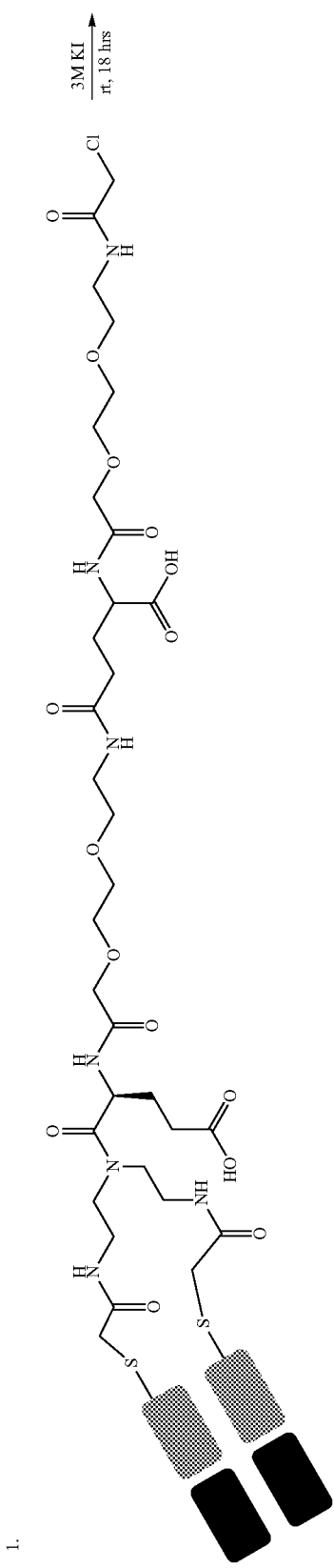
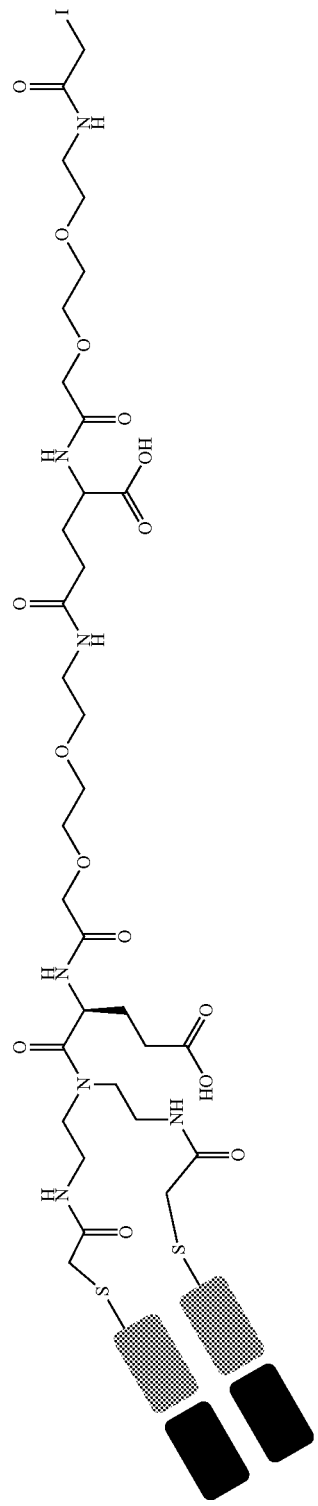
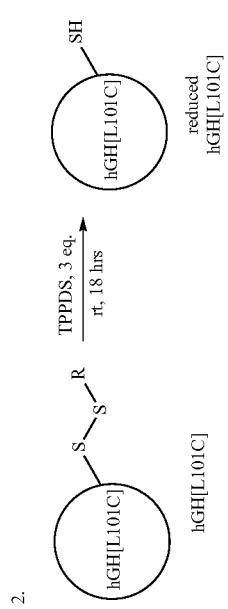

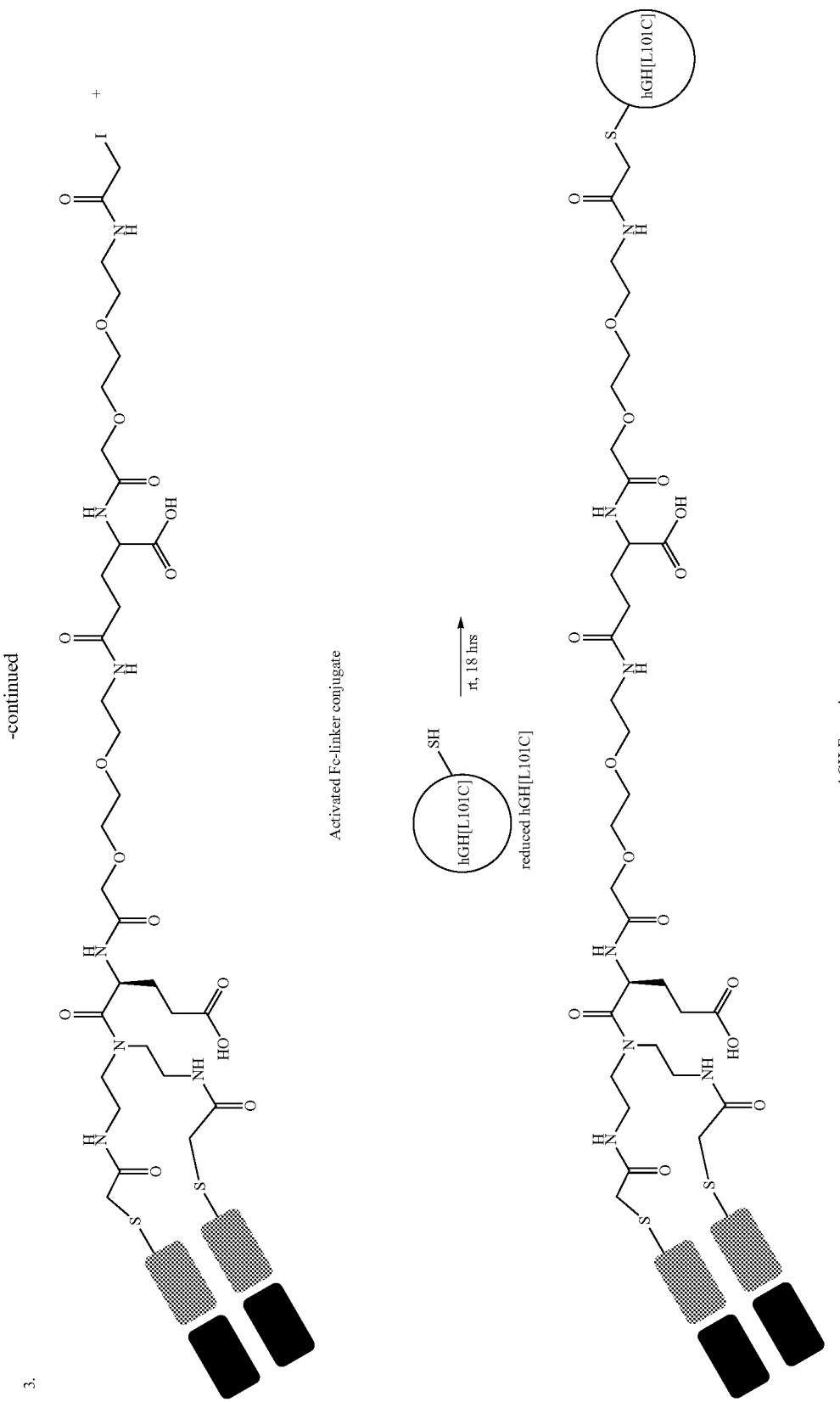

Procedure (Step 2):
1. Chloro to Iodo exchange (Finkelstein reaction): The above compound Fc-linker conjugate from step 1. (2.5 mL, 7.7 mg/mL, 152 µM) was buffer exchange by gel filtration in a Zeba spin column (10 mL size, Pierce) into 50 mM phosphate buffer, 5 M KI, 50 mM ascorbic acid, 100 mM NaCl, pH 6 and incubated at rt in the dark for 18 hrs. Finally, the reaction mixture was up-concentrated with a vivaspin UF device (CU 30 kDa, PES membrane) to 1.3 mL and buffer exchange by gel filtration in a Zeba spin column (10 mL size, Pierce) into 50 mM PB, 1 M NaCl, 10 mM EDTA, pH 7.6 and used immediately in step 3.
2. hGH[L101C] decapping of cysteine: To a vial containing hGH[L101C] (24.75 mg, 4.95 mg/mL, 225 µM, in 20 mM triethylamine, 100 mM NaCl, pH 8) was added 3 eq. bis(p-sulfonatophenyl)phenylphosphine dihydrate dipotassium (TPPDS, 3.6 mg) and incubated at room temperature for 18 hrs. Following, the reaction mixture was buffer exchanged into 50 mM PB, 1 M NaCl, 10 mM EDTA, pH 7.6 and up-concentrated to 17 mg/mL by ultrafiltration (1.45 mL) and used immediately in step 3.
3. hGH[L101C]-Fc conjugate formation: Fc-activated linker conjugate from step 1 (1.3 mL, 14.8 mg/mL, 300 µM) and the free Cys hGH[L101C] compound from step 2 (0.61 mL, 17 mg/mL, 770 µM) were mixed together, obtaining a molar ratio between Fc and hGH[101] of 1 to 1.2. The reaction mixture (1.91 mL) was allowed to incubate in the dark for 18 hrs whereupon the desired conjugate was purified from the reaction mixture on a Capto Adhere 16/10 column operated in HIC mode (CV=20 mL; A: 20 mM TEA, pH 7.5; B: 40 mM MES, 40 mM formic acid, pH 3.5; application buffer: 20 mM TEA, 200 mM NaCl, pH 7.5; segment gradient: segment 1: 0-30% B, 1 CV; segment 2: 30-70% B, 15 CV; segment C: 70-100% B, 1 CV; flow 3 mL/min). Fractions containing product were buffer exchanged in PBS giving 8.6 mg of the desired conjugate (4.3 mL, 2.0 mg/mL, 27.5 µM).

Yield=8.6 mg (30%).

LC-MS (electrospray): Found m/z=72682.09; Calculated m/z=72682.13

Purity on HPLC: 94% at 214 nm.

Example 3 Evaluation of GH Compounds

The GH compounds produced according to above example 2 were evaluated as described in Assay 2, 3 and 5. All compounds were administered intravenously and the mean residence time (MRT) calculated. IGF-1 Plasma concentration-time profiles were generated for each compound.

| GH Compound | RoA | MRT (h) | IGF-1 AUC hr * ng/mL |
|---|---|---|---|
| WT | i.v. | 0.15 | — |
| 1 | i.v. | 16.9 | 26273 |
| 2 | i.v. | 23.4 | 37897 |
| 3 | i.v. | 16.6 | 39956 |
| 4 | i.v. | 23.0 | 37689 |
| 5 | i.v. | 19.7 | 24211 |

The invention claimed is:

1. A protein conjugate of the following structure

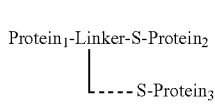

wherein

Linker is a chemical moiety, S is a sulfur atom and

Protein$_1$ is covalently linked to Protein$_2$ and Protein$_3$ via the Linker and sulfur atoms, and wherein Protein$_2$ and Protein$_3$ are Fc polypeptides and Linker is a trivalent linker comprising —NH—C(=O)—CH$_2$—* linked to —S-Protein$_2$ and —NH—C(=O)—CH$_2$—* linked to —S-Protein$_3$ and -* indicates the attachment site to —S—, wherein the Linker is 5-200 atoms in length.

2. The protein conjugate of claim 1, wherein the conjugate has the following structure

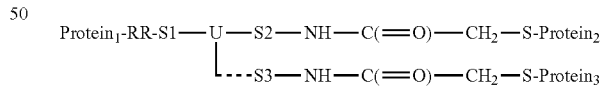

wherein U represents a central unit, RR represents a reactive end radical and S1, S2 and S3 represent individual spacers, wherein the central unit comprises a nitrogen atom or a benzene ring.

3. The conjugate according to claim 1, wherein the sulfur atom's (—S—) are part of thioethers (—CH$_2$—S—CH$_2$—).

4. The conjugate according to claim 2, wherein U comprises a nitrogen atom.

5. The conjugate according to claim 1, wherein the conjugate has the structure:

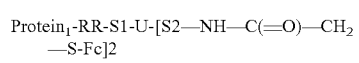

wherein
RR represents a reactive end radical,
U represents a central unit,
S1 and S2 represent individual spacers and
Fc is an Fc polypeptide, wherein the central unit comprises a nitrogen atom or a benzene ring.

6. The conjugate according to claim 1, wherein Protein₁ is a growth hormone.

7. The conjugate according to claim 1, wherein the conjugate has the structure:

GH-RR-S1-U-[S2—NH—C(=O)—CH₂—S-Fc]2 wherein
GH represents a growth hormone molecule,
RR represents a reactive end radical,
U represents a central unit,
S1 and S2 represent individual spacers and
Fc is an Fc polypeptide, wherein the central unit comprises a nitrogen atom or a benzene ring.

8. The conjugate according to claim 1, wherein the hinge region of each Fc polypeptide includes a Cys residue.

9. The conjugate according to claim 1, wherein the sulfur atoms (—S—) are derived from protein cysteines, selected from wild type Cys residues or from variant Cys residues.

10. The conjugate according to claim 2, wherein Protein₁ and S1 are linked via —S—CH₂—C(=O)—NH—.

11. The conjugate according to claim 2, wherein U is a nitrogen atom.

12. The conjugate according to claim 5, wherein U is a nitrogen atom.

13. The conjugate according to claim 7, wherein U is a nitrogen atom.

14. The protein conjugate according to claim 1, wherein the length of the Linker is 10-60 atoms.

15. The protein conjugate according to claim 1, wherein the linker is selected from the group consisting of

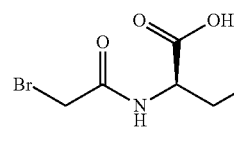
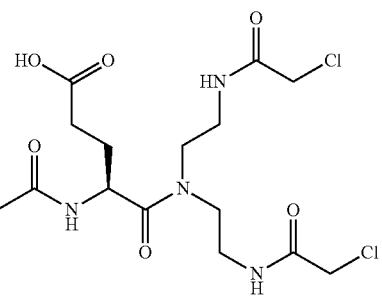

(S)-4-(2-{2-[((S)-1-{Bis-[2-(2-chloro-acetylamino)-ethyl]-carbamoyl}-3-carboxy-propylcarbamoyl)-methoxy]-ethoxy}-ethylcarbamoyl)-2-(2-bromo-acetylamino)-butyric acid,

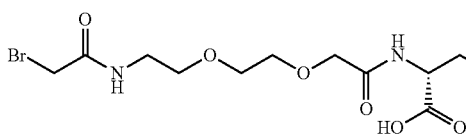
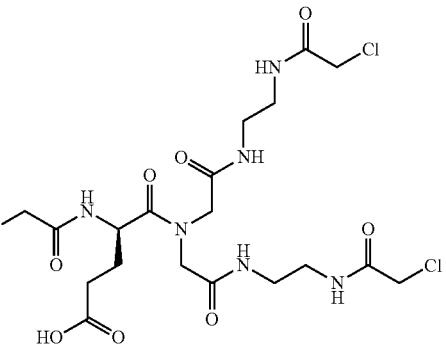

(2R)-5-[2-[2-[2-[[(1S)-1-[bis[2-[2-[(2-chloroacetyl)amino]ethylamino]-2-oxo-ethyl]carbamoyl]-3-carboxy-propyl]amino]-2-oxo-ethoxy]ethoxy]ethylamino]-2-[[2-[2-[2-[(2-bromoacetyl)amino]ethoxy]ethoxy]acetyl]amino]-5-oxo-pentanoic acid,

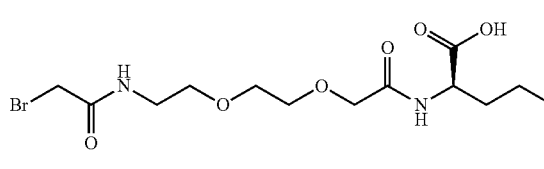
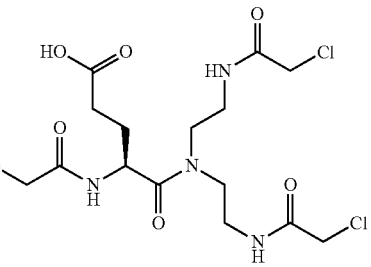

(4S,18S)-4-(bis(2-(2-Chloroacetamido)ethyl)carbamoyl)-
18-(2-(2-(2-(2-bromoacetamido)ethoxy)ethoxy)acet-
amido)-6,15-dioxo-8,11-dioxa-5,14-diazanonadecane-
dioic acid,
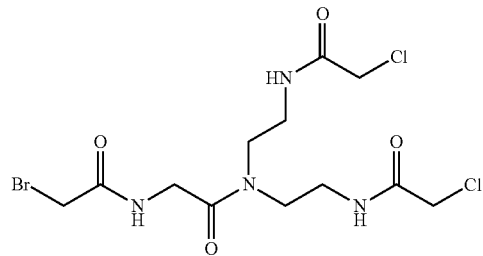 [SMILES: O=C(CCl)NCCN(CCNC(=O)CCl)C(=O)CNC(=O)CBr]
2-(2-bromoacetamido)-N,N-bis(2-(2-chloroacetamido)
ethyl)acetamide,
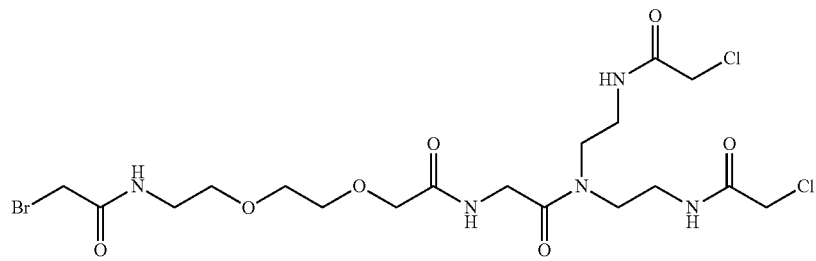 [SMILES: O=C(CCl)NCCN(CCNC(=O)CCl)C(=O)CNC(=O)COCCOCCNC(=O)CBr]
2-(2-(2-(2-(2-bromoacetamido)ethoxy)ethoxy)acet-
amido)-N,N-bis(2-(2-chloroacetamido)ethyl)acet-
amide,
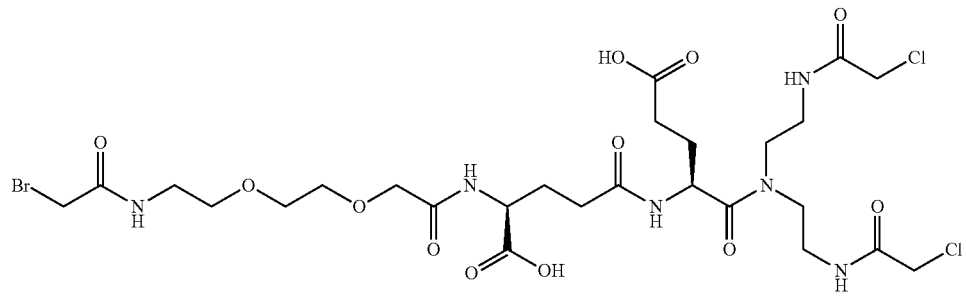 [SMILES: O=C(O)CC[C@H](NC(=O)CC[C@H](NC(=O)COCCOCCNC(=O)CBr)C(=O)O)C(=O)N(CCNC(=O)CCl)CCNC(=O)CCl]
(13R,18S)-18-(bis(2-(2-Chloroacetamido)ethyl)carbam-
oyl)-1-bromo-13-carboxy-2,11,16-trioxo-6,9-dioxa-3,
12,17-triazahenicosan-21-oic acid,
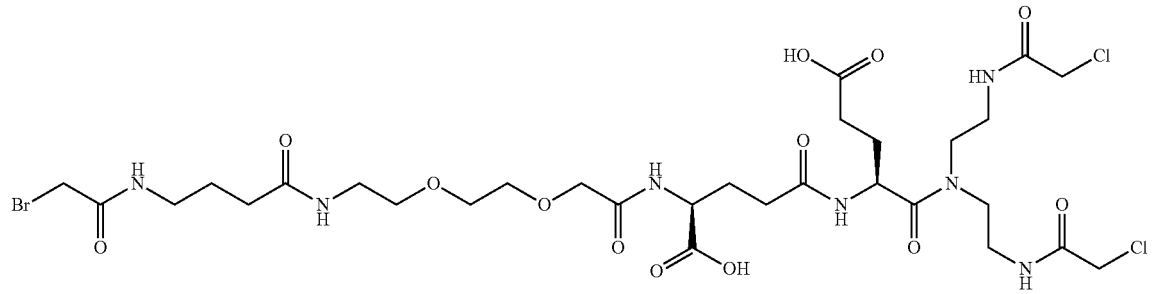 [SMILES: O=C(O)CC[C@H](NC(=O)CC[C@H](NC(=O)COCCOCCNC(=O)CCCNC(=O)CBr)C(=O)O)C(=O)N(CCNC(=O)CCl)CCNC(=O)CCl]

(18R,23S)-23-(Bis(2-(2-chloroacetamido)ethyl)carbamoyl)-1-bromo-18-carboxy-2,7,16,21-tetraoxo-11,14-dioxa-3,8,17,22-tetraazahexacosan-26-oic acid,

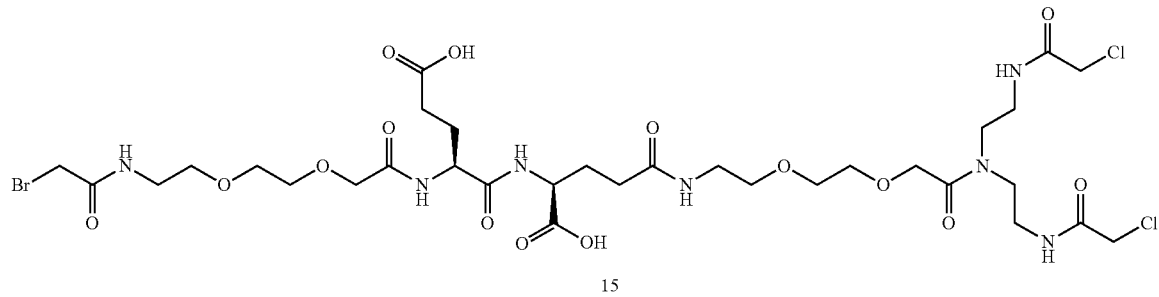

(R)-4-{2-[2-({Bis-[2-(2-chloro-acetylamino)-ethyl]-carbamoyl}-methoxy)-ethoxy]-thylcarbamoyl}-2-[(S)-2-(2-{2-[2-(2-bromo-acetylamino)-ethoxy]-ethoxy}-acetyl amino)-4-carboxy-butyrylamino]-butyric acid,

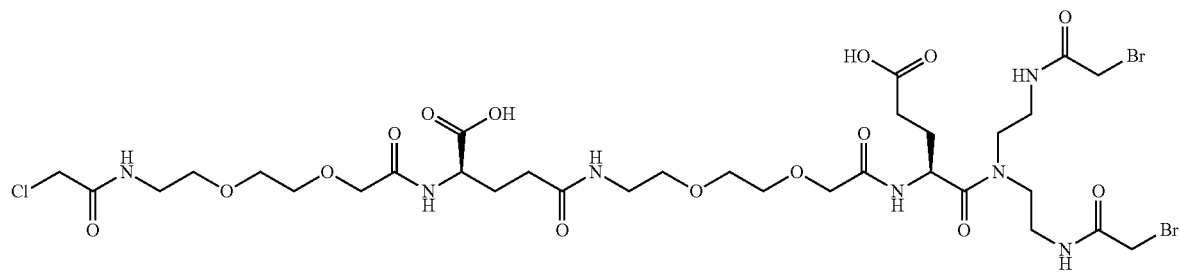 [SMILES: O=C(O)CC[C@H](NC(=O)COCCOCCNC(=O)CC[C@@H](NC(=O)COCCOCCNC(=O)CCl)C(=O)O)C(=O)N(CCNC(=O)CBr)CCNC(=O)CBr]

(4S,18S)-4-(bis(2-(2-Bromoacetamido)ethyl)carbamoyl)-18-(2-(2-(2-(2-chloroacetamido)ethoxy)ethoxy)acetamido)-6,15-dioxo-8,11-dioxa-5,14-diazanonadecanedioic acid,

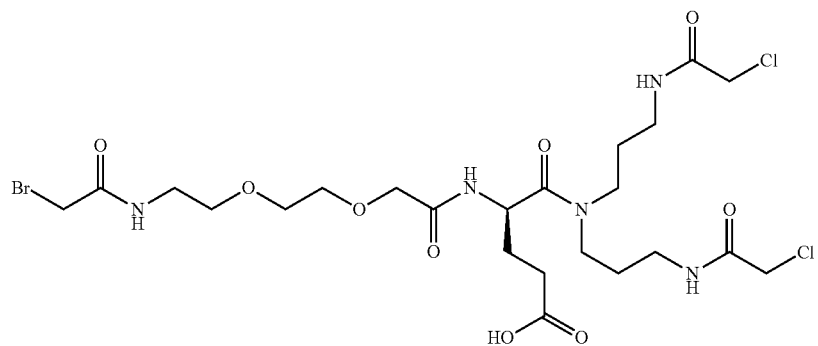 [SMILES: O=C(O)CC[C@@H](NC(=O)COCCOCCNC(=O)CBr)C(=O)N(CCCNC(=O)CCl)CCCNC(=O)CCl]

(4S)-5-[bis[3-[(2-chloroacetyl)amino]propyl]amino]-4-[[2-[2-[2-[(2-bromoacetyl)amino]ethoxy]ethoxy]acetyl]amino]-5-oxo-pentanoic acid,

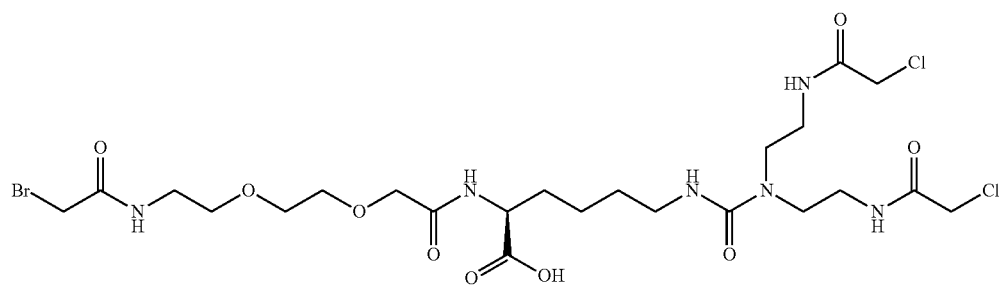 [SMILES: O=C(CCl)NCCN(CCNC(=O)CCl)C(=O)NCCCC[C@H](NC(=O)COCCOCCNC(=O)CBr)C(=O)O]

(2R)-6-[bis[2-[(2-chloroacetyl)amino]ethyl]carbamoylamino]-2-[[2-[2-[2-[(2-bromoacetyl)amino]ethoxy]ethoxy]acetyl]amino]hexanoic acid,

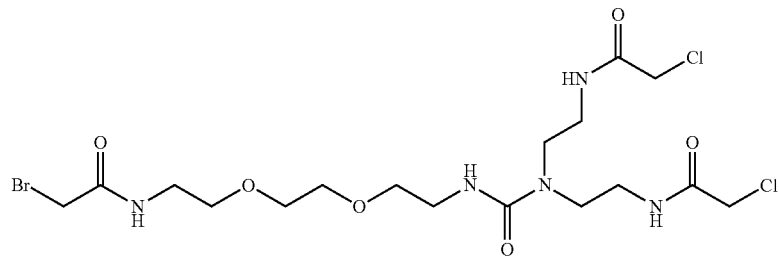 [SMILES: O=C(CCl)NCCN(CCNC(=O)CCl)C(=O)NCCOCCOCCNC(=O)CBr]

N-[2-[2-[2-[2-[(2-bromoacetyl)amino]ethoxy]ethoxy]ethylcarbamoyl-[2-[(2-chloroacetyl)amino]ethyl]amino]ethyl]-2-chloro-acetamide, and

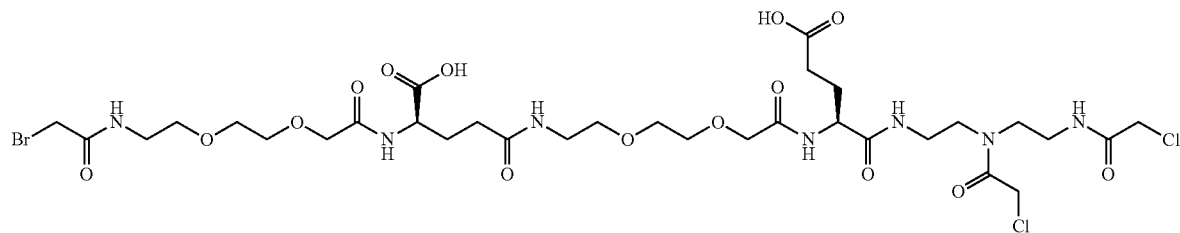 [SMILES: O=C(O)CC[C@H](NC(=O)COCCOCCNC(=O)CC[C@@H](NC(=O)COCCOCCNC(=O)CBr)C(=O)O)C(=O)NCCN(CCNC(=O)CCl)C(=O)CCl]

(2R)-2-[[2-[2-[2-[(2-bromoacetyl)amino]ethoxy]ethoxy]acetyl]amino]-5-[2-[2-[2-[[(1S)-3-carboxy-1-[2-[(2-chloroacetyl)-[2-[(2-chloroacetyl)amino]ethyl]amino]ethylcarbamoyl]propyl]amino]-2-oxo-ethoxy]ethoxy]ethylamino]-5-oxo-pentanoic acid.

16. The protein conjugate according to claim 15, wherein Protein$_1$ is a growth hormone compound.

* * * * *